US012186097B2

(12) United States Patent
Oren et al.

(10) Patent No.: US 12,186,097 B2
(45) Date of Patent: Jan. 7, 2025

(54) HIGH-RESOLUTION PATTERNING AND TRANSFERRING OF FUNCTIONAL NANOMATERIALS TOWARD MASSIVE PRODUCTION OF FLEXIBLE, CONFORMAL, AND WEARABLE SENSORS OF MANY KINDS ON ADHESIVE TAPES

(71) Applicant: Iowa State University Research Foundation, Inc., Ames, IA (US)

(72) Inventors: Seval Oren, Eskisehir (TR); Liang Dong, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 879 days.

(21) Appl. No.: 17/247,112

(22) Filed: Nov. 30, 2020

(65) Prior Publication Data
US 2021/0169419 A1 Jun. 10, 2021

Related U.S. Application Data

(62) Division of application No. 15/994,779, filed on May 31, 2018, now Pat. No. 10,932,721.
(Continued)

(51) Int. Cl.
*A61B 5/01* (2006.01)
*A61B 5/00* (2006.01)
(Continued)

(52) U.S. Cl.
CPC ............ *A61B 5/6832* (2013.01); *A61B 5/002* (2013.01); *A61B 5/01* (2013.01); *A61B 5/1126* (2013.01);
(Continued)

(58) Field of Classification Search
CPC ......... A61B 5/6832; A61B 5/002; A61B 5/01; A61B 5/4266; A61B 5/6804;
(Continued)

(56) References Cited

U.S. PATENT DOCUMENTS

| | | | |
|---|---|---|---|
| 2010/0002402 A1* | 1/2010 | Rogers | H05K 1/118 |
| | | | 361/749 |
| 2013/0098540 A1 | 4/2013 | Lee et al. | |

(Continued)

FOREIGN PATENT DOCUMENTS

CN 103293189 A * 9/2013

OTHER PUBLICATIONS

Chung et al., "Ubiquitous Graphene Electronics on Scotch Tape", Scientific Reports, Appendix D, 8 pages, Jul. 29, 2015.
(Continued)

*Primary Examiner* — Manish S Shah
*Assistant Examiner* — Sharad Timilsina
(74) *Attorney, Agent, or Firm* — McKee, Voorhees & Sease, PLC

(57) ABSTRACT

Methods, systems, and apparatus for high-resolution patterning of various substrates with functional materials, including nanomaterials. A technique of preparing a patterned substrate in a high-resolution mold for stick and transfer process is disclosed with promotes integrity of the high-resolution pattern onto the substrate. One example of a substrate is an adhesive tape. The transferred pattern(s) are scalable and can be implemented in different fabrication processes. One example is a roll-to-roll processes. In one embodiment, the transferred pattern comprises nanomaterials and the substrate comprises a flexible substrate for use in flexible and conformal assemblies for a wide variety of applications including, but not limited to, electrical-based
(Continued)

sensors on non-planar inanimate surfaces, plant body surface, or human or animal skin.

13 Claims, 78 Drawing Sheets
(70 of 78 Drawing Sheet(s) Filed in Color)

Related U.S. Application Data

(60) Provisional application No. 62/513,305, filed on May 31, 2017.

(51) Int. Cl.

| | | |
|---|---|---|
| *A61B 5/11* | (2006.01) | |
| *B32B 7/12* | (2006.01) | |
| *B32B 9/04* | (2006.01) | |
| *B32B 37/00* | (2006.01) | |
| *B32B 37/12* | (2006.01) | |
| *G01L 1/20* | (2006.01) | |
| *G01N 33/00* | (2006.01) | |

(52) U.S. Cl.
CPC .......... *A61B 5/4266* (2013.01); *A61B 5/6804* (2013.01); *A61B 5/6806* (2013.01); *B32B 7/12* (2013.01); *B32B 9/041* (2013.01); *B32B 9/045* (2013.01); *B32B 37/025* (2013.01); *B32B 37/12* (2013.01); *G01L 1/205* (2013.01); *G01N 33/0098* (2013.01); *A61B 2503/40* (2013.01); *A61B 2562/0247* (2013.01); *A61B 2562/0261* (2013.01); *A61B 2562/0285* (2013.01); *A61B 2562/125* (2013.01); *B32B 2457/00* (2013.01)

(58) Field of Classification Search
CPC .............. A61B 5/6806; A61B 2503/40; A61B 2562/0247; A61B 2562/0261; A61B 2562/125; B32B 7/12; B32B 9/041; B32B 9/045; B32B 37/025; B32B 37/12; B32B 2457/00
See application file for complete search history.

(56) References Cited

U.S. PATENT DOCUMENTS

| | | | |
|---|---|---|---|
| 2015/0017403 A1* | 1/2015 | Hyun | C08K 5/13 524/317 |
| 2015/0151528 A1* | 6/2015 | Shimizu | B32B 38/10 428/408 |
| 2016/0195504 A1* | 7/2016 | Swager | B81C 1/00031 438/49 |
| 2020/0073234 A1* | 3/2020 | Watkins | G03F 7/0002 |

OTHER PUBLICATIONS

Das et al., 3D nanostructured inkjet printed graphene via UV-pulsed laser irradiation enables paper-based electronics and electrochemical devices:, Nanoscale, 8, pp. 15870-15879, Sep. 21, 2016.
Tehrani et al., "Rapid Prototyping of a High Sensitivity Graphene Based Glucose Sensor Strip", PLOS One, pp. 1-11 Dec. 17, 2015.
Wang et al., "Simple and Large-Scale Strategy to Prepare Flexible Graphene Tape Electrode", ACS Appl. Mat. Interfaces, 9, pp. 9089-9095, Feb. 21, 2017.
Oren et al., "High-Resolution Patterning and Transferring of Graphene-Based Nanomaterials onto Tape toward Roll-to-Roll Production of Tape-Based Wearable Sensors", Adv. Mater. Technol., 14 pages, 2017.
Kang et al., "Scalable Microfabrication Procedures for Adhesive-Integrated Flexible and Stretchable Electronic Sensors", Sensors, vol. 15, pp. 23459-23476, published Sep. 16, 2015.
Ceylan et al., "Development of a Wireless MEMS Multifunction Sensor System and Field Demonstration of Embedded Sensors for Monitoring Concrete Pavements", Technical Report from Institute for Transportation, Iowa State University, 98 pages, Aug. 2016.
Perabo, "Polyimide Tape—Silicone vs. Acrylic Adhesive", https://www.caplinq.com/blog/, 8 pages, Jan. 10, 2009.
Eda et al., "Large-area ultrathin films of reduced graphene oxide as a transparent and flexible electronic material", Letters, www.nature.com/naturenanotechnology, vol. 3, 5 pages, Aug. 6, 2008.
Oren et al., "Wearable Graphene Sensors on Adhesive Tapes", Solid-State Sensors, Actuators and Microsystems Workshop, Hilton Head Island, South Carolina, 2 pages, Jun. 2016.

* cited by examiner

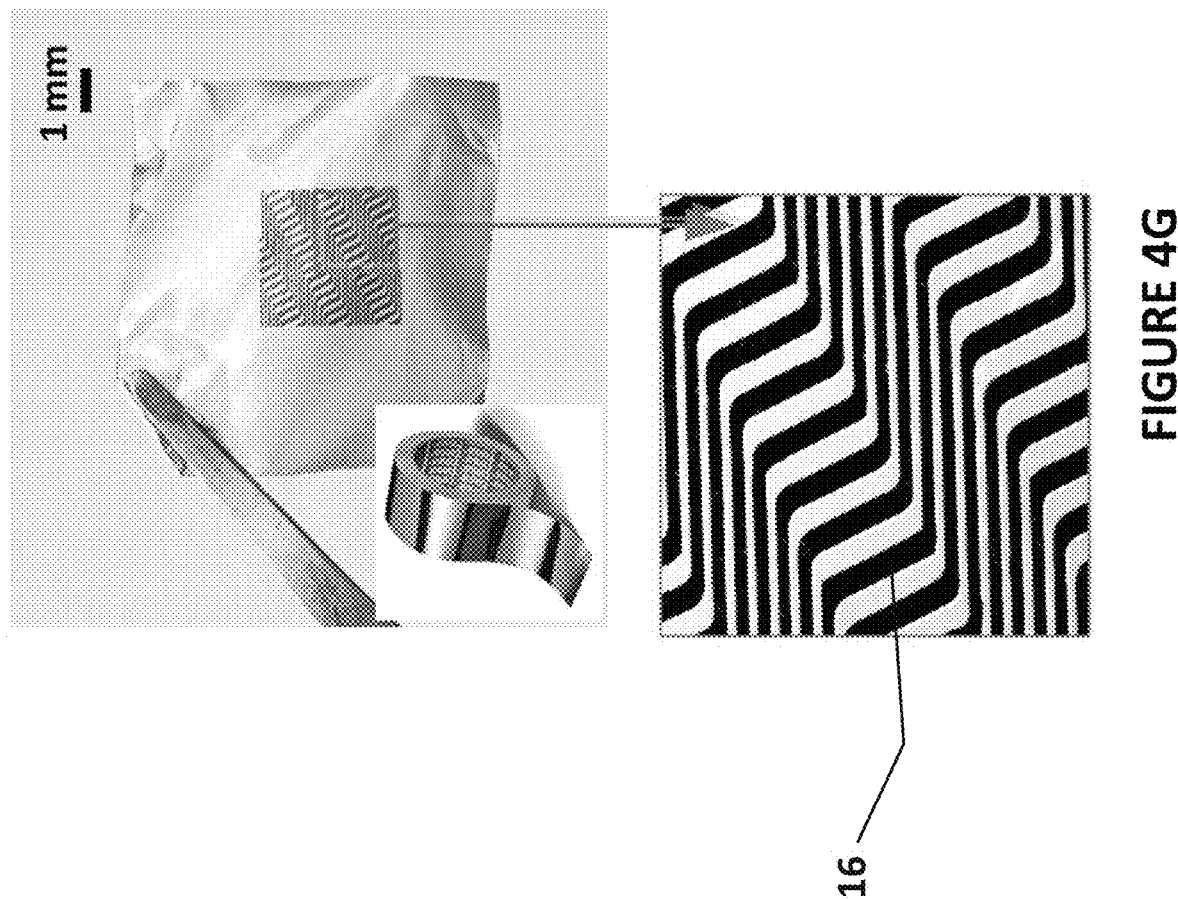

HIGH-RESOLUTION PATTERNING AND TRANSFERRING OF FUNCTIONAL NANOMATERIALS TOWARD MASSIVE PRODUCTION OF FLEXIBLE, CONFORMAL, AND WEARABLE SENSORS OF MANY KINDS ON ADHESIVE TAPES

CROSS-REFERENCE TO RELATED APPLICATIONS

This is a Divisional Application of U.S. application Ser. No. 15/994,779, filed May 31, 2018, which claims the benefit of Provisional Application U.S. Ser. No. 62/513,305 filed on May 31, 2017, all of which are herein incorporated by reference in their entirety.

GOVERNMENT RIGHTS

This invention was made with Government support under Grant No. DBI-1353819, awarded by the National Science Foundation, and under Grant No. 2018-67021-27845, awarded by the United States Department of Agriculture/National Institute of Food and Agriculture. The Government has certain rights in this invention.

I. BACKGROUND OF THE INVENTION

A. Field of the Invention

The present invention relates to design, fabrication, and application of microscale patterns and, in particular, to a simple, high-resolution, and scalable method for microscale patterning and transferring of various functional nanomaterials onto different substrates, including but not limited to types of adhesive tape, and also towards massive production of flexible, conformal, and wearable sensors of many kinds.

B. Problems in the State of the Art

Work in this area involves consideration of a variety of different and sometimes competing factors. First, it is difficult to handle and control nanoscale materials into high-resolution microscale patterns. Second, it is not straightforward how to produce such accurate patterns on flexible, conformal target substrates. Third, complexity and economy of production, including at mass production numbers, is of concern.

Attempts have been made at economically producing small-scale patterning that has sufficient resolution at such small scales but is also versatile regarding mounting to surfaces of interest. These goals are antagonistic with one another. The smaller the scale (particularly of more complex patterns), the more difficult to produce fine resolution. These challenges increase when considering how to mass produce the patterns, including patterns of materials that include, for example, any of a variety of nanomaterials. Small-scale patterns also can have very small thicknesses, which are difficult to make robust in use. The challenges increase if it is desirable to mount the pattern to a surface that may flex, elongate/contract, or otherwise move.

Still further, difficulties exist is trying to manage the foregoing challenges in the context of effective, efficient, scalable, and economical production of a wide variety of pattern shapes, materials, and functionalities. There is, therefore, room for improvement in this technical art.

Further discussion of issues and problems in this technical area are set forth later, including specific examples of implementing aspects of the present invention.

II. SUMMARY OF THE INVENTION

A. Objects, Features, and Advantages of the Invention

It is principle object, feature, and advantage of the invention to provide methods and end products which improve over or solve problems and deficiencies in the current state of the art.

Further objects, features, and advantages include but are not necessarily limited to methods, systems, apparatus, and end products which:

a. provides high resolution of patterns using nanomaterials, including at just a few micrometers or smaller scale in spatial resolution between pattern features and in thickness control;
b. allows for high diversity in types of functional nanomaterials and patterns employed;
c. enables end products which can be flexible and therefore can be conformal to a variety of target placements and uses, including those which bend, flex, or crumple;
d. is scalable, including from one-at-a-time pattern production to high volume, large scale processing;
e. is non-complex and low-cost relative to at least many state of the art production techniques;
f. is adaptable or tunable to different final applications, for example, to different electrical parameters such as for electrical-based sensors, circuits, or patterns;
g. enables easy installation of sensors, circuits, and patterns onto surfaces or objects.

These and other objects, features, and advantages will become more apparent with reference to the accompanying specification and claims.

B. Aspects of the Invention

One aspect of the present invention is the combination of a substrate with a high resolution, small scale pattern applied. The pattern can be on any of a variety of nanomaterials. The pattern can be produced by depositing the nanomaterials into a mold fabricated with a high-resolution negative of the desired pattern. The molded nanomaterials can then be transferred from the high-resolution mold to the substrate. The technique is controlled to at least substantially retain the resolution of the mold. In one example, this control includes cleaning the surface of the mold so that extraneous nanomaterials outside the negative mold are removed prior to transfer to the substrate. This subtle step carries forward the level of resolution of the mold to the substrate. In one example, the substrate has an adhesive side that is pressed against the negative mold. Removal of the substrate is controlled to remove substantially all of the nanomaterials in the negative mold (or at least a sufficient amount for both designed functionality of the pattern). In some examples, the adhesive substrate is a flexible adhesive tape. The nanomaterials are picked out of the mold and held in the high-resolution pattern by the tape adhesive. The unpatterned portions of that side of the tape can be used to adhere the combination of pattern and tape to another surface. The pattern is then in abutment or at least at or near the other surface. Non-limiting examples include on plant, human, or animal tissue or skin surfaces with the pattern(s) functionalized as sensors (e.g. biochemical), on clothing with the pattern(s) functionalized as sensors, on other substrates, surfaces, housings, or machines with the pattern(s) functionalized as sensors. In some examples the substrate is not flexible or adhesive tape material. The pattern can be transferred by methods including $D^2SP$ and ST as examples. Other layers (e.g. an insulation layer or a physical barrier layer) could be added over the exposed side of the pattern on the substrate. Single or plural patterns can be fabricated on the substrate. If plural, the patterns can be all the same or different. Additionally, other patterns or layers can be added to the substrate. Some can be other than nanomaterials. A few non-limited examples are metallized thin-layer patterns or configurations like antennas, temperature sensors, or other. The apparatus can be fabricated one-at-a-time but can advantageously be produced in plural replicas on the same starting substrate (e.g. several, tens, hundreds, or more at a time). One technique is pressing flexible adhesive tape onto the substrate, and then peeling the tape off to consummate the transfer. Another technique is roll-to-roll transfer, where both the mold is flexible (and can rolled up into a roll) and the substrate is flexible (and can be rolled up prior to pressing to the mold, and after). The starting substrate, with many patterns, can then be diced to create individual combinations of substrate/pattern(s) as desired.

Another aspect of the invention involves methodologies to fabricate the apparatus described above. A high-resolution starting negative mold can be efficiently made by known MEMs techniques. Such techniques allow a wide variety of pattern configurations, from simple to complex, by computerized design and then MEMs fabrication of the negative mold. The material for the pattern filled into the negative mold. Controlled steps can be undertaken to clean the mold to leave only the material in the negative pattern. The material is then transferred from the high-resolution negative pattern to a substrate. Controlled steps can be undertaken to maintain resolution of the pattern substantially the resolution of the negative pattern. The transferred pattern is held in place on the substrate and substantially in its positive, high resolution form. The process can produce a combination of one pattern on a substrate, many of the same patterns on a substrate, or different patterns on a substrate. The negative mold just has to be fabricated accordingly. Once the pattern(s) have been transferred to the substrate, they can used together or separated.

Another aspect of the invention involves the types of and control of functional properties of the patterned materials. In one example, nanomaterials are used because of both the ability to select and condition them for, inter alia, different physical, electrical, optical, magnetic, thermal, and biological properties or characteristics as well as the ability to manipulate them, including into very thin layers (of few or many individual layers, as needed). Still further, at least some nanomaterials (one non-limiting example being graphene) have substantial robustness and retain pattern shape and resolution even on flexible substrates. In one example of conditioning nanomaterials, an annealing step or steps can be applied to the pattern (either in the mold or after transfer to the substrate) to essentially tune at least one of the functional properties of the nanomaterials. In one example, annealing can be ambient around the whole mold or substrate (e.g. the whole environment is heated to controlled temperatures). In another example, annealing can be selective and localized (e.g. laser heating of just selected parts of a pattern or selected patterns of plural patterns on a substrate).

In another aspect of the invention, the patterns can be operatively connected to other components or subsystems. In one example, a pattern can function as a part of an electrical circuit by being conductively connected to other circuit components. One non-limiting example is the pattern functions as an ion-selective electrode and is electrically connected (e.g. by MEMs techniques) to a measurement circuit which reads the electrode and passes the reading to intelligent circuit components calibrated to detect both presence and concentration of ionic species of interest. One example of species of interest is nitrate level of a plant. In another example, a wearable patch on the skin of the human can have the pattern functionalized to measure such things as presence and level of sweat, concentrations of various electrolytes (potassium, sodium, etc.) in sweat, skin oxygen, or other chemical, biological and physical parameters of humans. In analogous ways, sensing at the skin of animals is possible.

In another aspect of the invention, apparatus such as described above can also include other functionalized components on the substrate. In one example, in addition to the transferred pattern from the mold, such things as antennas, temperature sensors, integrated circuits (ICs), or other can be either added to the substrate pre-patterning or post-patterning. In some cases, depending on the components, they might be added during patterning. By MEMs techniques or otherwise, this allows multi-purpose final combinations that can be on the same substrate. In one example, the pattern can be used for one sensing measurement (e.g. $O_2$ or $CO_2$ at the human or animal skin or at the leaf surface) and another component (e.g. temperature sensor) can measure temperature at the human or animal skin or at the leaf surface. This allows use of both measurement either for independent purposes or, to the extent possible, correlative purposes. Another example of other components on the substrate can be other layers or devices. In one example, a barrier layer can be added over the pattern. This can either be to prevent contamination of pattern measurements or otherwise. Another example is mounting the patterned substrate to another device. Any of a wide variety of other devices are possible. One non-limiting example is a case, box, or base of any number of form factors, including a housing or non-flexible interface. Another example is a flexible device. Non-limiting examples are clothing, non-adhesive tape, fabric, plastic sheets, paper, metal, wood, and ceramic.

An aspect of the present invention is a method of producing high-resolution, small scale patterned functional nanomaterials on flexible, conformal substrates. A starting solution including the functional nanomaterials is drop cast on a high-resolution mold. In one specific example, a D2SP technique, described herein, uses a cleaning adhesive tape to both clean the mold on unpatterned portions and build up a high-resolution positive of the negative mold pattern for transfer to a second adhesive tape by, in one specific example, a ST technique described herein. The transfer results in a flexible, conformal assembly because the tape is flexible and the positive pattern is adhered to the tape.

Another aspect of the invention is use of the above-method to create long lengths of transfer rolls bearing plural transferred positive patterns of nanomaterials.

Another aspect of the invention is flexible, conformal sensor assemblies with the positive patterns comprising portions of one or more sensors that can be applied to non-planar and flexible target surfaces such as human or animal skin, fabric, or plants.

Another aspect of the invention is production of one or more sensors by methods so as above and configuring the sensors into functional sensor assemblies including but not necessarily limited to force, pressure, strain, chemical, biological, electrical, electronic or other sensors with other circuitry, both for local or remote sensing.

Another aspect of the invention is combination with such other circuits, interfaces, and systems for flexible, conformal sensor systems.

Aspects of the invention include economical, microscale or smaller, high resolution patterning of substrates with, for example, a variety of functional nanomaterials by a high-resolution molding of the nanomaterials and a controlled transfer from the mold to the substrate retaining at least on the order the high resolution of the mold.

III. BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and B. FIG. 1A includes subparts a-g) which illustrate the following: A schematic representation of one exemplary embodiment according to the invention, a graphene pattern formation on tape. a) Negative patterns created on the PDMS substrate via soft lithography. b) Graphene suspensions drop-coated onto the entire surface of the PDMS slab. c) A graphene film formed on the PDMS surface. d) The graphene film outside the negative patterns removed using Scotch tape. e) Graphene patterns formed inside the negative patterns at the PDMS surface. f) A target tape adhered onto the PDMS surface. g) Graphene patterns transferred onto the target tape. FIG. 1B includes subparts h-l which illustrate the following: h,i) Optical images showing the main steps of graphene patterning and transferring process. The scale bars represent 1 mm. h) Graphene patterns obtained in the PDMS structures. The negative patterns on the PDMS substrate were 15.4 µm deep. The graphene inside the PDMS negative patterns were 10.3 µm thick. i) Application of the ST process for graphene pattern transfer onto the polyimide tape. j) PDMS surface after graphene transfer. k,l) Graphene patterns transferred onto the polyimide tape.

FIGS. 2A-H. FIGS. 2A-E illustrate the following: Versatile graphene patterns formed on the polyimide tape using the method of FIGS. 1A-B. FIGS. 2F-H illustrate the following: Formation of graphene patterns on the relatively large polyimide tape roll with liner. The transferred graphene patterns are protected by a nonsticky liner.

FIGS. 3A-K. FIG. 3A) A schematic representation of a specific non-limiting example of a method according to the invention, namely forming a thick graphene film over the entire PDMS surface by one time drop-casting, followed by using Scotch cleaning tape to remove the unwanted graphene from outside the patterned areas. FIG. 3B) SEM image of the PDMS channel containing the incomplete graphene pattern. FIG. 3C) A schematic representation of forming a thick graphene film over the entire PDMS surface via multitime D2SP processes. FIG. 3D) SEM images of the PDMS channel filled with the complete graphene pattern after multiple D2SP processes were applied. FIG. 3E) Optical images for three groups of graphene patterns inside the PDMS channels. The numbers "5-500 µm" and "1-3-7" represent PDMS channel widths, and numbers of graphene layers formed inside the PDMS channel by repeated D2SP processes, respectively. FIG. 3F) Thickness and electrical resistance of the graphene filled in the PDMS channel as a function of the number of D2SP coatings. Each coating here is 1.45±0.32 µm thick. FIG. 3G) Analysis of influences of channel width and depth on the transfer process. The magnitudes of 20, 40, and 100 µm represent the channel widths, while the values of 5, 15.4, and 41.6 µm denote the channel depths. The scale bars represent 50 µm. Sheet resistance of transferred graphene patterns (≈10.3 µm thickness) on the polyimide tape at different (FIG. 3H) annealing temperatures and (FIG. 3I) durations (i). XPS survey spectra for graphene patterns transferred onto (FIG. 3J) polyimide tapes and (FIG. 3K) the polyimide tape alone, without thermal treatment and annealed at 150 and 250° C. for 180 min. The error bars in FIG. 3F, FIG. 3H, and FIG. 3I represent standard deviations of three independent experiments using three samples.

FIGS. 4A-H. FIG. 4A) Optical images of the rGO patterns inside the PDMS channels according to the technique of FIGS. 1A-B with a channel depth of 15.4 µm. The numbers "10-500 µm" and "1-2-4" denote the channel widths and numbers of graphene layers inside the PDMS channels, respectively. FIG. 4B) Thickness of the GO patterns measured at different D2SP times. The error bars represent standard deviations of three independent experiments using three samples. Various rGO patterns obtained on the polyimide tapes using a (FIG. 4C) one-time, (FIG. 4D) two-time, and (FIG. 4E) five-time D2SP repeated process, followed by the ST process. Optical images of the graphene patterns fabricated on various tape substrates, including (FIG. 4F) Scotch tape with acrylic adhesive, (FIG. 4G) aluminum foil tape, and (FIG. 4H) Scotch tape with synthetic rubber adhesive.

FIGS. 5A-F. Demonstration of using a transferred graphene pattern as a strain sensor according to exemplary aspects of the invention. FIG. 5A) Relative change in resistance as a function of the tensile strain applied along the length direction of the graphene pattern. The error bars represent standard deviations of three independent experiments using three sensors and demonstrate good reproducibility of the sensors. FIG. 5B) Relative resistance of the sensor with the repetition of 100 loading/unloading cycles by 4.4% strain. FIG. 5C) Enlarged view of FIG. 5B, exhibits a stable sensor performance. FIG. 5D) Hysteresis curve of the strain sensor. FIG. 5E) Monitoring of tension changes on the balloon surface during inflation. FIG. 5F) Monitoring of bending motions of the index finger.

FIGS. 6A-H. Demonstration of using transferred graphene pattern as a pressure sensor according to exemplary aspects of the invention. FIG. 6A) Relative change in resistance as a function of pressure uniformly applied to the polyimide tape surface. The error bars represent standard deviations of three independent experiments using three sensors and demonstrate good reproducibility of the sensors. FIG. 6B) Relative resistance changes of the sensor with repetition of 100 loading/unloading cycles by 330 kPa. FIG. 6C) Enlarged view of FIG. 6B, exhibiting a stable sensor performance. FIG. 6D) Response curve of the sensor with an applied pressure of 80 kPa at a response time of 0.3 s. FIG. 6E) Monitoring of the pulse rate of human wrist. FIG. 6F) Monitoring of the frequency of mouse clicking. FIG. 6G) Cross-sectional view of an array of 10×10 round-shaped graphene sensors for a pressure-mapping application. Top: schematic representation; bottom: fabricated device. FIG. 6H) Top view of a finger (top) and a key (bottom) positioned on the surface of the pressure sensor array and ΔR/R mapping of the pressure distributions.

FIGS. 7A-F. Demonstration of using a smart glove to monitor the pressure and strain levels during catching a tennis ball according to exemplary aspects of the invention. FIG. 7A) An optical image of the graphene sensors attached to the finger joints. FIGS. 7B, C) Positions of the five pressure sensors (P1-P5) and five strain sensors (S1-S5). FIG. 7D) Time-lapse images of catching the tennis ball using the smart glove. The three images represent the three states: preparation (left), adjustment (middle), and catching (right). Responses of the smart glove during catching the tennis ball, including FIG. 7E) pressure and FIG. 7F) strain responses.

FIGS. 8A-E. Demonstration of using the on-tape RH graphene sensors for the estimation of the times required for water movement within the plant from the roots to the lower and upper leaves according to exemplary aspects of the invention. FIG. 8A) A photo of the graphene RH sensor and a commercial RH reference sensor located at the back of the maze leaf. The placement of the two sensors is magnified in the right-hand image to clarify the structure. The scale bar represents 1 mm. FIG. 8B) A schematic illustration of the sensor placement and detection mechanism. FIG. 8C) Resistance of the graphene sensor as a function of RH. The resistance is measured using a RLC meter at 100 Hz operation frequency. The error bars represent standard deviations of three independent experiments using three sensors and demonstrate good reproducibility of the sensors. FIGS. 8D, E) Real-time monitoring of the RH level on the leaf surface after plant irrigation at two maize plants: FIG. 8D) B73 and FIG. 8E) a mixed genetic stock.

FIGS. 9A and B. FIG. 9A includes subparts a-d which illustrate the following: A schematic representation of the formation of graphene patterns on a 1 meter long polyimide tape according to exemplary aspects of the invention. Subparts illustrate: (a) Negative features created on a ¼-inch thick poly(methyl methacrylate) or PMMA sheet using a high-precision CNC milling machine. (b) PDMS precursor solution poured over and cured on the patterned PMMA sheet. (c) PDMS mold with positive features peeled off from the PMMA surface. (d) PDMS precursor solution poured over and curved on the PDMS mold with positive features formed in (c). FIG. 9B includes subparts e-g which illustrate the following: (e) PDMS mold with negative features peeled off from the mold formed in (d). (f) Graphene patterns formed inside the negative patterns at the PDMS surface using the D2SP method. (g) A double-sided polyimide tape adhered onto the PDMS surface containing the negative patterns. (h) Graphene patterns transferred onto the double-sided polyimide tape and then covered by non-adhesive liner.

FIGS. 10A-D. XPS high-resolution spectra of the graphene patterns on a polyimide tape such as created with one or more of the methods described above, without thermal treatment and annealed at 150° C. and 250° C. for 180 min. Subparts illustrate: (FIG. 10A) O 1s. (FIG. 10B) C 1s. (FIG. 10C) Si 2p. (FIG. 10D) N 1s.

FIGS. 11A-D. XPS high-resolution spectra of the polyimide tape alone such as created with one or more of the methods described above, without thermal treatment and annealed at 150° C. and 250° C. for 180 min. Subparts illustrate: (FIG. 11A) O 1s. (FIG. 11B) C 1s. (FIG. 11C) Si 2p. (FIG. 11D) F 1s.

FIG. 12. Optical images of graphene dispersions in ethanol and distilled water (DI) mixture with different volume fraction ratios of ethanol such as could be used with one or more of the methods described above.

FIGS. 13A and B: FIG. 13A is an illustration of an alternative embodiment of a tape-based patterned sensor assembly on a plant leaf according to aspects of the invention. FIG. 13B is a reduced-in-scale schematic for plant sensors-enabled, high-throughput phenotyping system for water use dynamics according to exemplary aspects of the invention.

FIG. 14: Illustrations of an alternative embodiment according to the invention: Subpart (a). Schematic of a wearable, wrinkled RH-temperature sensor able to adapt to plant growth. Subpart (b). Close-up for part of the wrinkled sensor showing the laminated sensing strip.

FIGS. 15 and 16. Preliminary work of forming wrinkled surface [1].

Figure 17:
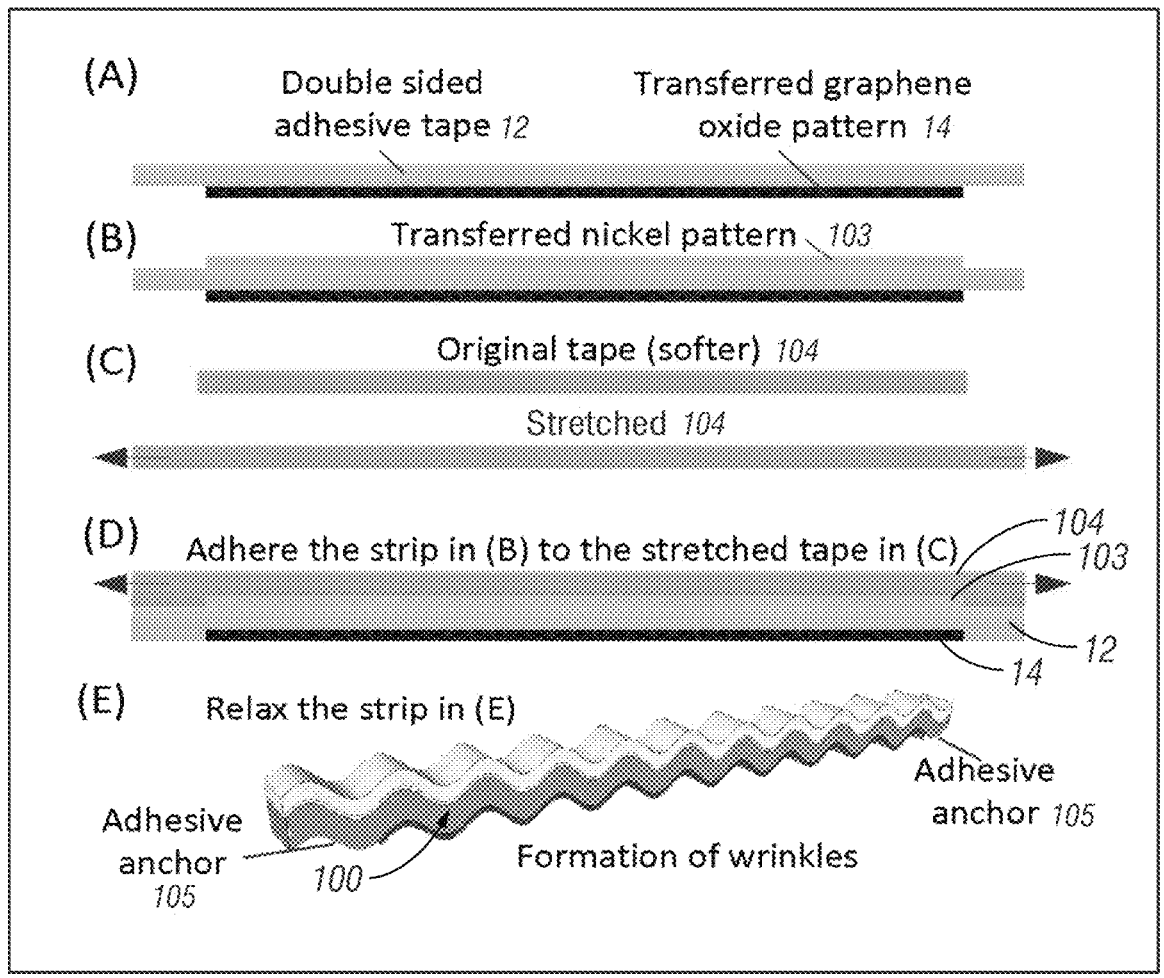

FIG. 17: Fabrication process flow for the proposed wrinkled RH-temperature plant sensor that could be created using the techniques of FIGS. 1A-B.

Figure 18:
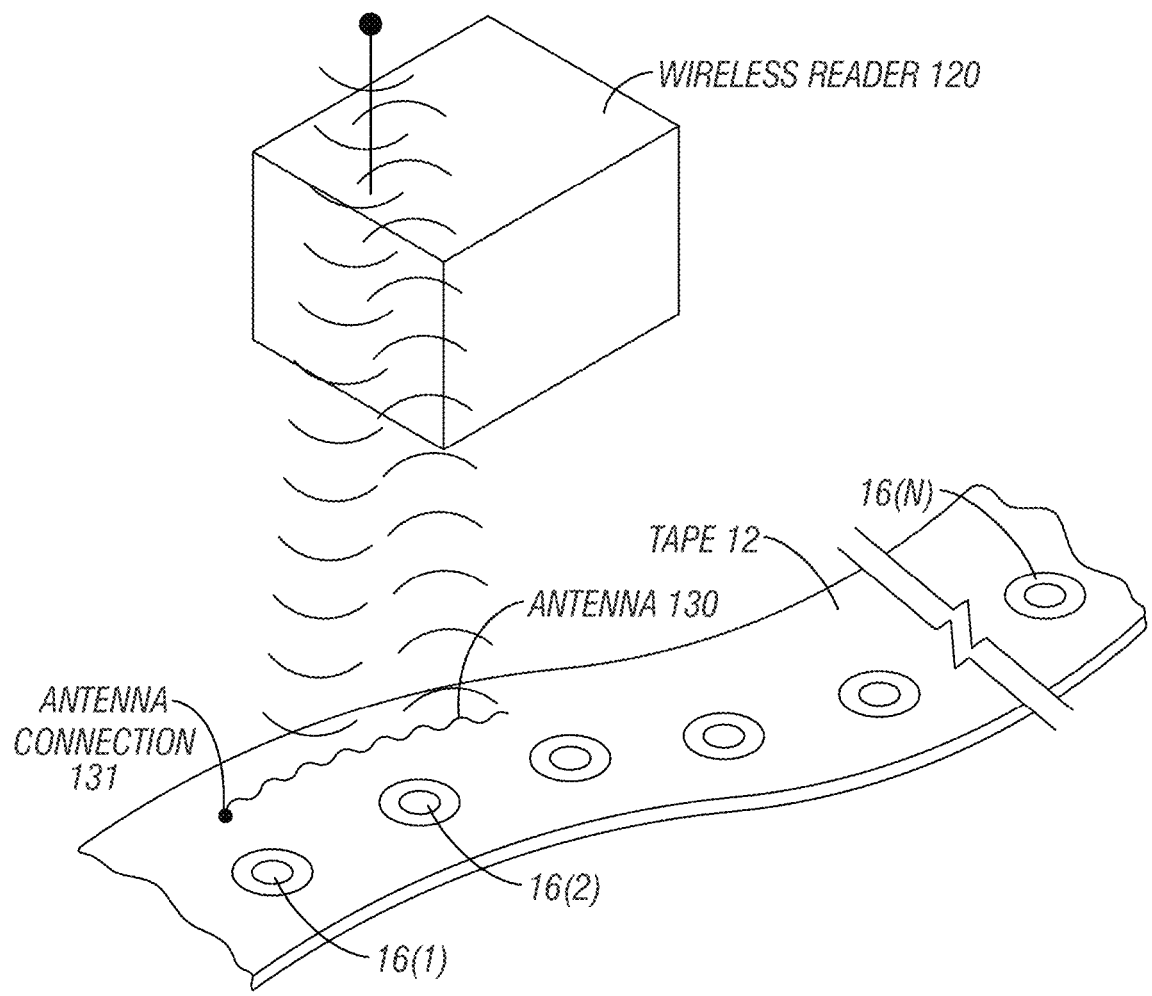

FIG. 18 is a diagrammatic view of a flexible assembly including the extra functional feature of a radio-frequency antenna according to exemplary aspects of the invention.

Figure 19A:
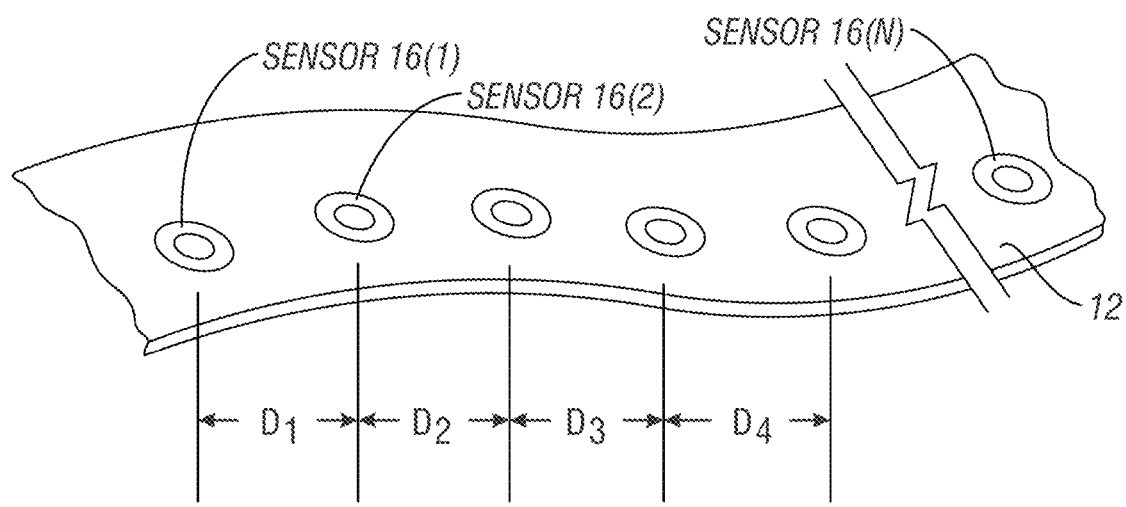

FIGS. 19A and B are a diagrammatic view of a flexible assembly including plural integrated sensors at spaced-apart distances to allow spatially-separated measurements on the same plant (FIG. 19A and a graph showing hypothetical examples of such measurements (FIG. 19B) according to exemplary aspects of the invention.

Figure 20:
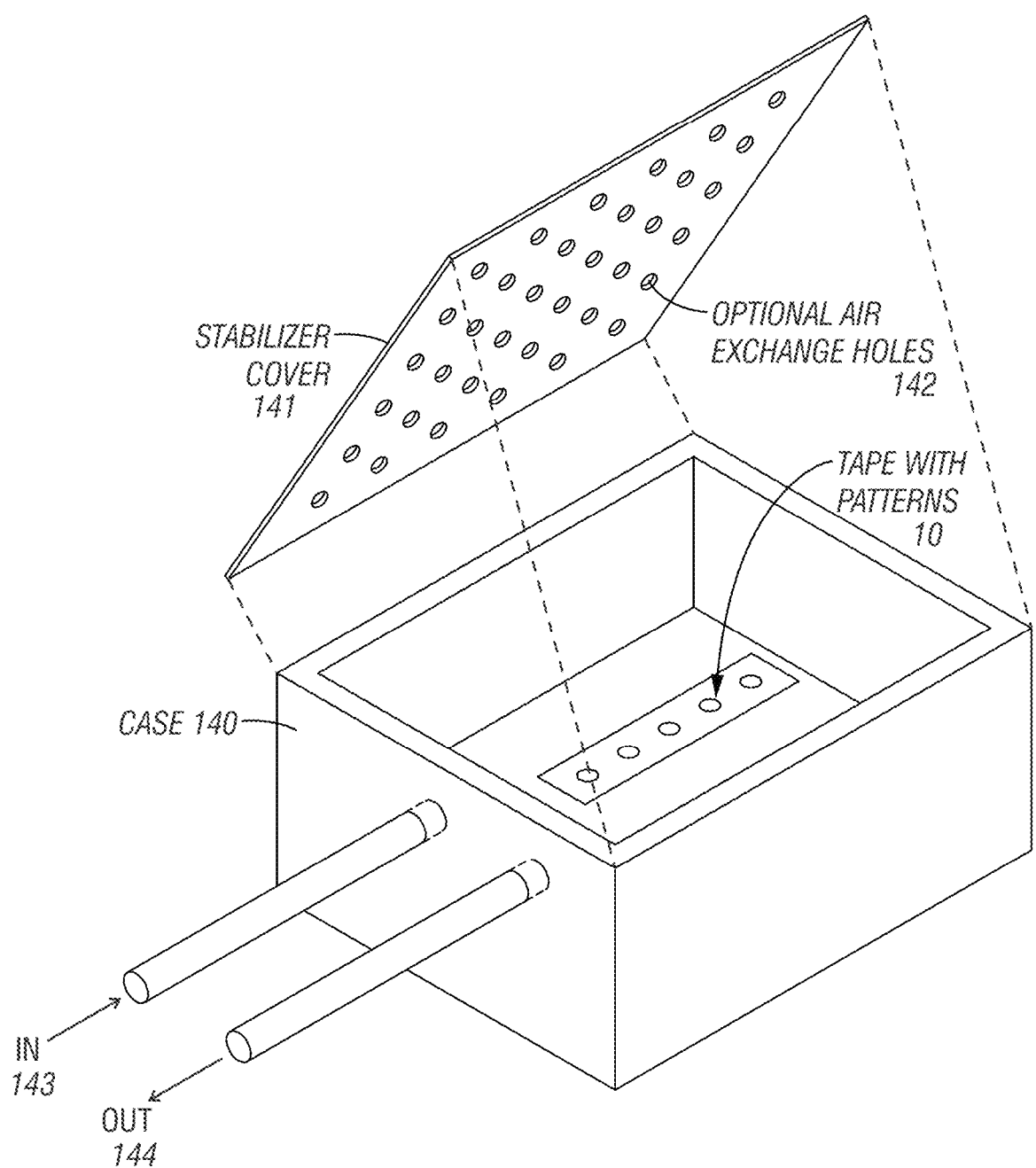

FIG. 20 is a diagrammatic view of an assembly according to an embodiment of the invention mounted onto the surface of a case or housing which can be used to support the assembly or have additional functional features according to exemplary aspects of the invention.

Figure 21A:
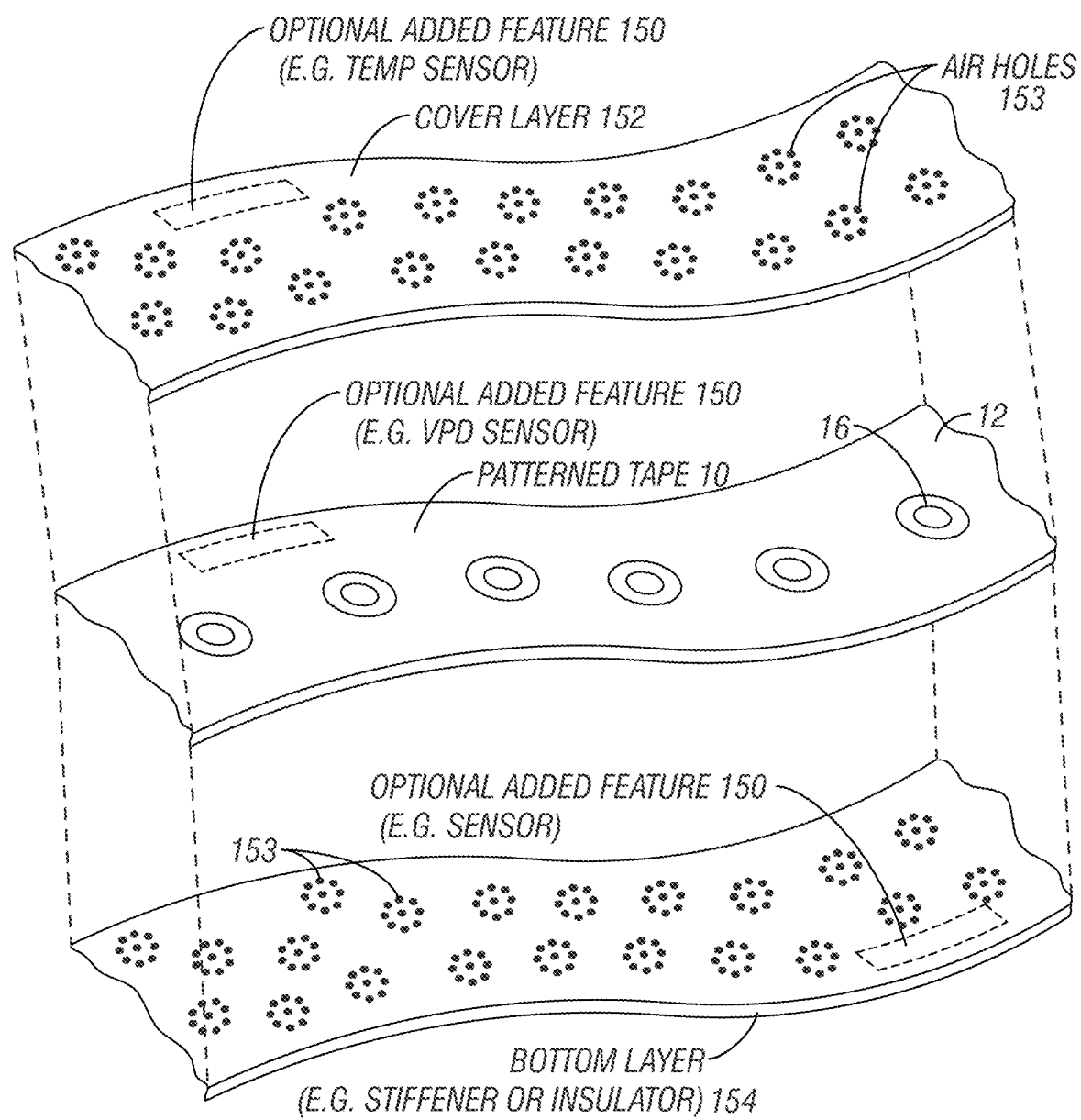
Figure 21B:
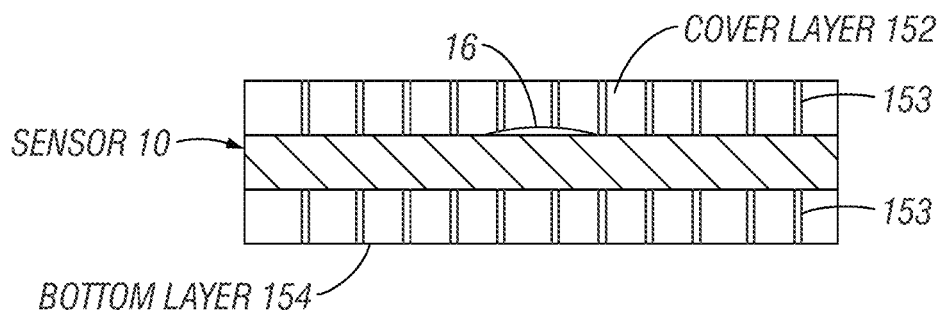

FIGS. 21A and B are diagrammatic views of an alternative embodiment for a flexible assembly according to embodiments of the invention which optionally includes added layers, including but not limited to support layers, air or fluid permeable layers, covering layer over any sensors or circuitry, and the like. These tapes can be stretchable or non-stretchable, flexible or non-flexible, air or fluid permeable or impermeable.

Figure 22:
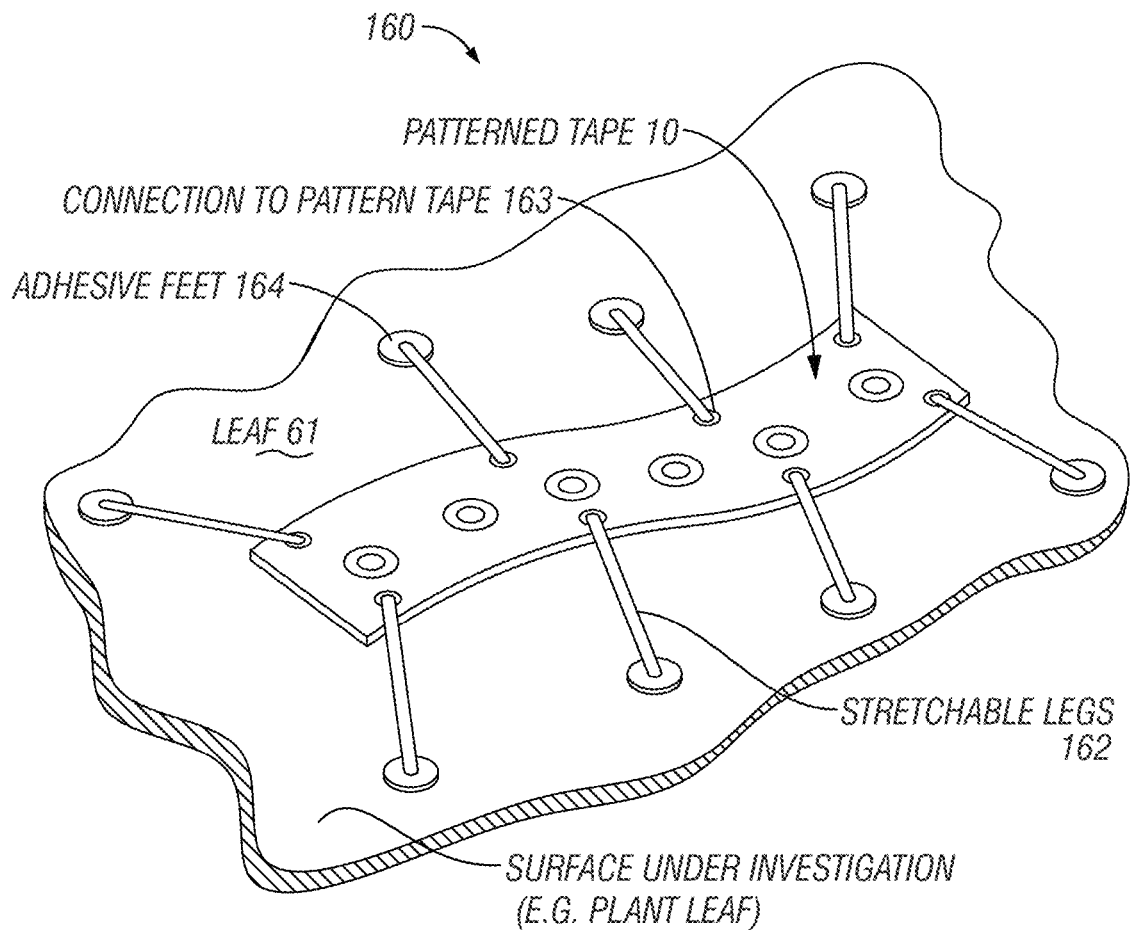

FIG. 22 is a diagrammatic perspective view of an alternative embodiment according to aspects of the invention, in particular, an assembly according to aspects of the invention with an alternative mounting technique comprising elastic legs between adhesive feet and the assembly to, inter alia, allow growth of a plant while maintaining attachment of the assembly to the plant.

Figure 23:
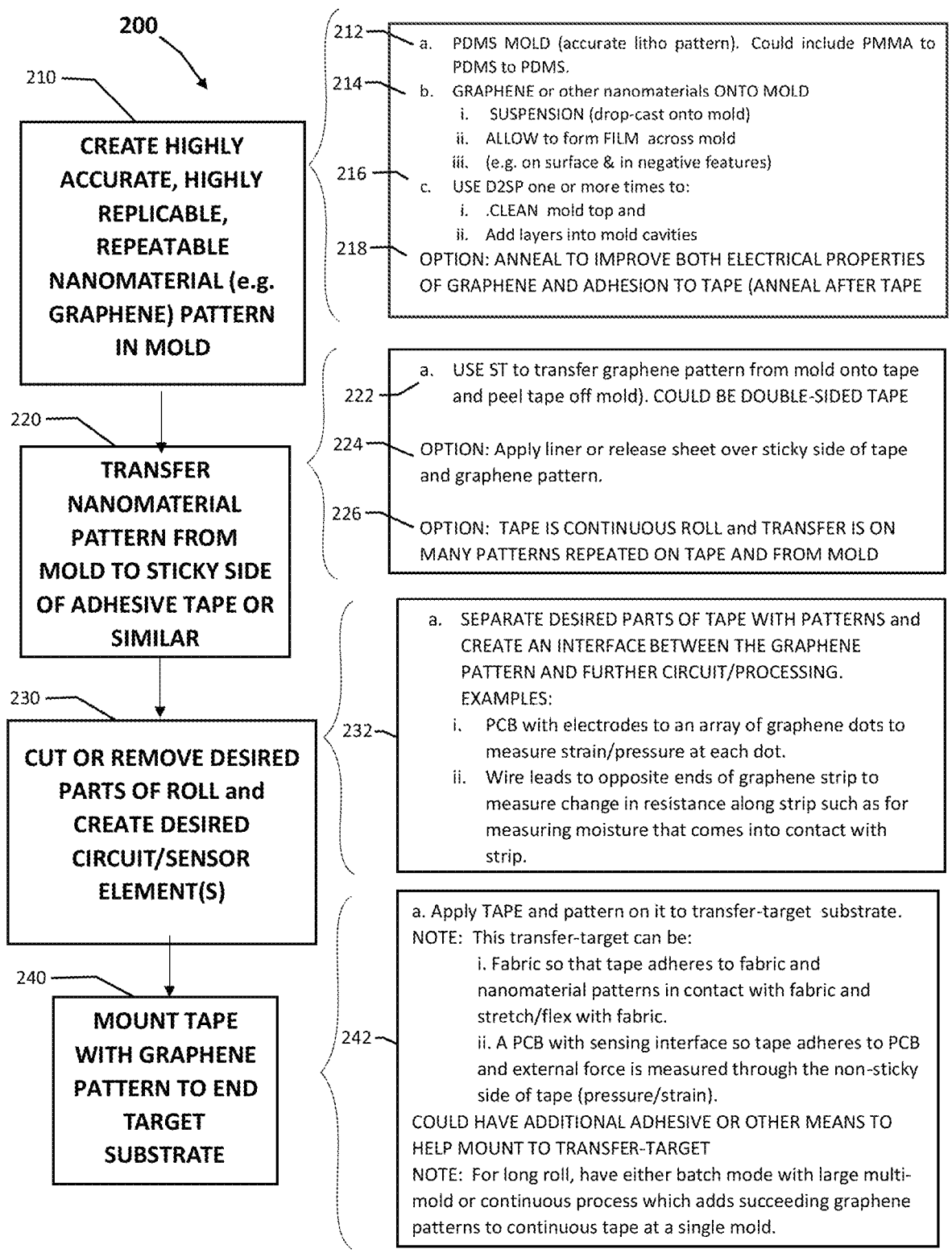

FIG. 23 is a flow chart of a technique of fabricating assemblies according to embodiments or aspects of the invention.

Figure 24A:
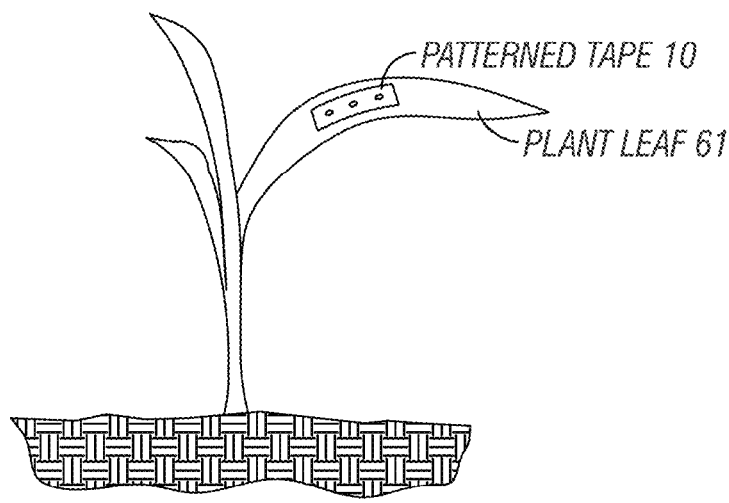
Figure 24B:
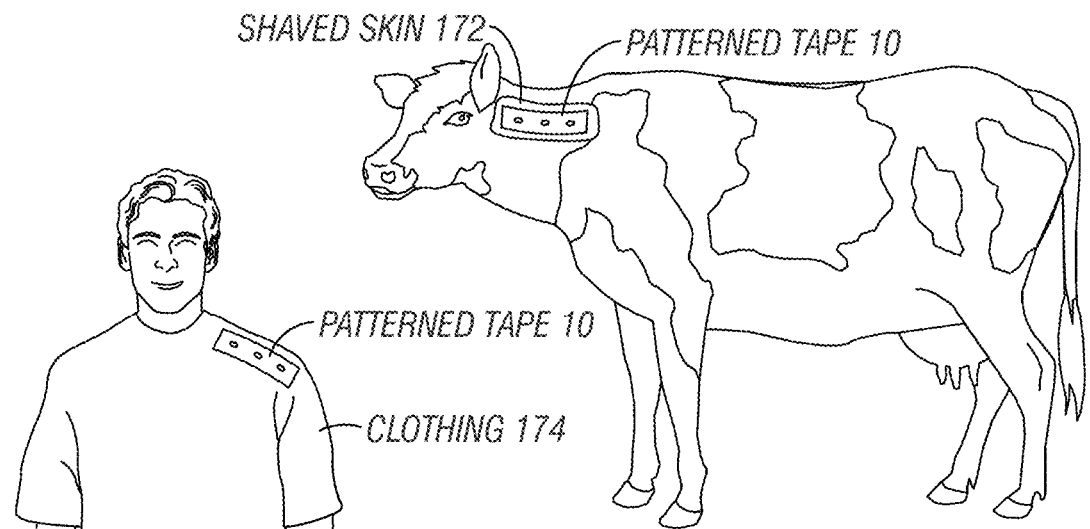
Figure 24C:
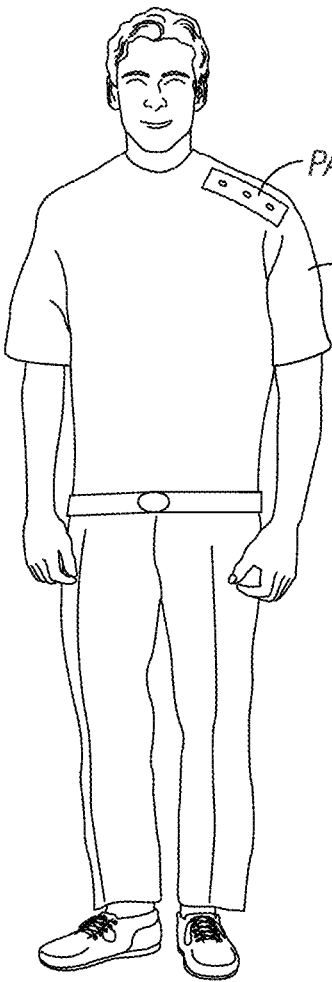

FIGS. 24A-C are highly diagrammatic views depicting assemblies according to aspects of the invention emplaced on plants, humans, and animals respectively.

IV. DETAILED DESCRIPTION OF EXEMPLARY EMBODIMENTS OF THE INVENTION

A. Overview

For a better understanding of the invention and its aspects, several examples of its forms follow. It is to be understood these are examples only and are neither inclusive nor exclusive of all other possible forms. For example, variations obvious to those skilled in the art will be included within the invention.

B. Generalized Embodiment

FIG. 23 is intended to give a more generalized example (indicated generally at ref. no. 200) of aspects of the invention. Details can be derived from the more specific examples that follow it.

Figure 9A:
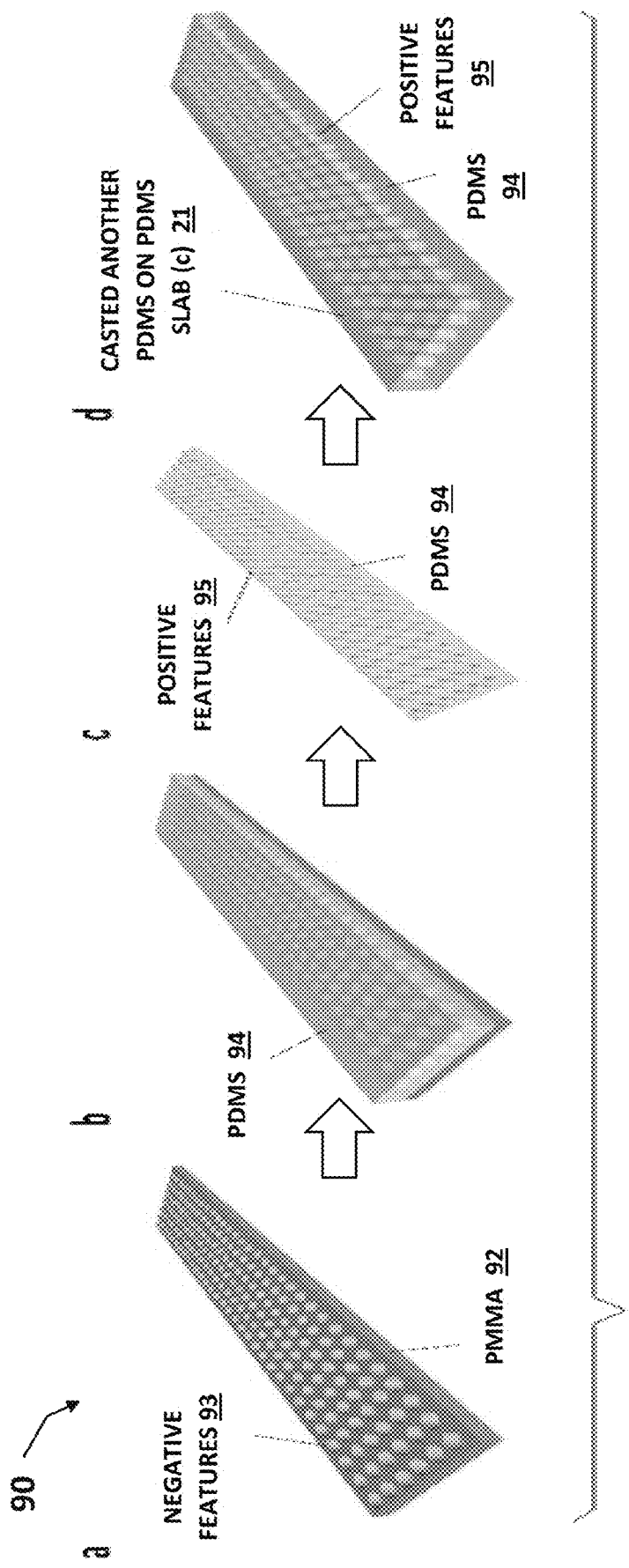
Figure 9B:
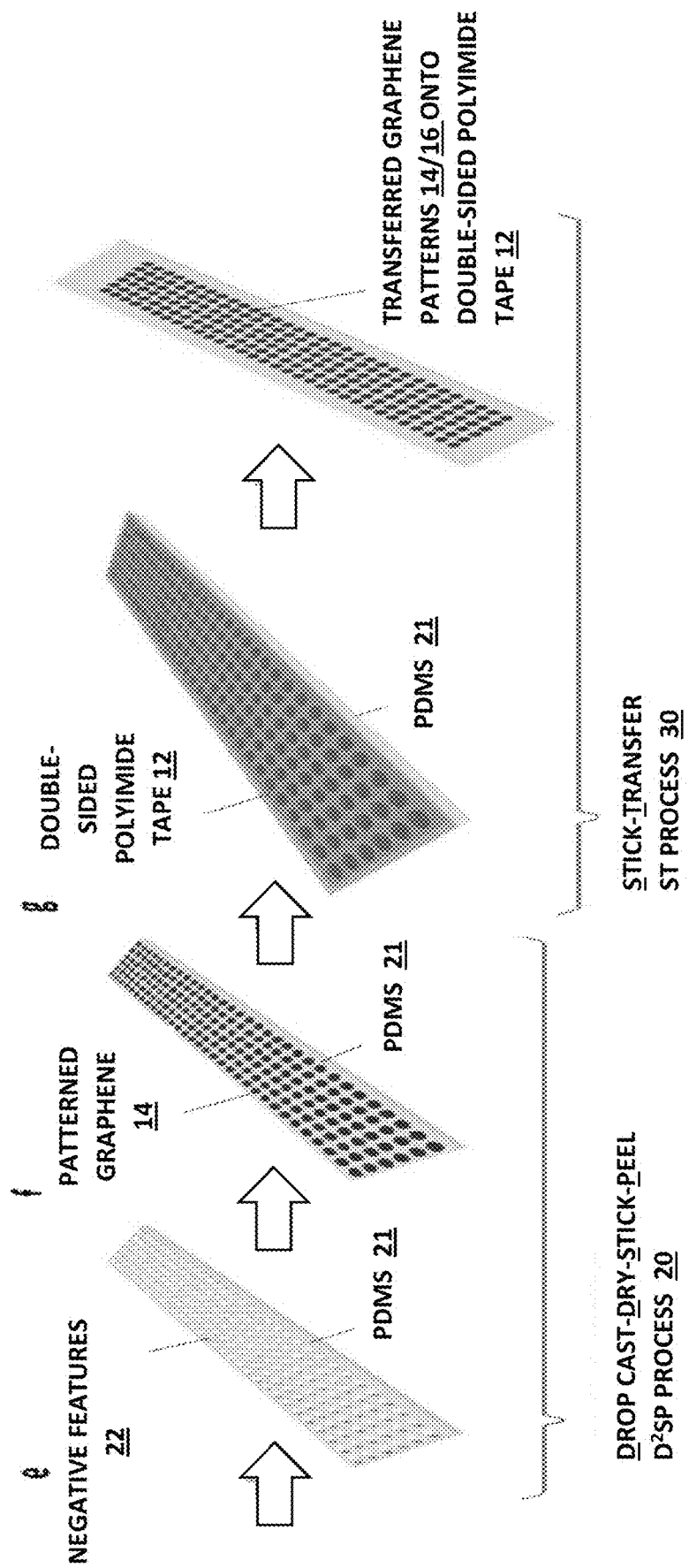
Figure 10A:
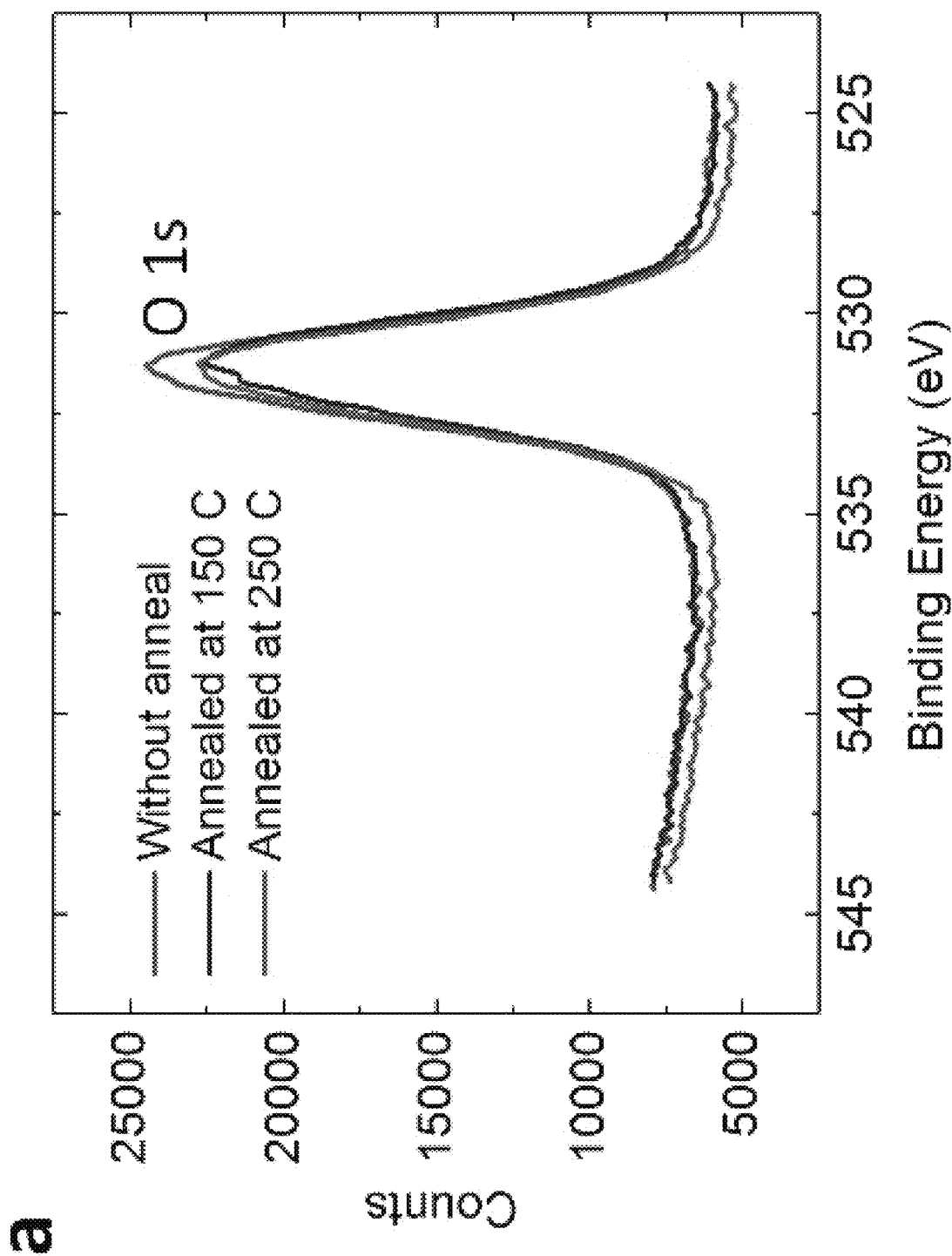
Figure 10B:
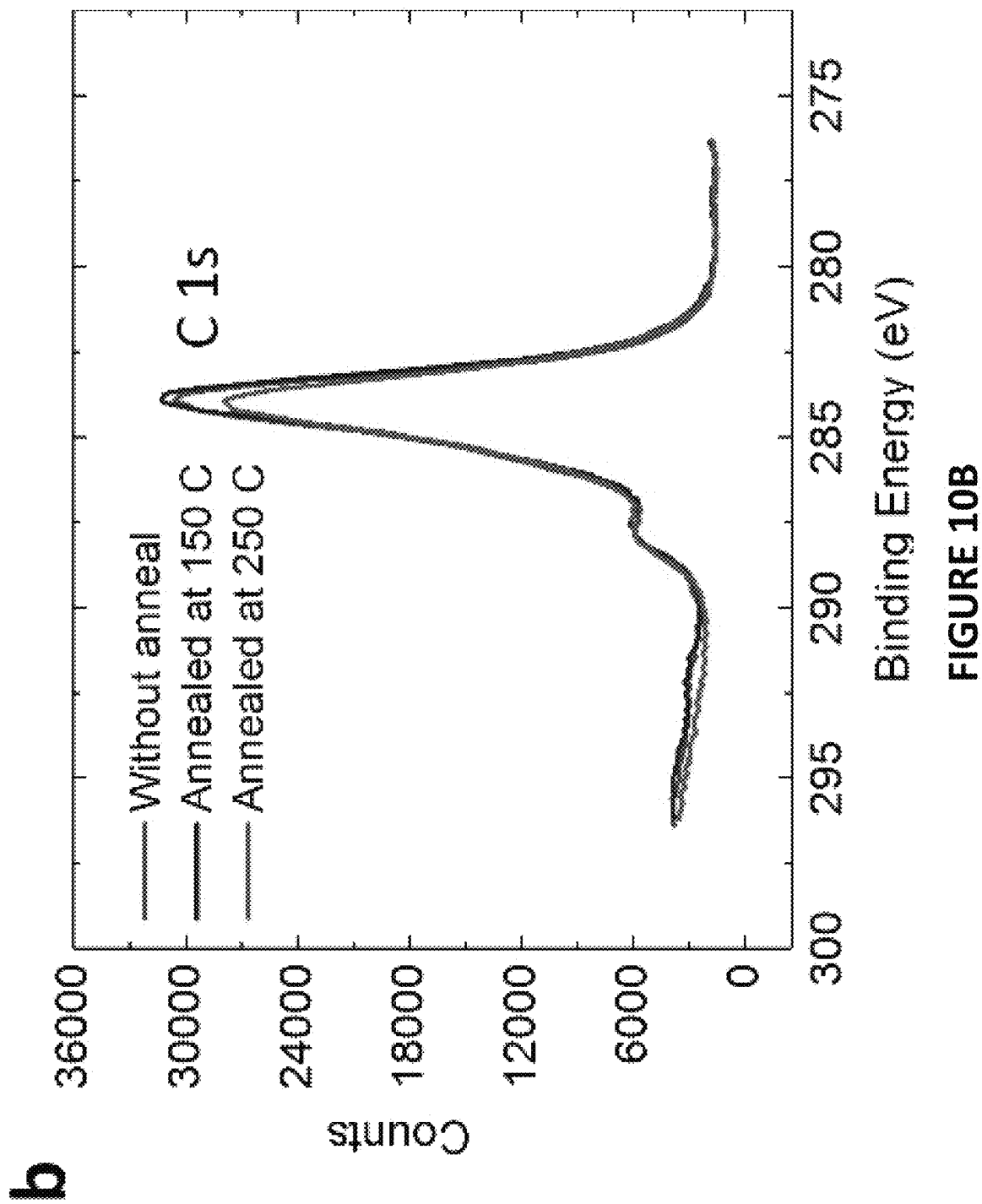
Figure 10C:
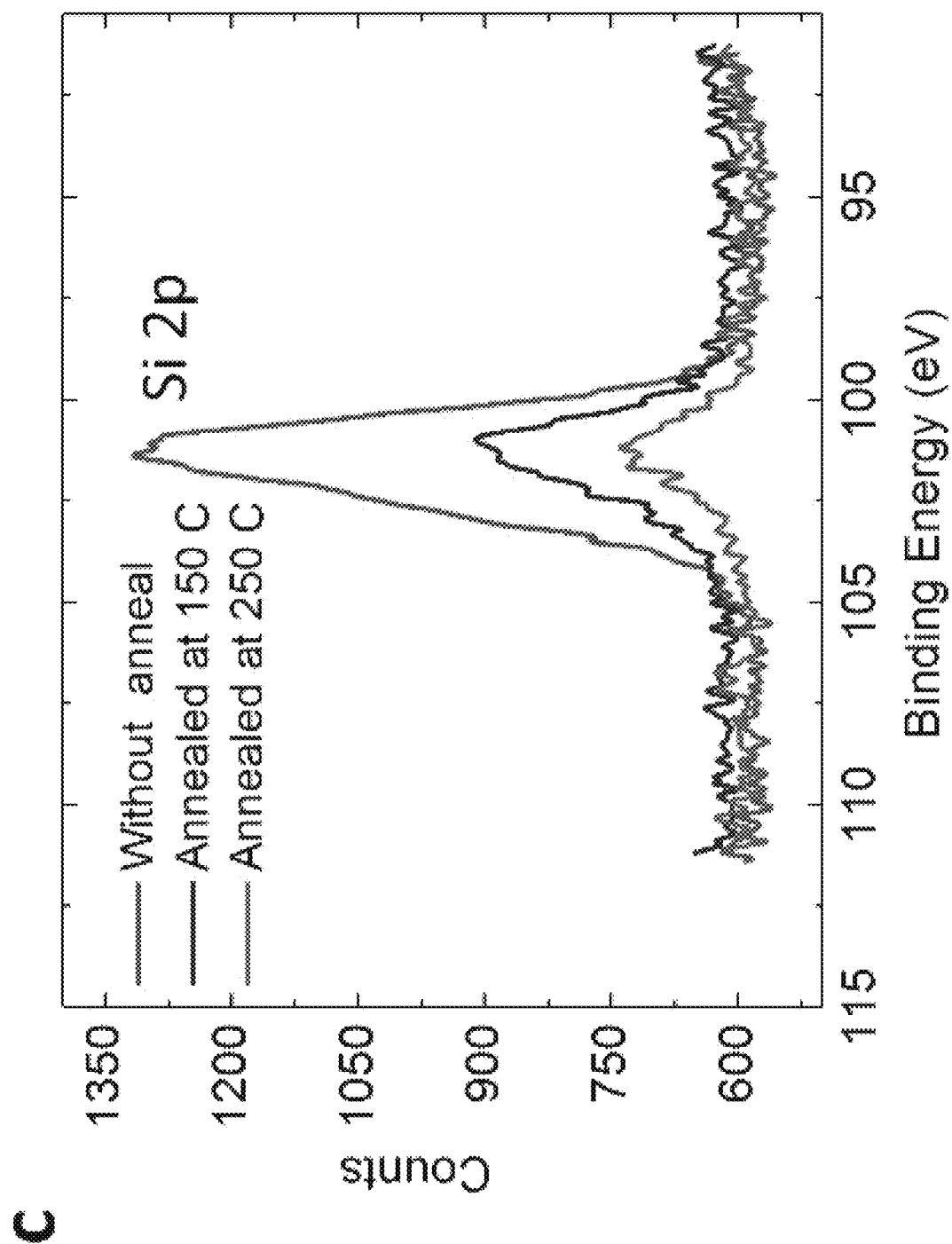
Figure 10D:
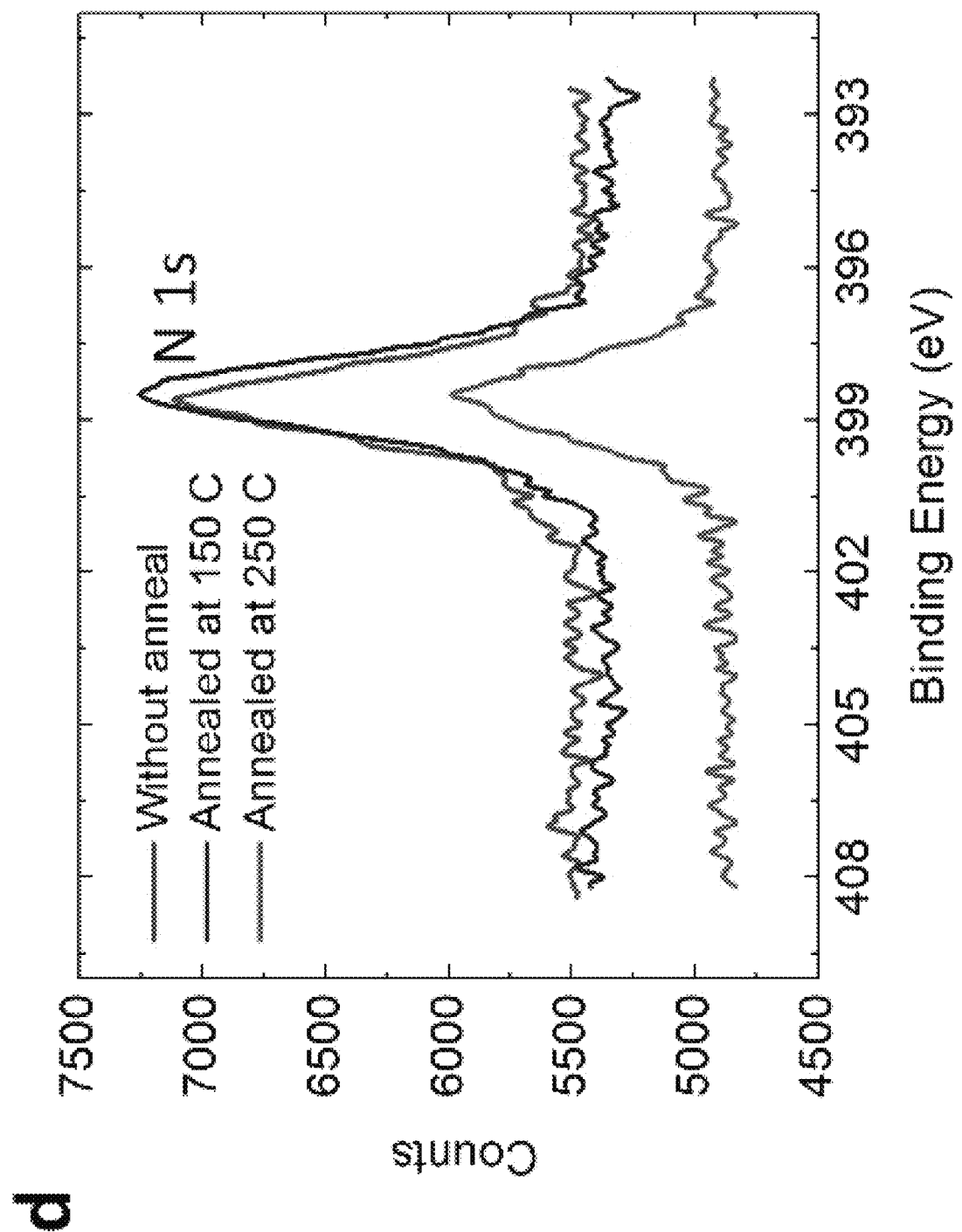
Figure 11A:
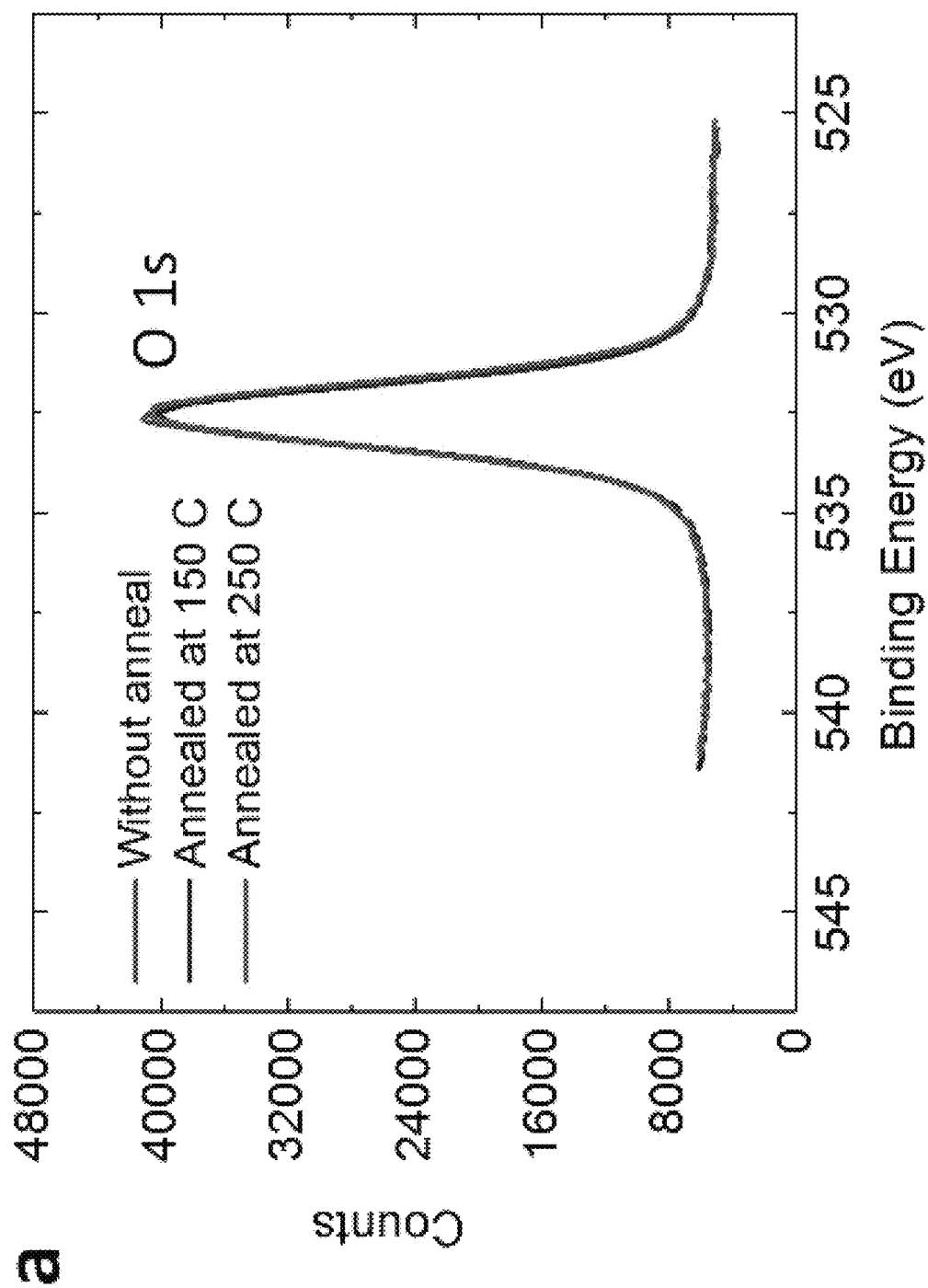
Figure 11B:
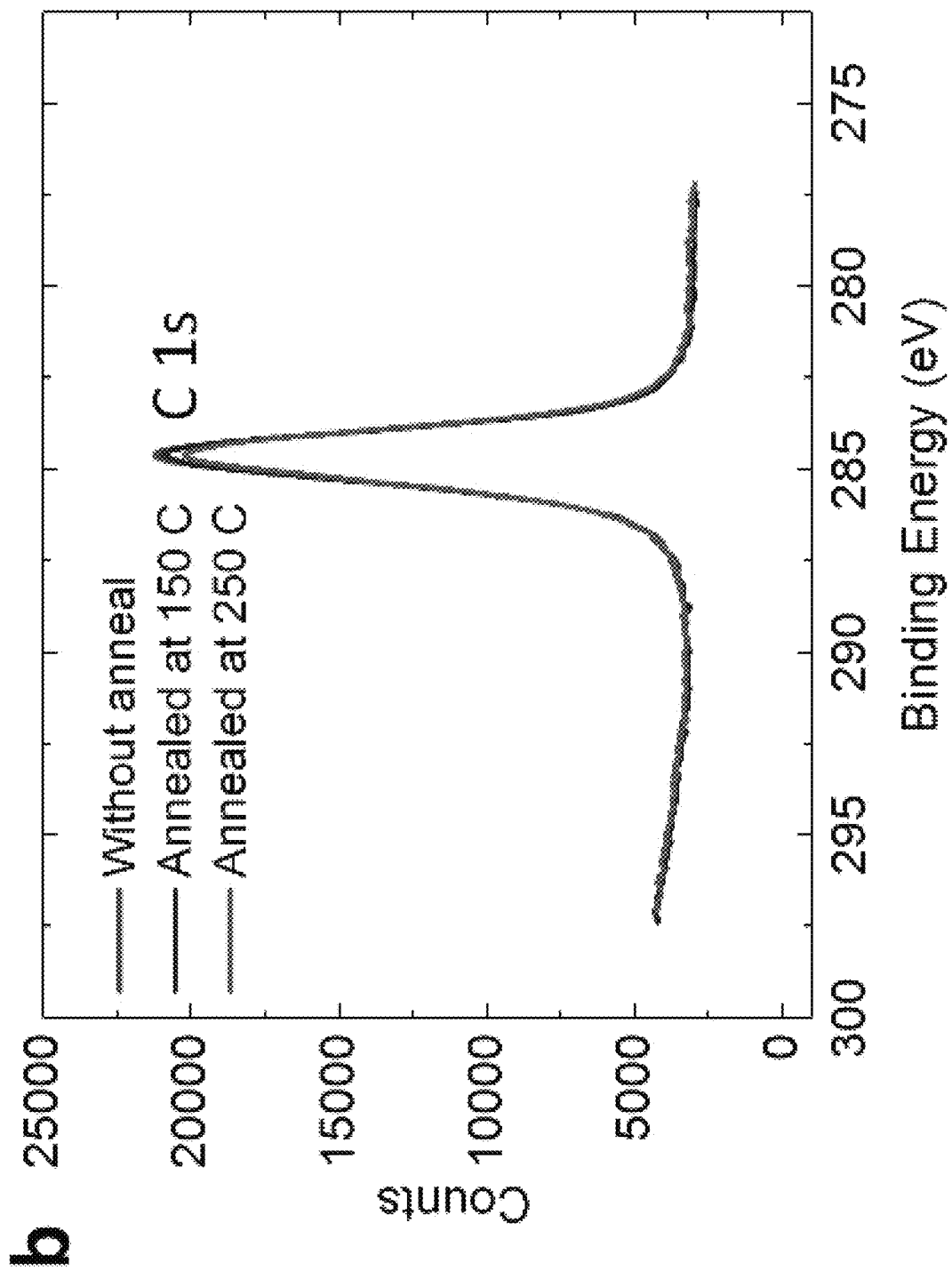
Figure 11C:
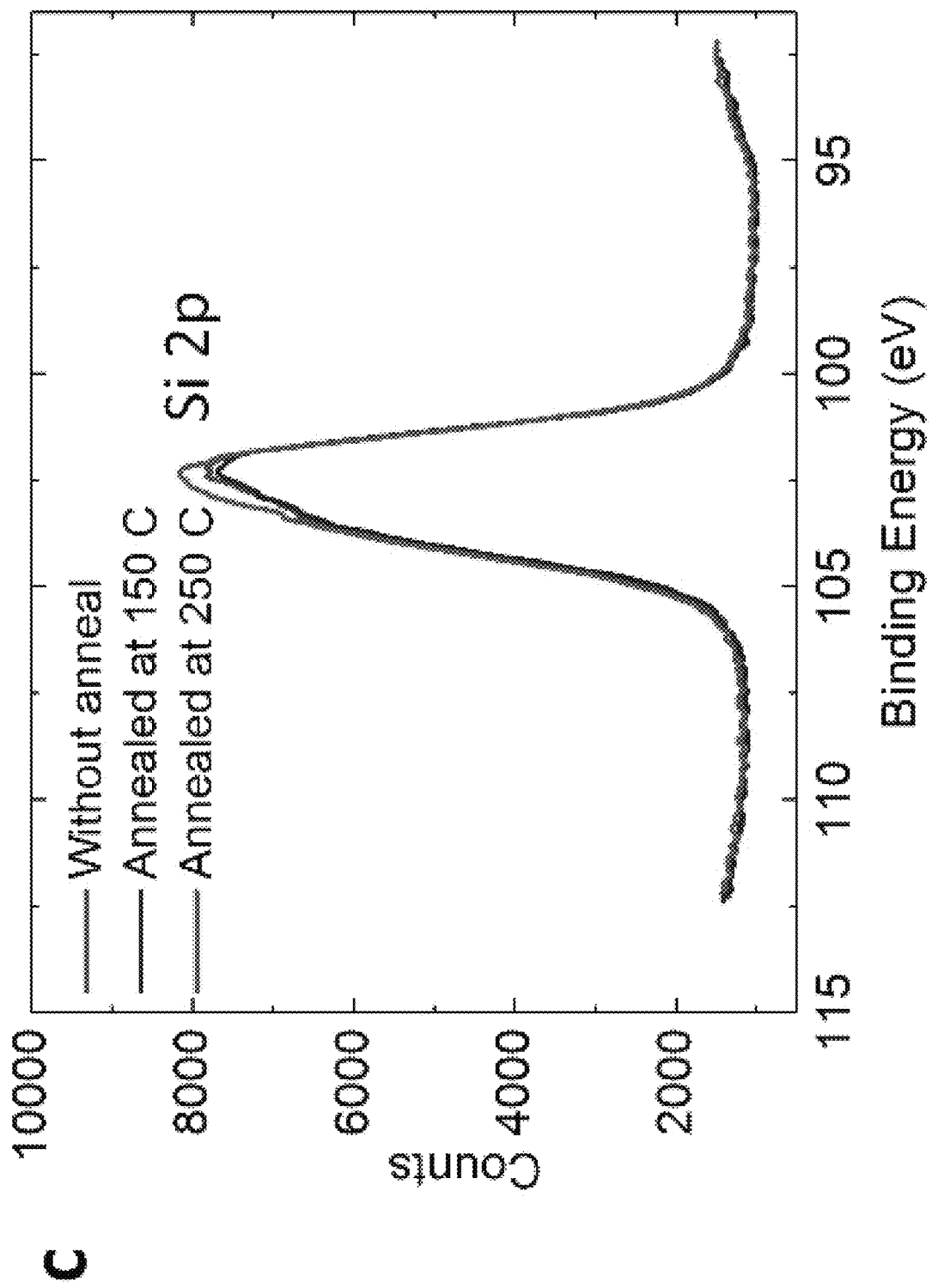
Figure 11D:
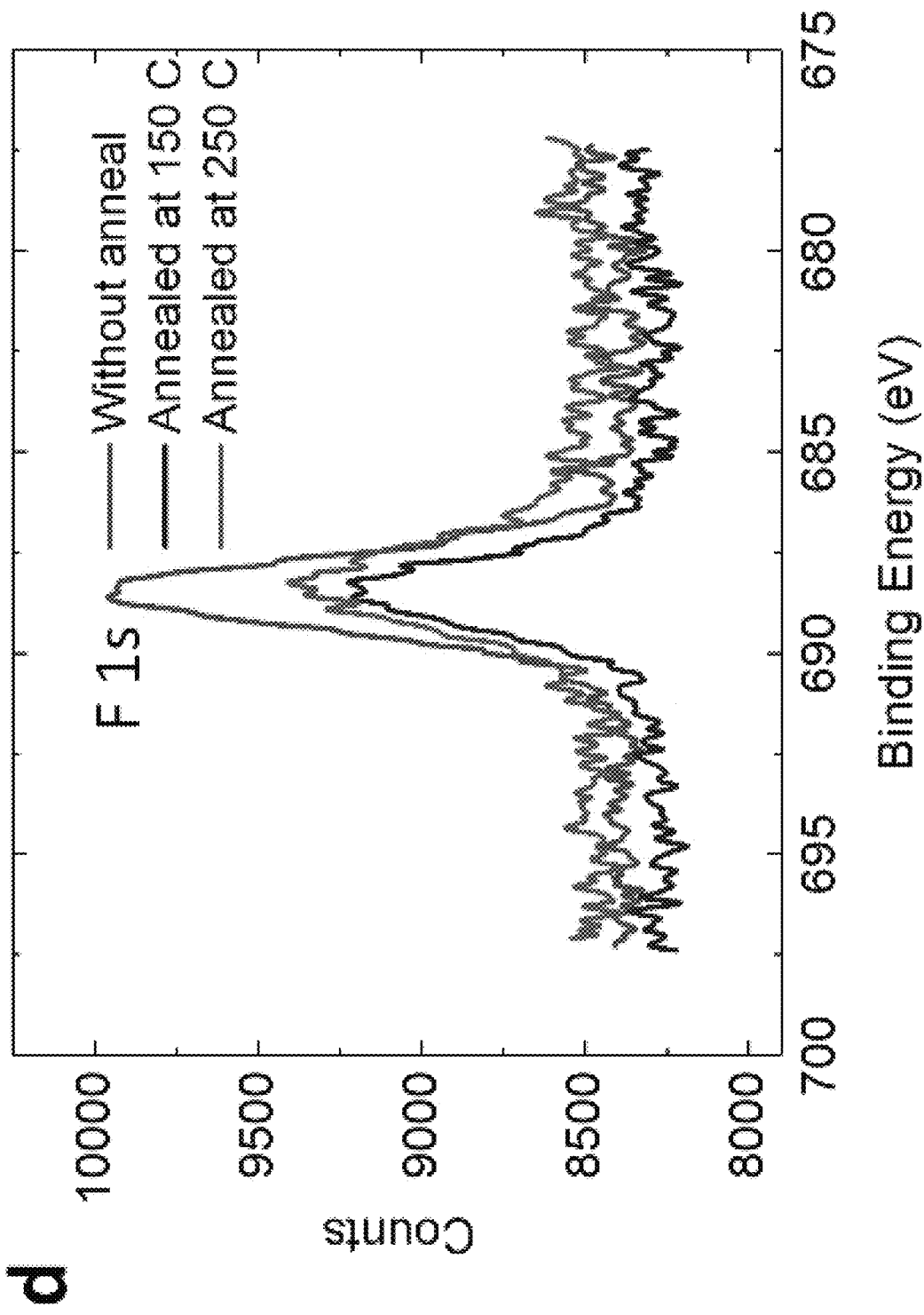

Step 210: Create a high resolution negative mold of an end pattern. Any number of conventional techniques can be used to create a high-resolution microscale mold. As indicated, one way to well-known microlithographic techniques resulting in a flexible PDMS substrate (ref no. 212) with high resolution negative of the pattern formed therein. See for example FIGS. 9A-B.

1. Create High Resolution Nanomaterial Pattern in Mold by D2SP Technique

A variety of nanomaterials that are functional for these types of purposes are possible. Graphene is one non-limiting example (ref. no. 214). It is highlighted because of its properties, as discussed in more detail herein. But it is to be understood the invention is not necessarily limited to the specific nanomaterials mentioned. As will be appreciated by those skilled in the art, nanomaterials can comprise a wide variety of particles, including but not necessarily limited to at least many of the examples given in the definitions of nanomaterials at ISO/TS 80004 and the European Commission at http://ec.europa.eu/environment/chemicals/nanotech/.

As indicated in FIG. 23, in one non-limiting example of creating a negative of a high-resolution pattern, a dispersion or suspension of such nanomaterials is applied to a mold by drop-casting over the top of the mold, covering both the unpatterned surfaces as well as the negative pattern. As is explained further herein, one parameter the designer will work with is the volume of the dispersion/suspension first placed on the mold. In at least one embodiment, the volume is selected relative to the negative pattern to result in a thin layer that basically coats the mold but does not fill the negative features up to the top of the mold. This allows the beneficial use of, in one example, a D2SP technique (ref. no. 216) which is explained further herein. Basically, D2SP repeats a plurality of times or cycles of:

1. Drop cast a pre-determined volume of the suspension on the mold to conform across the mold but not fill the negative portions to the top, as well as leave a relatively thin conformal layer once reduced to the thin film. See, e.g., FIG. 3C.
2. Use a cleaning adhesive tape with adhesive properties selected to effectively clean the thin film from non-patterned mold surfaces but leave intact the thin film formed in the negative features of the mold.
3. Repeat, if needed, sub-steps 1 and 2 immediately above to:
   a. drop cast another volume of dispersion on the mold to then
   b. add another thin layer to the one existing in the negative features to fill up more of the negative features of the mold, while
   c. again removing the thin film from the nonpatterned surfaces of the mold.
4. Repeat, if needed, sub-steps 1 and 2 to build up additional negative features layers and clean nonpatterned surfaces. In one non-limiting example, the repeats could be one or more in number depending on need or desire.

Modification, tuning, or configuration of the nanomaterial can take place either all together or just selected portions (ref. no. 218). As will be appreciated by those skilled in the art, one modification of nanomaterials like graphene is annealing. Material properties of graphene (e.g. electroresistive) can be altered with heating. This allows tuning of such properties as needed or desired for a specific application. As will further be appreciated by those skilled in the art, such modification (including annealing) can be during fabrication or could be at the intended use site (point of care). For example, annealing can be by ambient heating. Alternatively, a laser could be directed onto minute selected portions of the material. It is possible to mount the sensor 10 in place on the surface to be investigated, and then anneal it to tune its properties (at the point of care or final use location) with appropriate manipulate of a heating laser or other annealing source.

One post-transfer option is as follows. Annealing of the target tape with transferred pattern (ref no. 218). Thermal annealing (or other annealing techniques), in a manner that does not materially affect the needed functions of the target tape, can promote such things as better adherence of the pattern to the tape. For at least graphene, it can also alter or tune (by control of the annealing in terms of temperature, time, etc.) the electrical or other properties of graphene. This can be advantageous in the performance of the pattern for certain functions. A non-limiting example of such tuning by annealing graphene in a pattern can be found at S. Das, Q. Nian, A. Cargill, J. Hondred, S. Ding, M. Saei, G. Cheng, and J. Claussen, "3D nanostructured inkjet printed graphene via UV-pulsed laser irradiation enables paper-based electronics and electrochemical devices", *Nanoscale*, vol. 8, no. 35, pp. 15870-15879, 2016, which is incorporated by reference herein. As will be appreciated by those skilled in the art, other annealing techniques can be used. Non-limiting examples include enclosures with regulated temperature, more point-source heating, or other.

2. Transfer the High-Resolution Nanomaterial Pattern to Target Tape by ST

As indicated in FIG. 23, in one specific example of a substrate to which the nanomaterial pattern can be transferred, a second adhesive tape is then placed onto the mold. The plurality of layers built up in the high-resolution negative in the mold, the clean mold unpatterned surfaces, and the predesigned adhesive properties of the target tape adhesive relative the nanomaterial pattern, allow an ST (stick and transfer) step (ref no. 220) to promote (a) removal of at least substantially all the nanomaterial pattern from the mold, (b) kept it intact with high resolution to the negative of the mold, and (c) adhere it intact to the target tape. As further indicated in FIG. 23, post-transfer options are possible.

It is to be understood, in the case of graphene, self-adherence by the bond force of graphene molecules to each other, and of layers of graphene to each other, are generally stronger than the adhesion force between graphene and at least a PDMS mold surface, that adhesive such as found in commercially-available Scotch® brand tape would both adhere to graphene and pull at least most of the graphene in the PDMS negative mold out of the negative mold on simple peeling or separating the tape from the mold, and keep the graphene intact and substantially in high resolution replicate of the high-resolution negative mold. As will be appreciated by those skilled in the art, a number of other commercially-available adhesive tapes exist and at least several would likely work at least similarly effectively. That includes not only polyimide tapes, but other others. Non-limiting examples include fabric or web-based tapes (e.g. athletic or medical tapes or patches) or metallized tapes or other plastic tapes, whether air/gas permeable or not, or stretchable/non-stretchable or not.

Still further, a designer could select a number of other substrates and an adhesive and create a desired combination for use with embodiments of the invention if not commercially-available or if simply desired. Also, as will be appreciated and is discussed herein, the substrate does not have to be adhesive tape, tape, flexible, or otherwise the attributes of adhesive tape. It could be less flexible (or inflexible), thicker (or thinner), wider (or narrower), or otherwise different from at least commercially-available Scotch® brand household polyimide tape. Non-limiting characteristics the designer could include are air/gas permeable or impermeable, stretchable/non-stretchable, transparent/semitransparent tapes.

In the case of an adhesive substrate, a liner or release layer (ref. no. 222) could be added to the pattern-side of the target tape after the pattern has been transferred to protect both the pattern and the exposed adhesive on that side. As indicated herein, the resulting target tape is essentially a flexible substrate tape with nanomaterial pattern that can be used as a flexible, conformal assembly mounted to a target surface or material such as fabric, skin, or plant body (e.g., leaf, stalk, root, etc). The exposed adhesive can be used to help the mounting. Additional mounting/installation techniques can also be used.

As indicated, the techniques can be implemented in a large-scale process (ref no. 224). The mold can be scaled or replicated serially on a first roll and the D2SP technique automated on a continuous basis. A second roll could use the ST technique to remove the positive clean and built-up patterns from the first roll on a continuous basis. The second roll can then be rolled up (alone or with a liner or release sheet, whether annealed or not, and in bulk available for further use). Other scalable, mass production techniques are possible.

As will be appreciated, the foregoing techniques meet at least one or more objects or aspects of the invention by presenting simple, low-cost (no expensive equipment) fabrication of high resolution micro-scale or smaller patterns on a variety of substrates with a variety of patternable materials. Spatial resolution and thickness control present a variety of possible beneficial applications of the patterned substrates, including but not limited to, flexible, conformal, wearable patterned adhesive tapes or patches.

3. Remove Desired Parts of Target Tape and Create Electrical Circuit

As indicated in FIG. 23, at some point MEMS or other techniques can be used to dice, cut, or otherwise select and separate the desired portions of the target tape or other substrate (ref no. 230) and create, as a non-limiting example, a sensor circuit (ref. no. 232). Examples are discussed in the specific embodiments below.

4. Mount Selected Portion(s) of Target Tape to End Target

As will be appreciated, in the case of adhesive tape, the target tape is essentially a flexible substrate with functional nanomaterial patterning capable of use as a variety of sensors by the appropriate configuration with leads, orientation, etc., and then application to the end target (ref. no. 240). The end target can be any of a variety of surfaces, including non-planar rigid inanimate surfaces or skin of humans or other animals, or plant tissue (see, e.g., FIGS. 5A-F, 6A-H, 7A-F, 8A-E, 15, and 24A-C). The end target itself can be flexible, resilient (to at least some degree), and even foldable. It will be appreciated, however, that the techniques can be applied in analogous ways to other substrates with the use of some mechanism on the substrate to pull the material for the pattern out of its negative mold in a manner that transfers to the substrate with at least on the same order of resolution as the negative pattern. In one example, the mechanism could be adhesive added to a substrate surface.

It can be seen that the generalized example meets one or more of the stated objects of the invention and that it can take a variety of configurations. Further understanding will be gained by the more specific examples that follow below.

As will be appreciated, the steps of FIG. 23 can be adjusted or substituted according to one or more aspects of the invention and the examples of the embodiments disclosed herein. A few examples will be discussed herein.

For additional understanding, non-limiting examples of aspects according to the invention will now be described. The first example will be in the context of a substrate comprised of a commercially-available adhesive tape and the patterning comprising graphene. As indicated herein, these are non-limiting examples. Additional examples and discussions below will discuss some possible variations.

C. Specific Embodiment 1

High-Resolution Patterning and Transferring of Graphene-Based Nanomaterials onto Tape Toward Roll-to-Roll Production of Tape-Based Wearable Sensors

[This specific example is taken from Oren, S., et al., High-Resolution Patterning and Transferring of Graphene-Based Nanomaterials onto Tape toward Roll-to-Roll Production of Tape-Based Wearable Sensors, Adv. Mater, Technol. 2017, 2, 170023 (14 pages), which is incorporated herein in its entirety.]

This exemplary embodiment is a simple and versatile method for patterning and transferring graphene-based nanomaterials onto various types of tape to realize flexible microscale sensors. The method involves drop-casting a graphene film on a prepatterned polydimethylsiloxane (PDMS) surface containing negative features by graphene suspensions, applying Scotch tape to remove the excess graphene from the nonpatterned areas of the PDMS surface, and then transferring the patterned graphene from the inside of the negative features at the PDMS surface onto a target tape. The feature size of transferred graphene patterns on the final tape is as small as a few micrometers. This method is easy to implement, but does not require the use of expensive equipment, except for needing a PDMS substrate containing negative features. This method has a high versatility in producing micropatterns of graphene-based nanomaterials on different types of adhesive tape. For the purpose of application demonstration, flexible mechanical sensors and sensor arrays, smart gloves, and plant leaf sensors on tapes to realize real-time monitoring of important signals indicating human motion and plant water transport behavior have been developed. This technology will open a new route for low-cost, scalable, and roll-to-roll production of graphene-based sensors on tape.

1. Introduction

Flexible plastic substrates (e.g., polyethylene terephthalate, polyimide, and polydimethylsiloxane or PDMS) [1-6] and other nonconventional substrates (e.g., paper, tape, and cloth) [7-10] have been widely utilized as the base materials of flexible electronic devices. Conductive nanomaterials, such as carbon nanotubes, metal oxide nanowires, and graphene, have also attracted considerable attention as functional materials for applications ranging from transistors, to sensors, to energy harvesting and storage devices. [11-22] Among these conductive nanomaterials, graphene plays a key role in producing next-generation sensors owing to its unique properties, including atomic thickness, large surface area, fast electron mobility, good piezoresistivity, and high mechanical flexibility. [23-27] As a result, integrations between flexible substrate materials and graphene-based nanomaterials have led to a variety of sensors and other electronic devices through development of novel fabrication processes, advancing emerging and significant fields such as real-time motion tracking, [28] structural and human health monitoring, [29-31] electronic skin sensing, [32-36] and humanized robotic manipulation. [37] It is well known that repeated mechanical exfoliation to peel single- or few-layer graphene from bulk graphite using sticky tape and transfer it to another surface is rather uncontrollable in terms of the number of graphene layers, location, and size of the peeled graphene. [38] Recently, graphene film electrodes at centimeter scale have been fabricated by peeling tape from a commercial graphite foil for the detection of glucose, [39] but the obtained electrodes did not have well-defined shapes or control over thickness. Physically rubbed graphene electrodes have also been produced by directly placing solid-state graphene powders at a channeled adhesive surface and then rubbing against the surface [40]. The resulting graphene patterns, however, have poor feature resolution. Photolithography-based microfabrication for graphene patterning [41-49] is relatively complex and requires multiple steps such as film deposition, lithography, and etching. Recently, various interesting methods have been developed for patterning and transferring graphene-based materials onto different substrates. For example, laser printing of graphene has been studied with variable laser energy, spot size, and pulse duration [50-54]. This method, however, requires sophisticated lasers and is limited to producing patterns with minimum feature size of several tens of micrometers. An ink-jet printing method has also produced patterns of reduced graphene oxide (rGO), but resolution is poor and, for practical applications, additional laser processing is required to improve electrical conductivity of rGO. [55] A transfer printing method involves first creating graphene patterns on an initial substrate, and then utilizing a stamping process to transfer them onto a final substrate. [56] Micro transfer molding is based on filling the carved patterns of a stamp emplaced on top of a target substrate with graphene-based suspensions, followed by vacuum drying and removing the stamp from the final substrate. [57] Both the transfer printing and molding methods require a special care to modify the surface properties of the device substrates and functional materials. In addition, most existing graphene-based sensors cannot be easily installed onto the irregular surfaces of the sensed objects so, despite the efforts made, many problems remain unsolved before a large-scale, cost-effective graphene patterning method with high feature resolution and process simplicity can be realized.

This embodiment is a simple, high-resolution, and scalable graphene patterning and transferring method toward roll-to-roll production of flexible graphene sensors. This method involves (i) creating graphene patterns inside prepatterned negative features at the surface of a polydimethylsiloxane (PDMS) substrate using a unique "Drop Cast-Dry-Stick-Peel" (D2SP) method, and subsequently (ii) transferring the resulting graphene patterns onto a final sticky tape via an easy-to-implement "Stick-and-Transfer" (ST) process. The feature size of the transferred graphene structure on the final tape can be as small as a few micrometers. This method does not require the use of any expensive equipment, except for needing a PDMS substrate containing negative features. The versatility of this approach is demonstrated by producing complex graphene and rGO micropatterns onto different tapes commercially available (e.g., polyimide, Scotch, 3M electrically conductive, and aluminum foil adhesive tapes). Furthermore, tape-based flexible graphene pressure and strain sensors, sensor-enabled smart gloves, and plant leaf humidity sensors are realized to interact with humans and plants for real-time monitoring of important signals. We have demonstrated that smart gloves with multiple strain and pressure sensors allow real-time tracking of finger motion behavior during capturing a moving object, while graphene-based humidity sensors can be made to adhere to leaf surfaces to monitor water movement within plants upon irrigation. These sensors are flexible enough to highly conform to various irregular shapes of the sensed objects. The patterning and transferring method presented outperforms many other counterpart approaches in terms of pattern spatial resolution, thickness control, process simplicity, and diversity with respect to functional materials and pattern geometries.

Figure 1A:
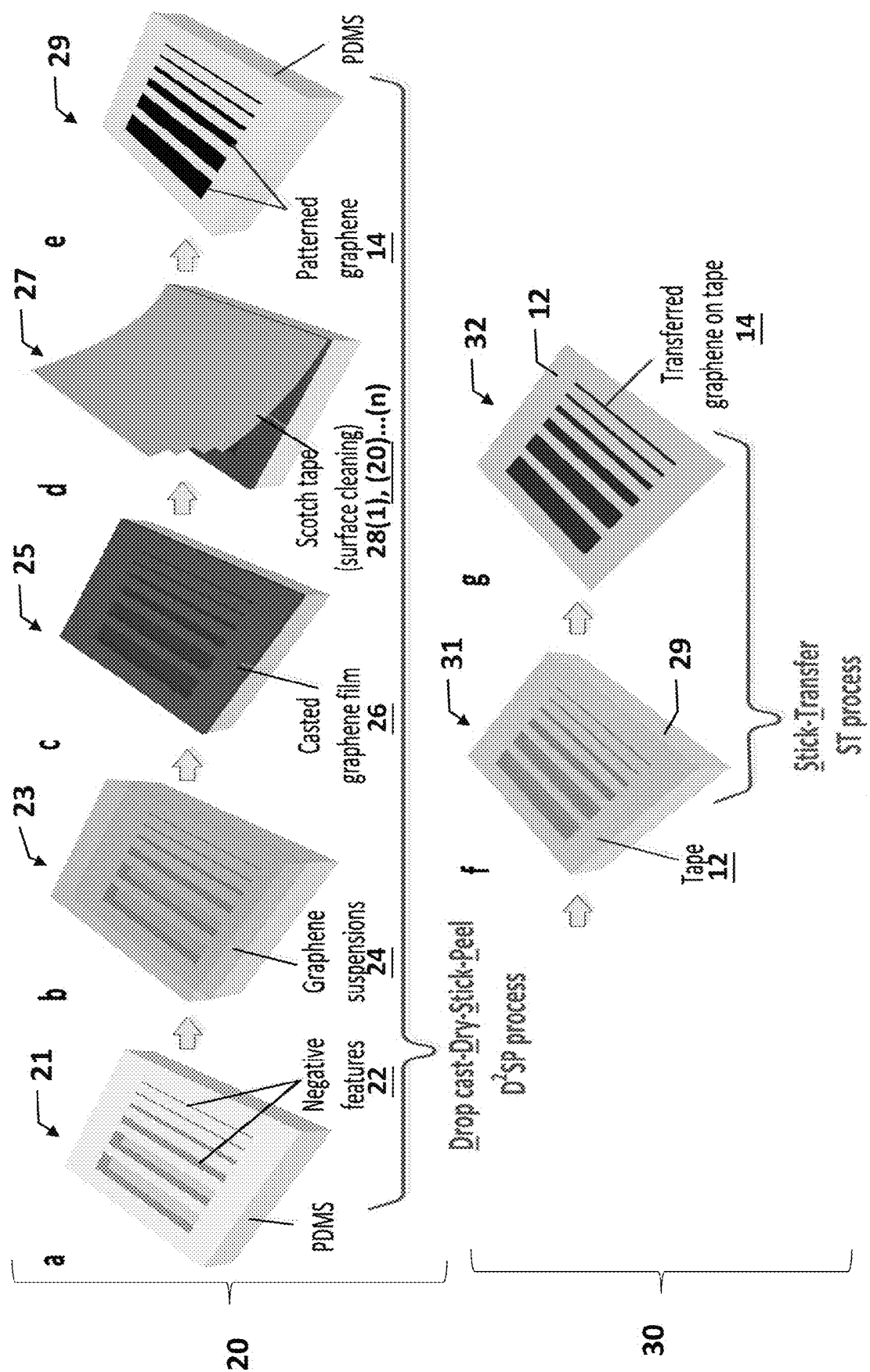
Figure 1B:
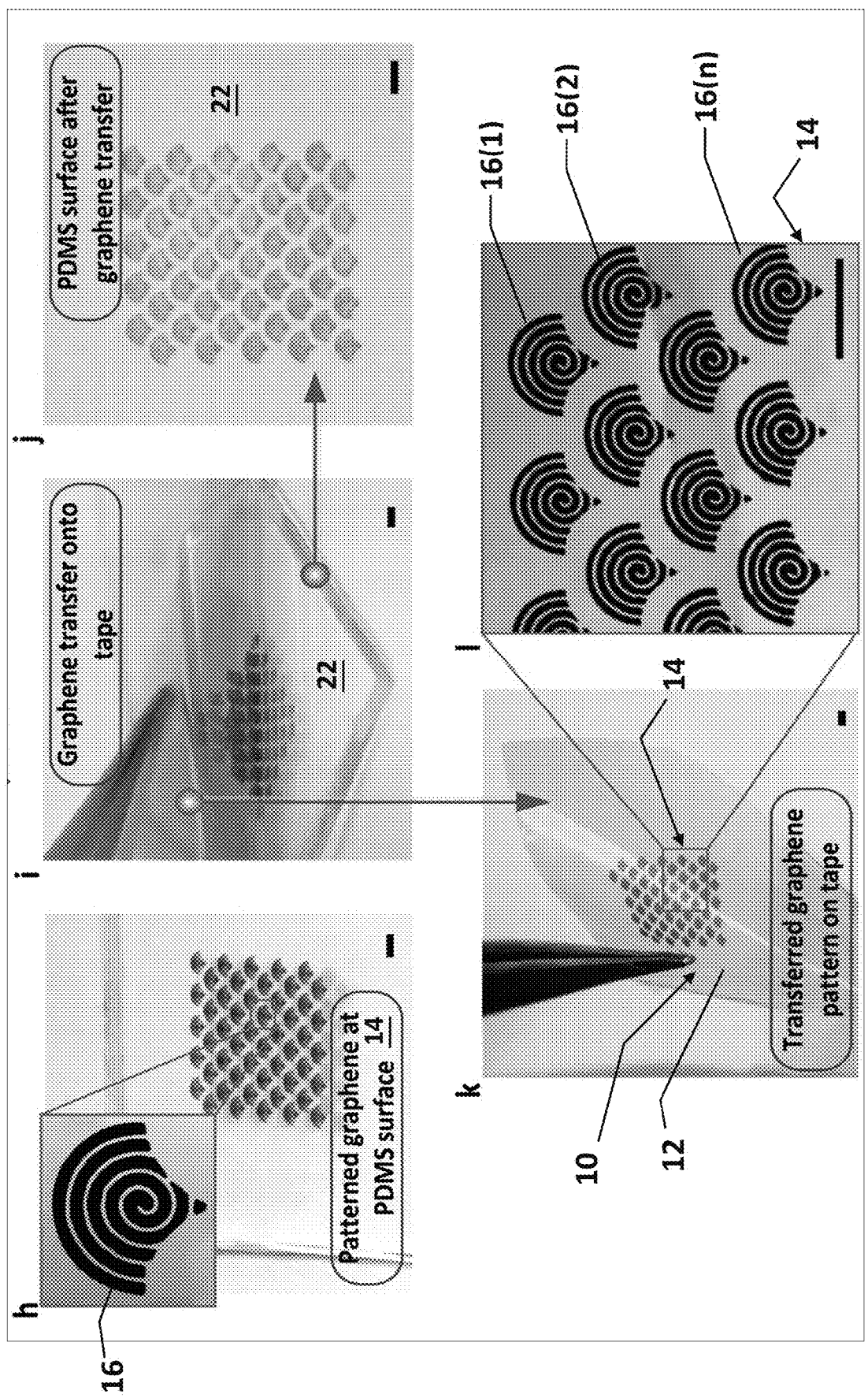

The main procedures for forming graphene patterns on the tape surface are illustrated in FIGS. 1A-B. Briefly, a master Si mold with positive patterns made of SU-8 photoresist was first formed on the surface of a silicon wafer (see, e.g., FIG. 9 at ref. nos. 92, 93, 94, 95), and negative patterns 22 were then formed on a PDMS substrate (see ref. no. 21) from the Si mold 94 via soft lithography (FIG. 1A, subpart a). Here, the "negative" patterns or features 22 refer to the "channels" or cut out areas at the PDMS surface. Subsequently, aqueous suspensions 24 of graphene nano-platelets were loaded (see ref. no. 23) onto the PDMS surface (FIG. 1A, subpart b). After drying on a hotplate in air, a thin graphene film 26 was formed (see ref. no. 25), covering the entire PDMS surface (FIG. 1A, subpart c) (both the top surface of the PDMS 21 and into negative features 22). Next, Scotch tape 28 was manually applied and stick to the top surface of the PDMS 21, and then peeled excess graphene from the nonpatterned areas on that surface. This stick-and-peel process was repeated (see ref. no. 27; with one or more pieces of Scotch tape as needed) to ensure complete removal of the unwanted graphene from the top surface (FIG. 1A, subpart d), while the graphene inside the PDMS negative patterns 22 remained intact because it was set below the top surface. Therefore, the D2SP process was completed, resulting in the graphene structures 14 inside the negative patterns 22 on the PDMS surface (see ref no. 29 at FIG. 1A, subpart e). After that, transfer of the formed graphene patterns 14 onto a final target tape 12 was implemented by manually applying and pressing the target tape 12 (see also ref no. 31), and then peeling it from the PDMS surface (see ref no. 32, FIG. 1A, subparts f, g). The ST process was thus completed and the microscale graphene patterns 14 were formed onto the surface of the final tape. FIG. 1B, subparts h-l display the images for the main procedures of the D2SP and ST processes. The details of fabrication are described in the Experimental Section, infra.

As illustrated in FIG. 1B, subparts h-l, whatever the negative pattern 22 is in the PDMS is filled by the nanomaterials, excess/undesired nanomaterials are removed with D2SP, and ST removes a positive of the negative features 22 onto the target tape 12. This transferred pattern is generally referred at ref. no. 14. Pattern 14 could comprise a single feature (e.g. a line segment, rectangle (solid or outline), circle (solid or outline), etc.), but as indicated in FIGS. 1A-B, pattern 14 can be complex shapes or combinations of shapes, and further, can be a plurality of distinct shapes, whether identical to each other (see ref. nos. 16(1), 16(2), . . . , 16(n) or different. The designer can create the negative mold as needed or desired for any of the above.

Essentially, the tape-based graphene patterning and transfer technique utilizes the work of adhesion $W_{A-B}$ at the interface between two contacting materials A and B as determined by their surface energies, [59, 60] with $W_{A-B}$ given by [61]

$$W_{A-B} = 4\left(\frac{\gamma_A^d \gamma_B^d}{\gamma_A^d + \gamma_B^d} + \frac{\gamma_A^p \gamma_B^p}{\gamma_A^p + \gamma_B^p}\right) \quad (1)$$

where $\gamma^d$ and $\gamma^p$ correspond to the dispersion and polar components of surface energy ($\gamma = \gamma^d + \gamma^p$). Table S1 (Supporting Information) provides the surface energies of the materials used in this work [68-70] and the calculated values of $W_{graphene-PDMS}$ at the interfaces between graphene and PDMS and $W_{graphene-tape}$ between graphene and tape. The fact that $W_{graphene-tape} > W_{graphene-PDMS}$ for different types of tape makes it possible to remove the excess graphene from the PDMS top surface using the cleaning Scotch tape during the D2SP process and transfer the patterned graphene onto the target tape during the ST process. See the Supporting Information for the values of $W_{A-B}$ for different material combinations.

2. Results and Discussion

2.1. Microscale Patterning and Transferring

Figure 2A:
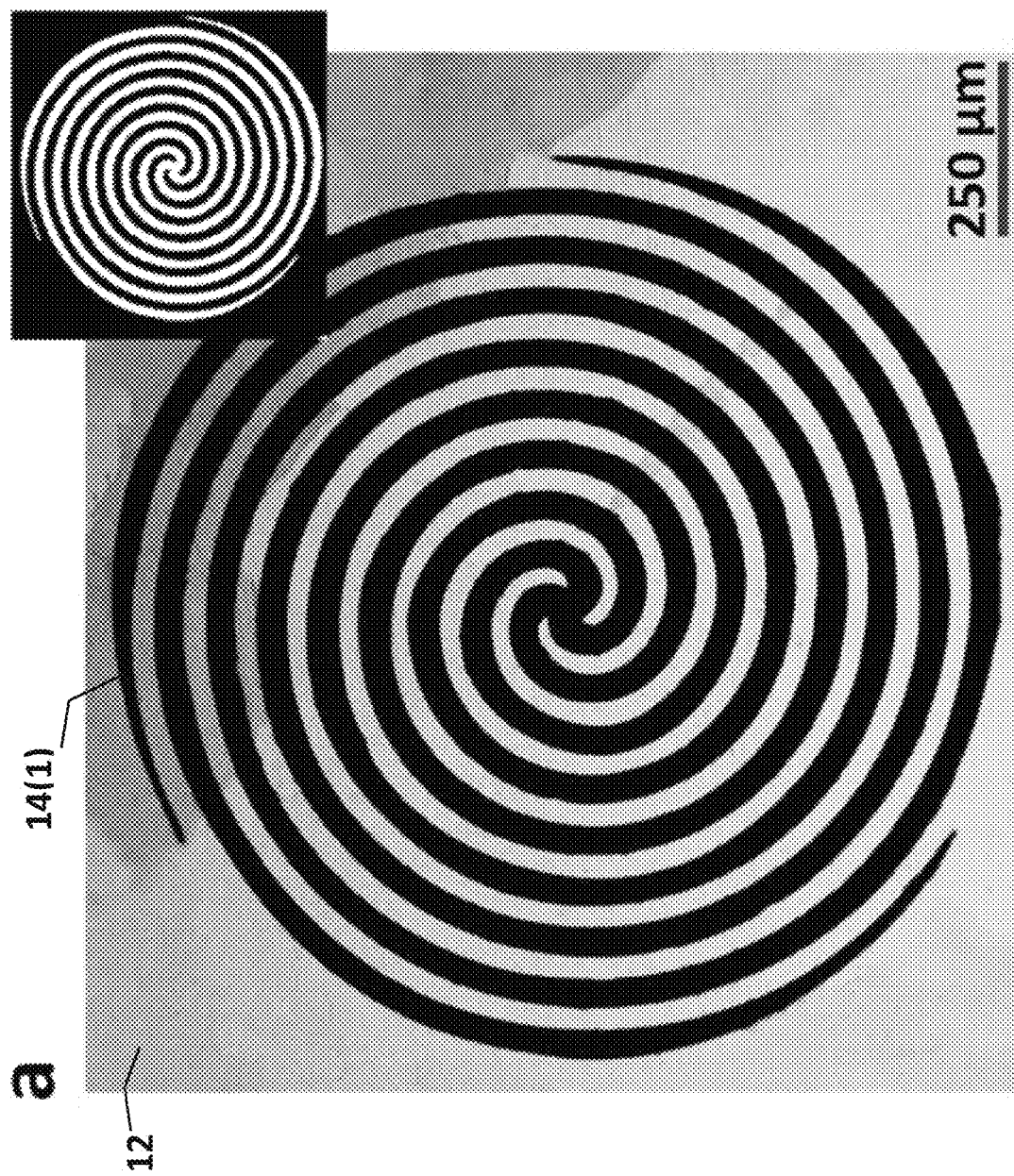
Figure 2B:
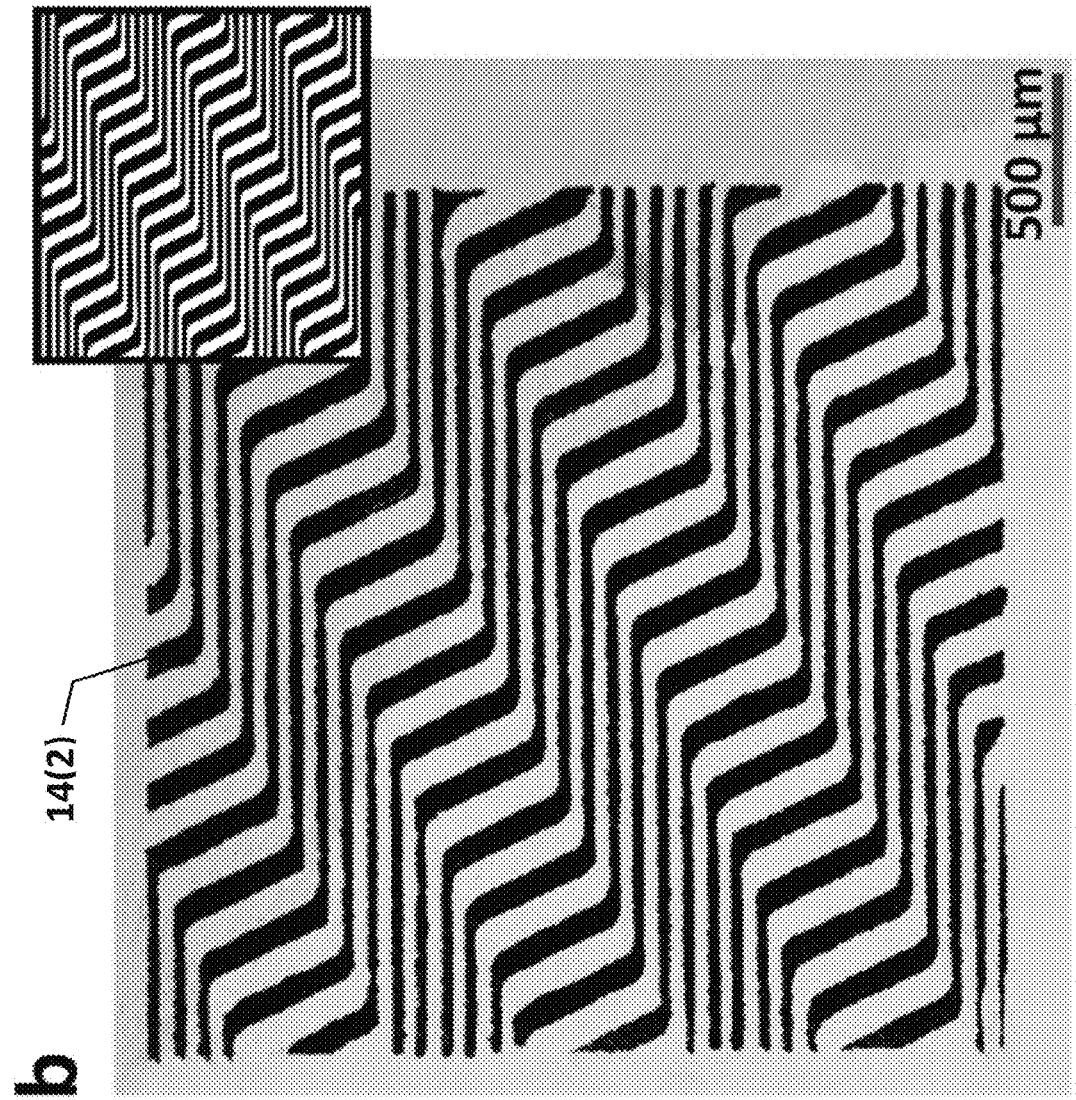
Figure 2C:
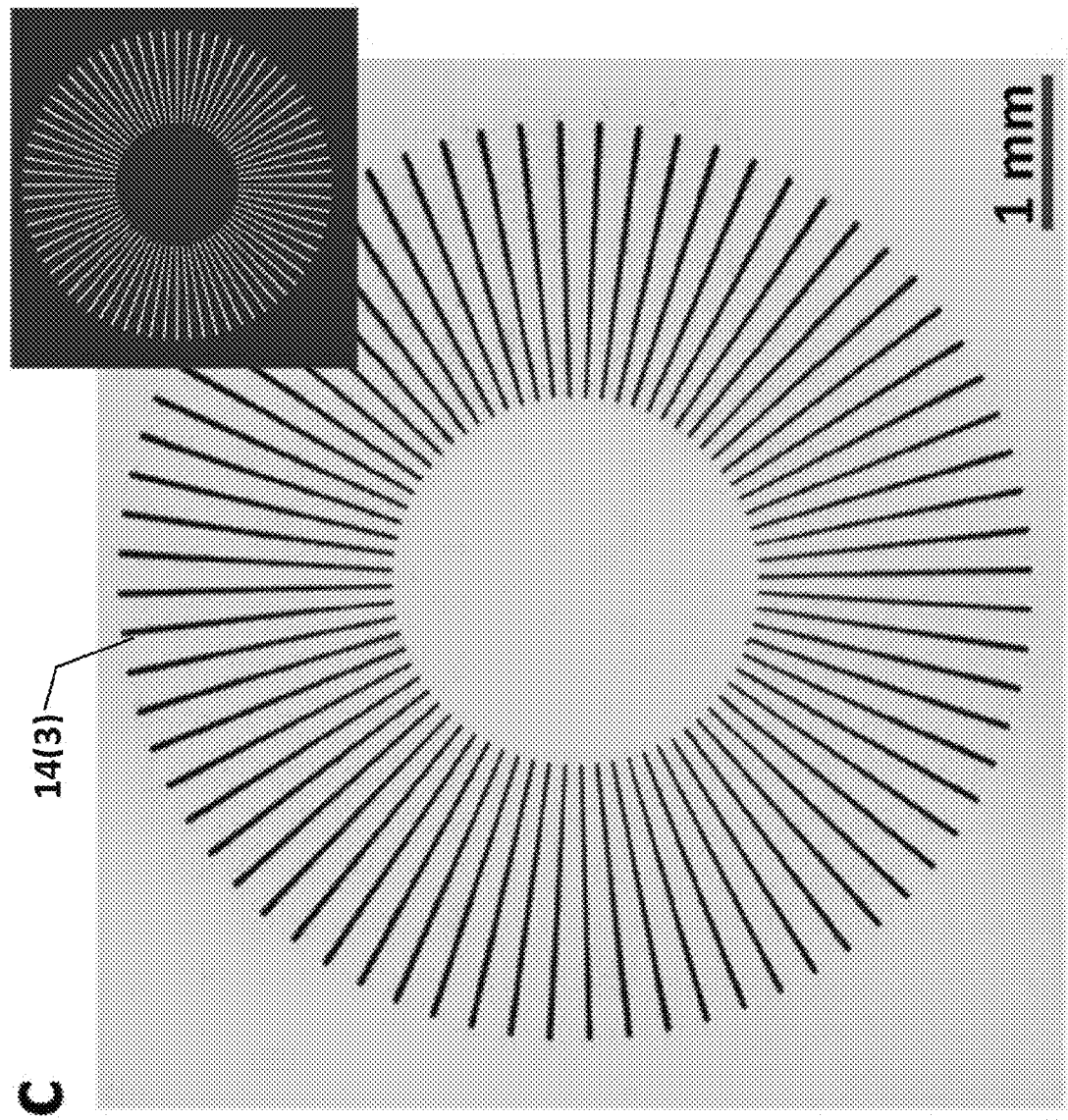
Figure 2D:
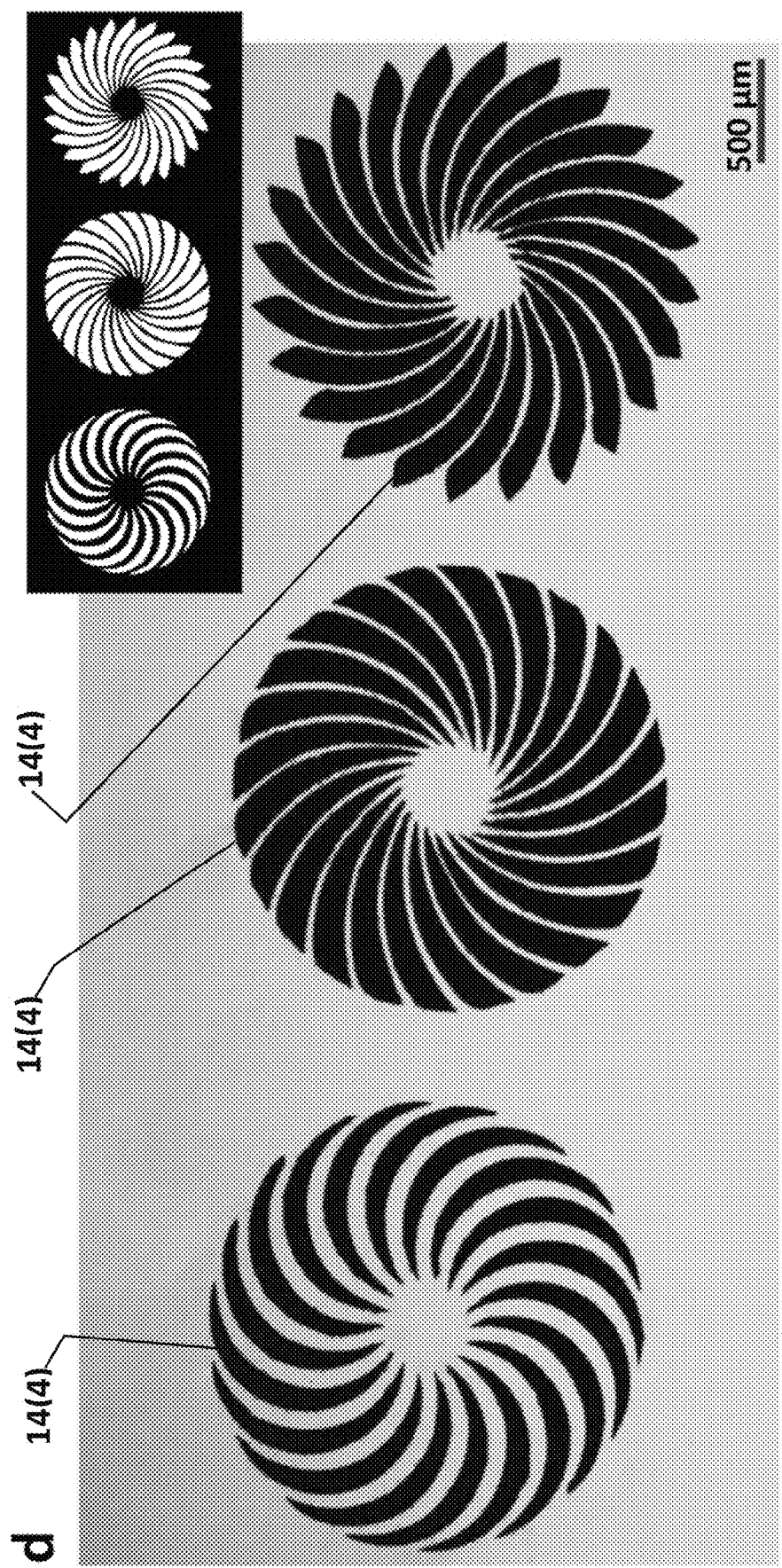
Figure 2E:
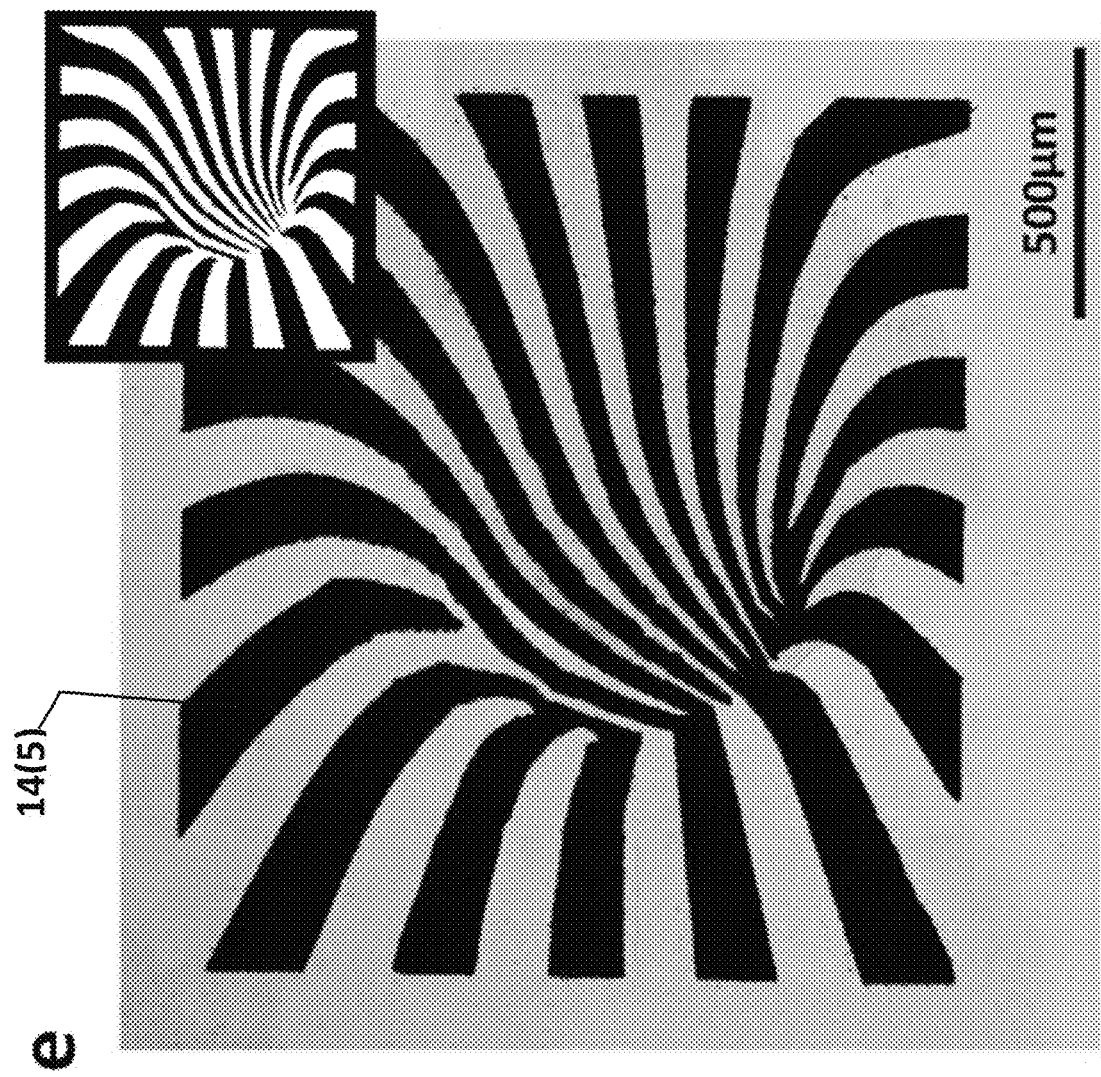
Figure 2F:
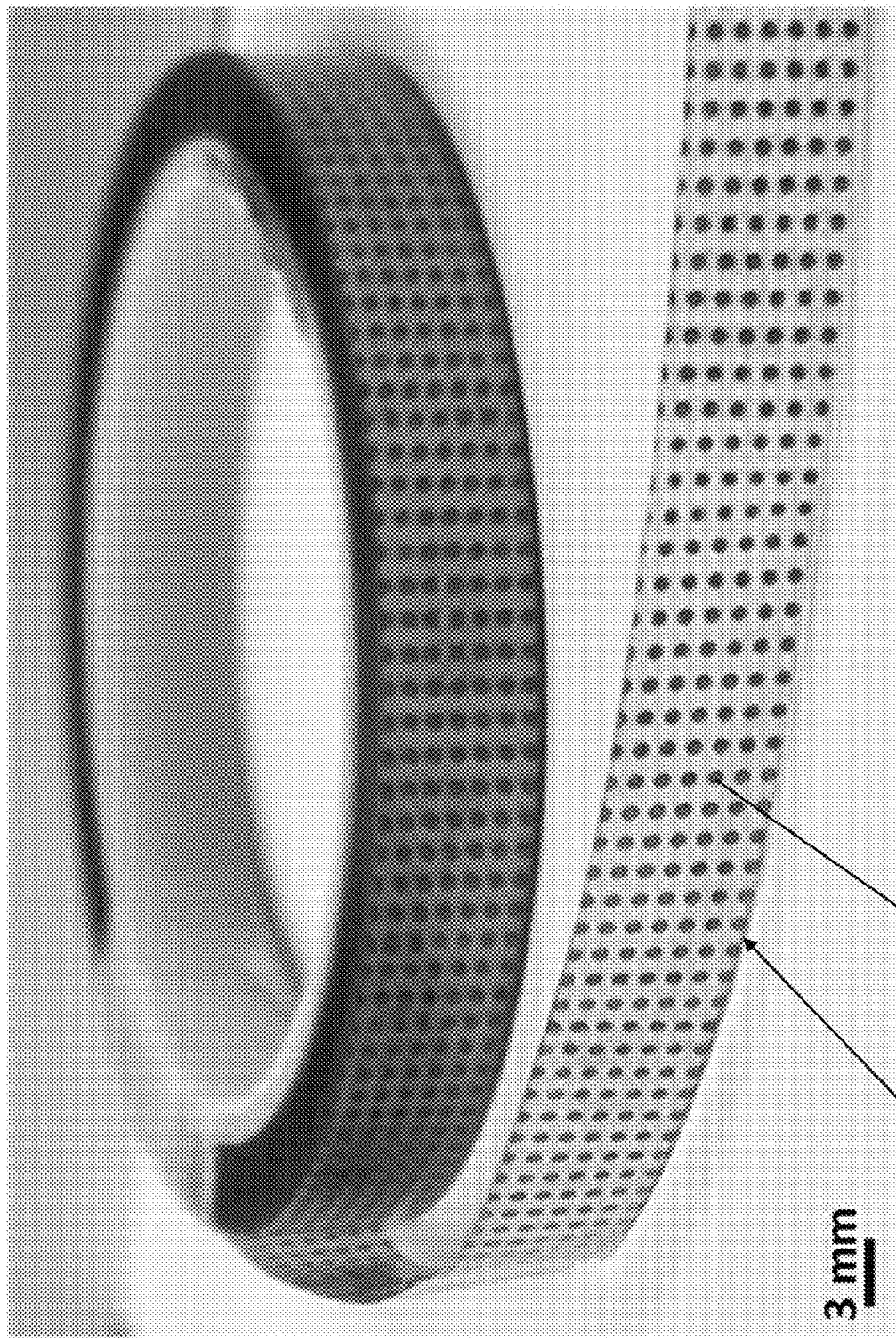
Figure 2G:
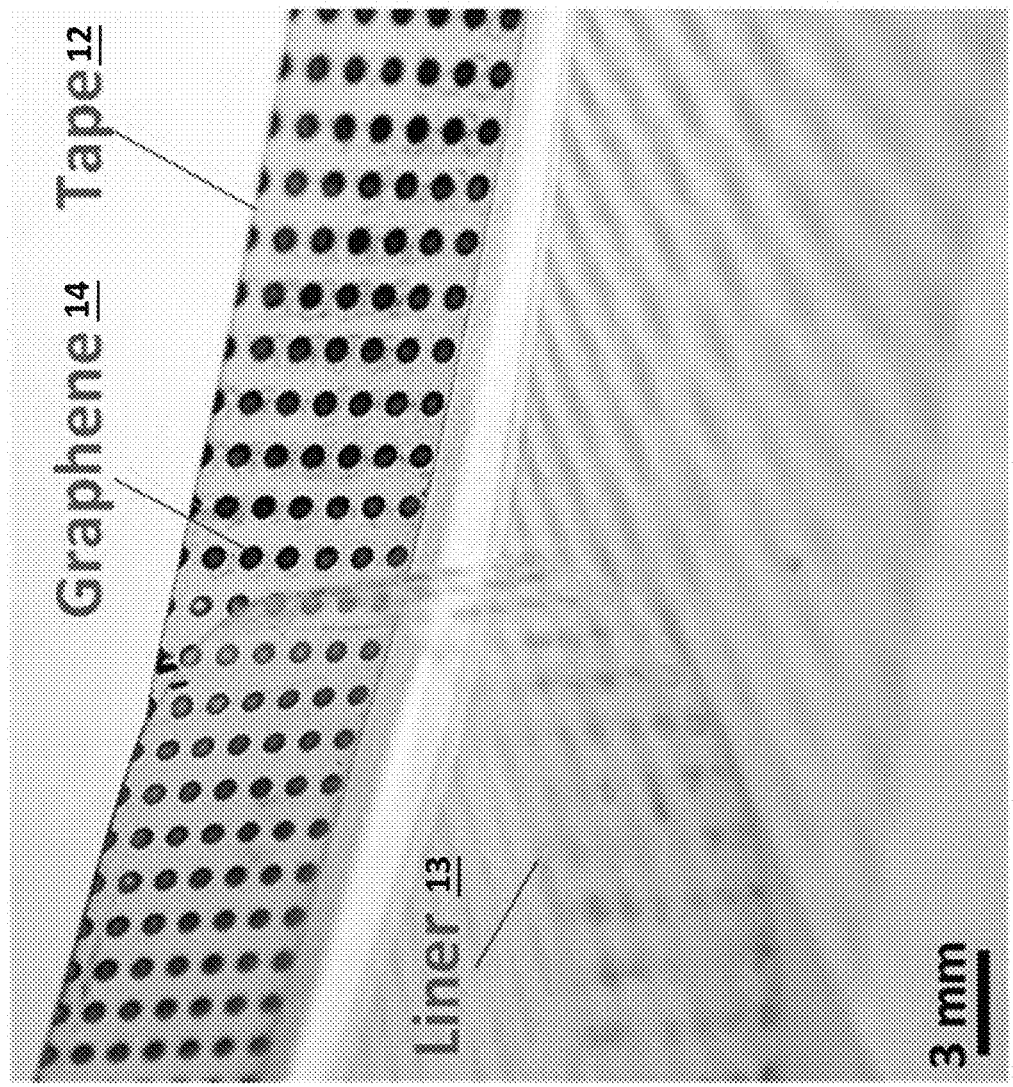
Figure 2H:
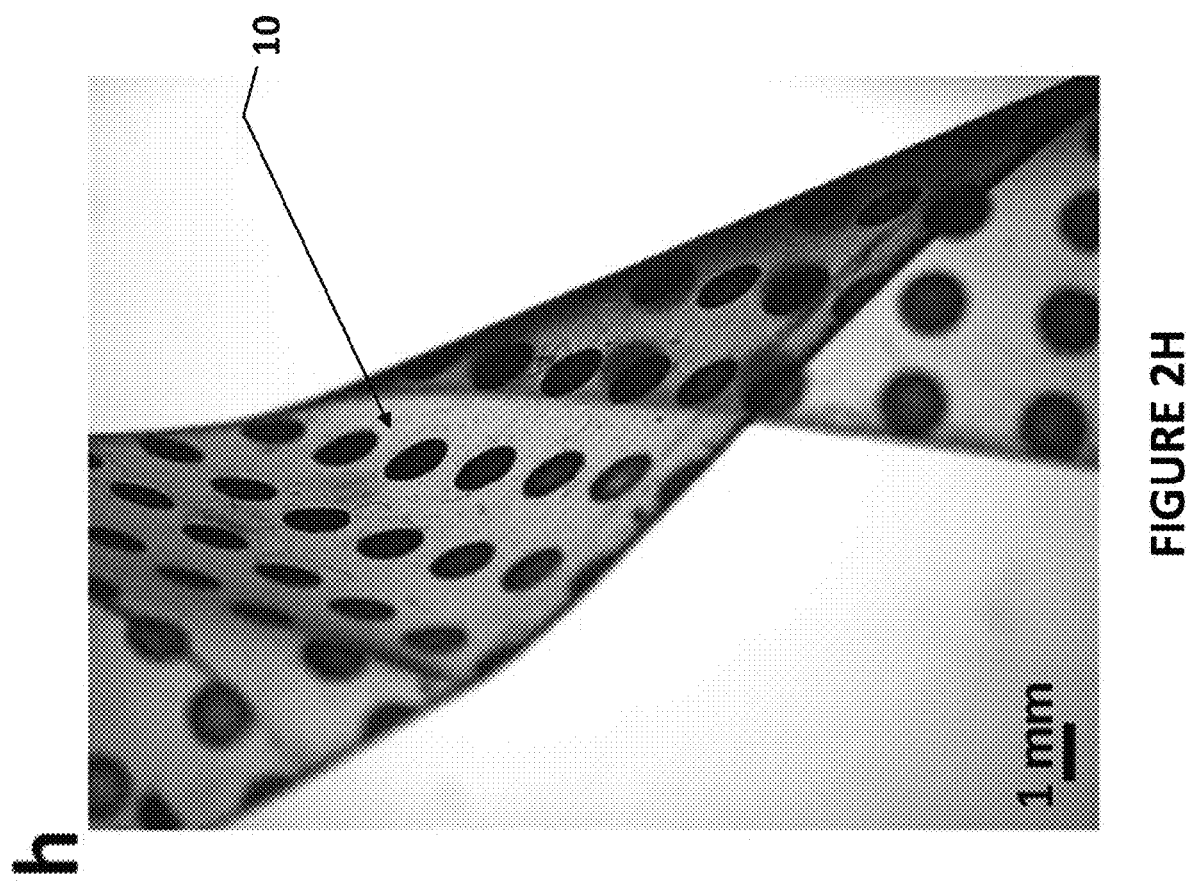

FIGS. 2A-E show several examples of microscale graphene patterns 14(1) to (5) transferred onto a 25 μm thick polyimide tape 12 with silicone adhesive. The PDMS substrate used here contained 15.4 μm deep negative features 22 prefabricated at its surface. The graphene structures 14 inside these negative patterns were 10.3±2.7 μm thick, which was determined by a surface profilometer (see the measurement method in the Experimental Section). The transferred patterns 14 were of high spatial resolution (≈5 μm), and mostly retained the features of the original patterns 22 at the PDMS surface. This method also allowed producing graphene patterns on a tape roll, as shown in FIGS. 2F-H (see also FIGS. 9A-B, Supporting Information, for the fabrication process). It should be noted that, to realize these graphene patterns on a tape, several critical geometrical and processing parameters, including the volume of graphene suspensions over the unit surface area, the depth, and width of the preformed negative features at the PDMS surface, and the number of repeating D2SP times, should be carefully considered. The following section will discuss the influences of these parameters on the quality of pattern formation and transfer.

Figure 3A:
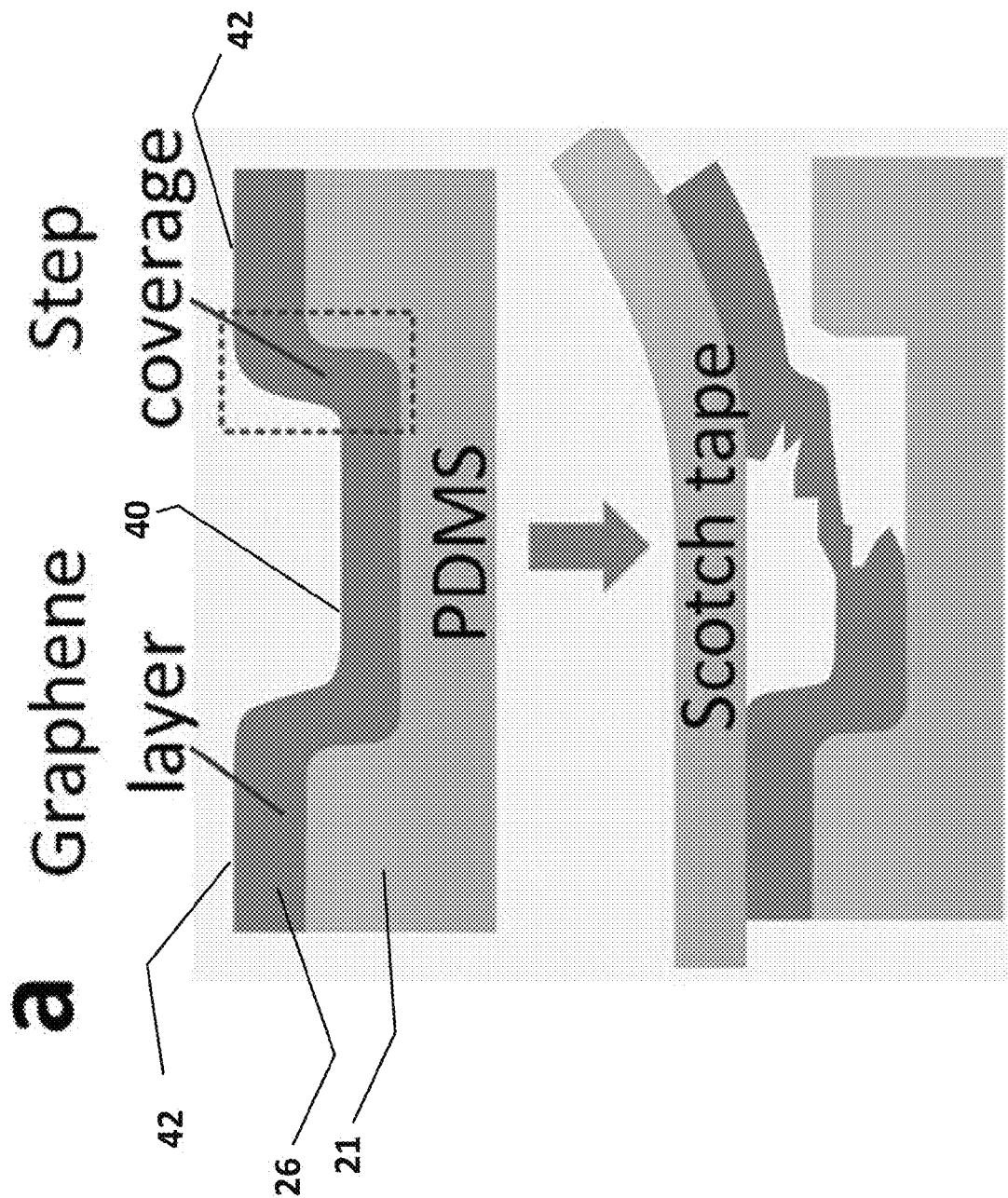
Figure 3B:
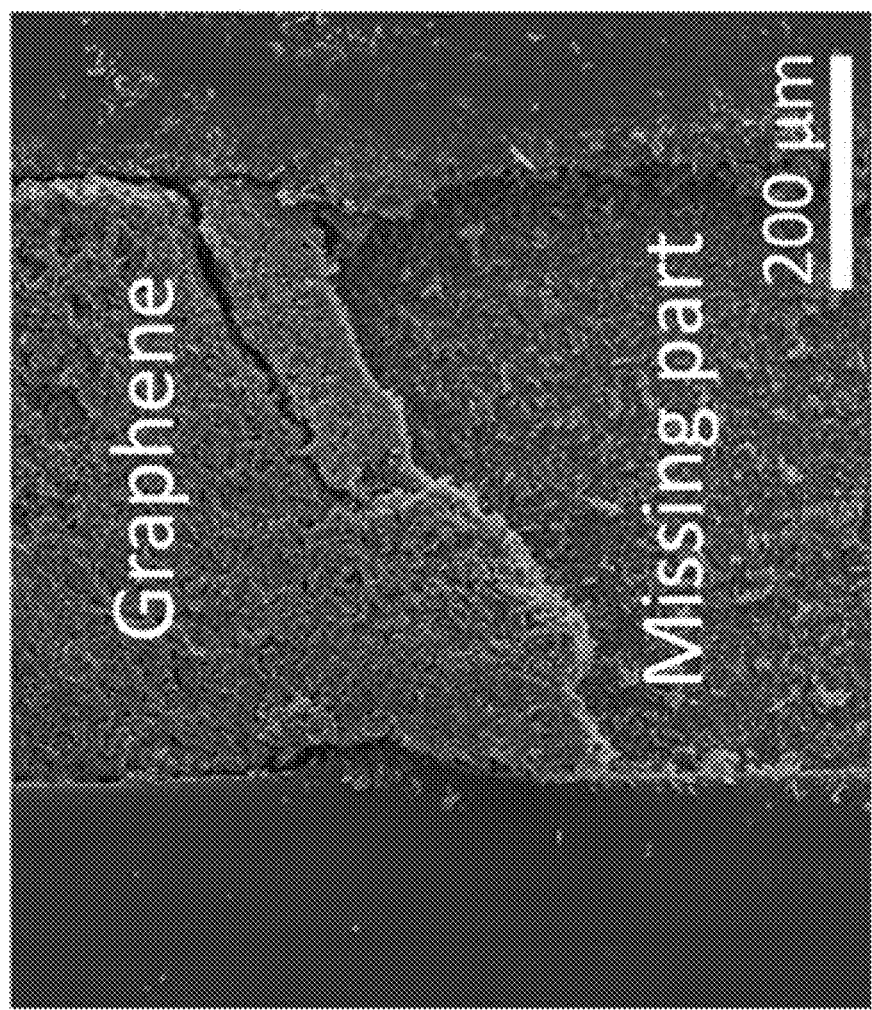
Figure 3C:
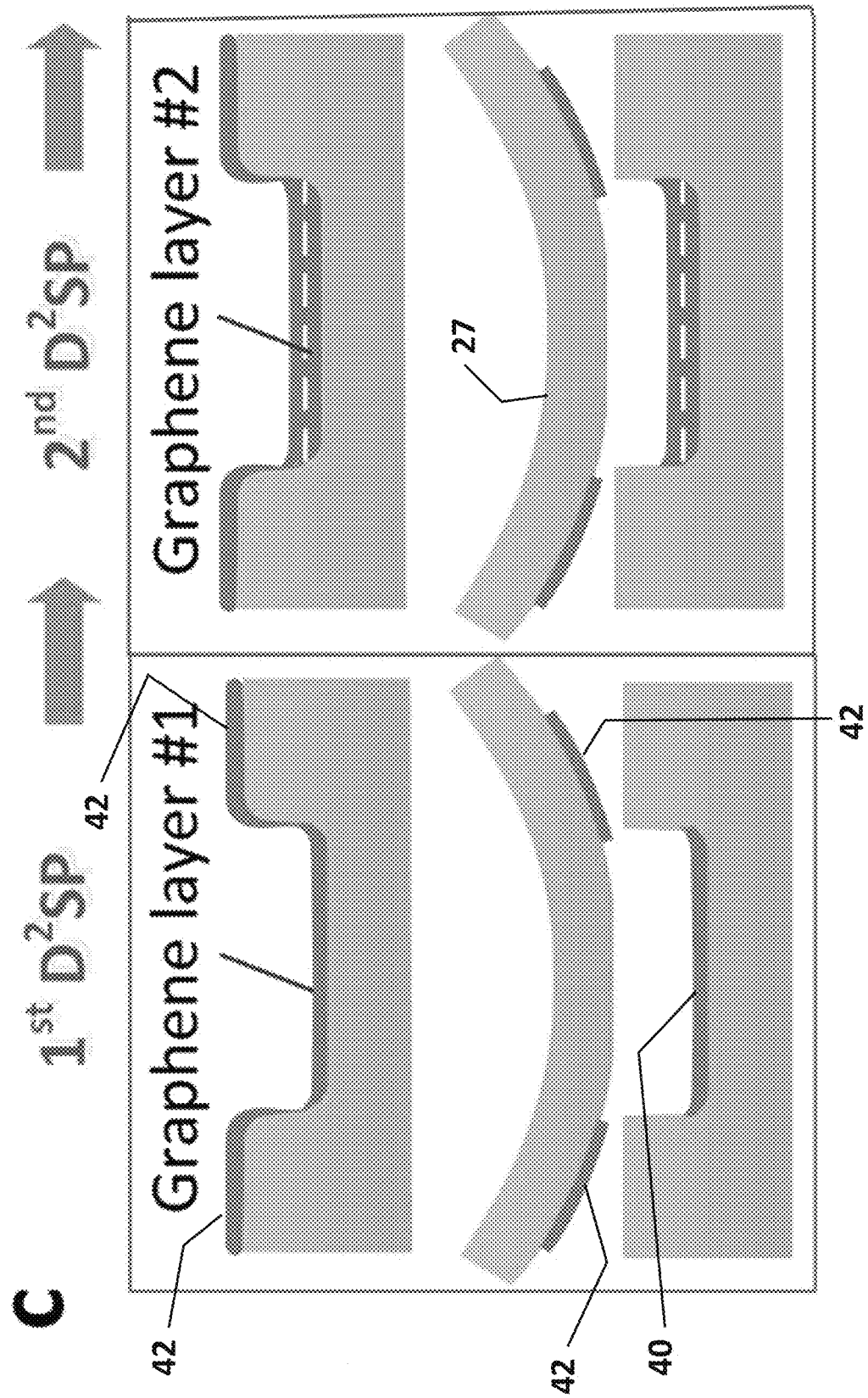
Figure 3D:
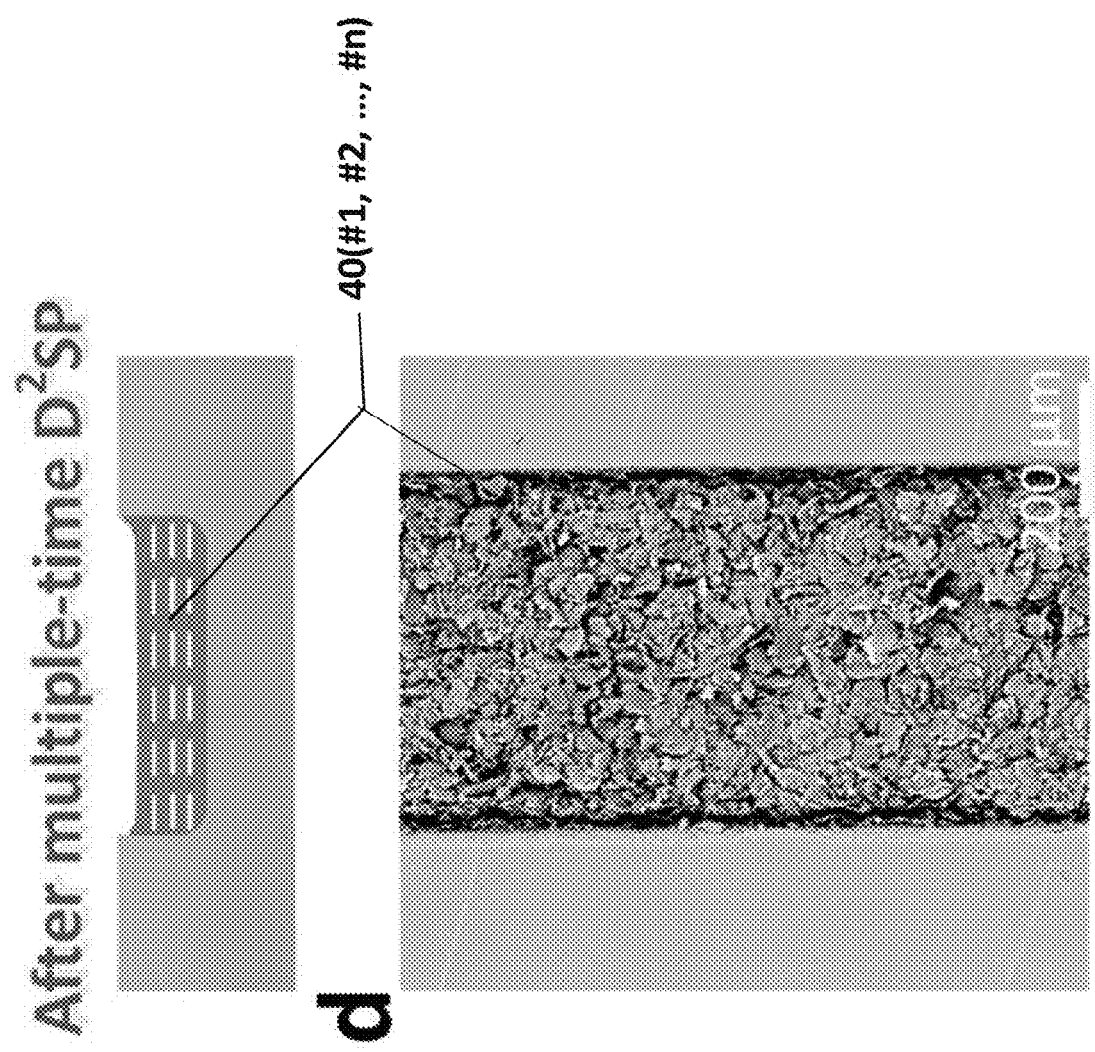
Figure 3E:
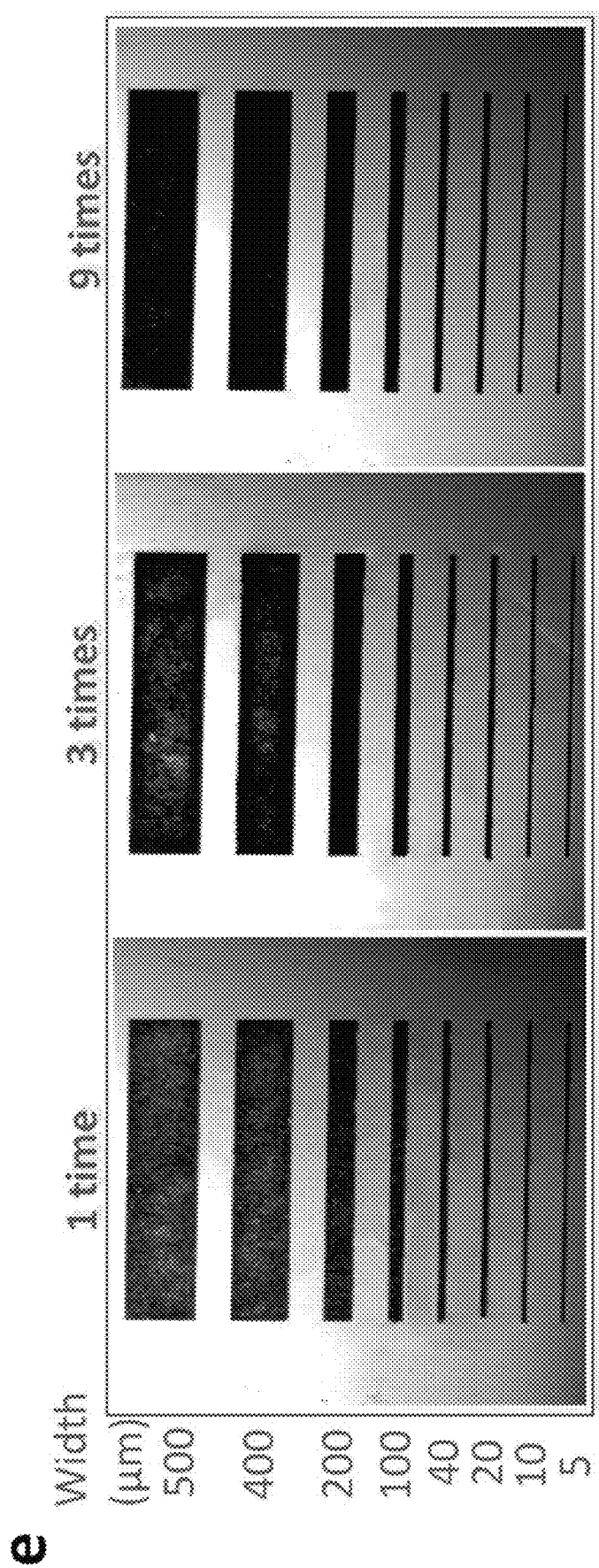
Figure 3F:
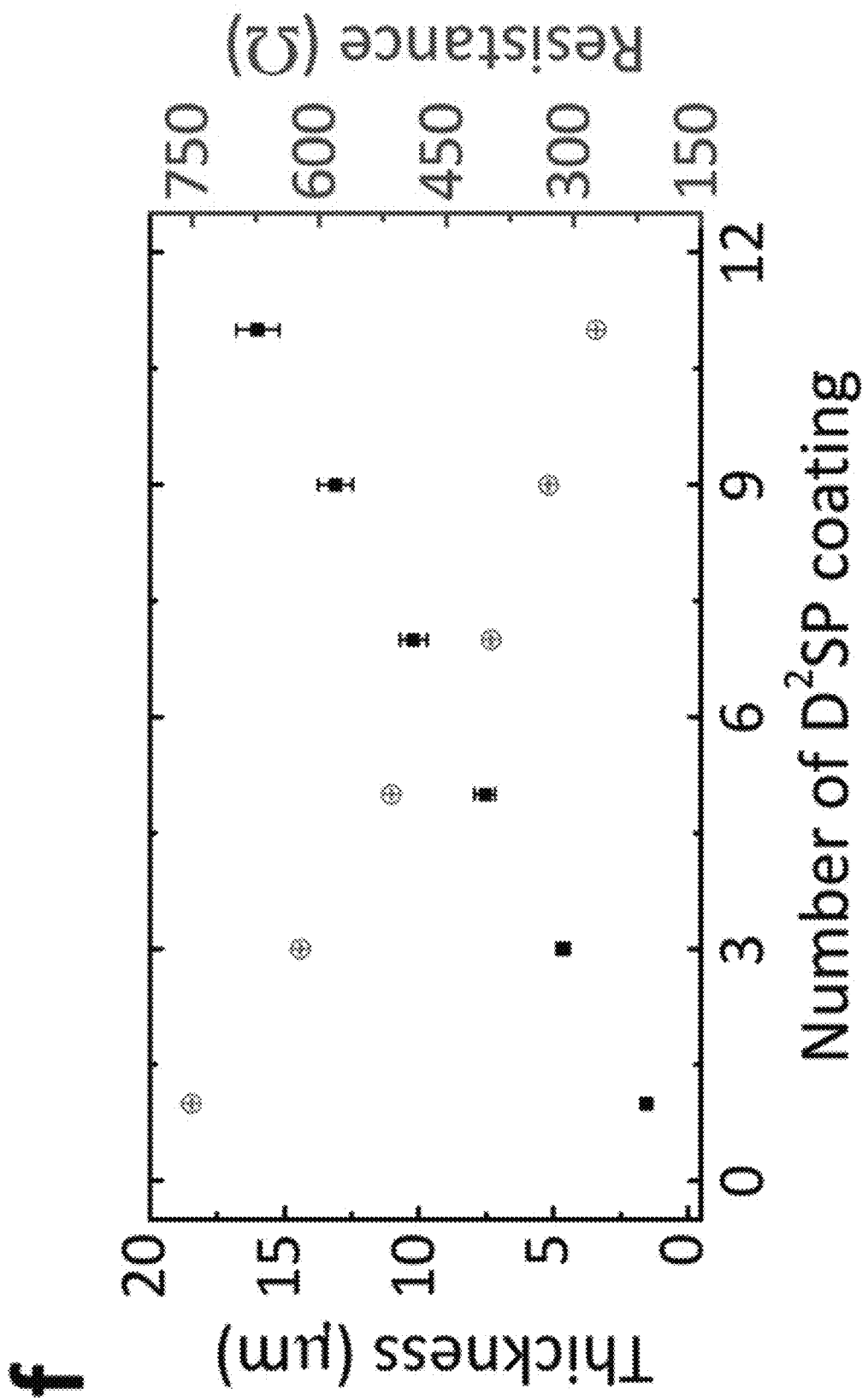

First, although a thick graphene film could easily be produced by loading a large volume of graphene suspensions per unit surface area onto the PDMS surface, patterning of a thick film was difficult using the D2SP method. The experiment here utilized a PDMS substrate 21 containing 15.4 μm deep and 500 μm wide channels 22 at its surface and was covered by a 10.3 μm thick graphene film 26. This thick film 26 was formed by drop-casting with 20 mg mL$^{-1}$ concentration graphene suspensions at a large volume per unit surface area of 710 μL cm$^{-2}$ (FIG. 3A, top). Then, Scotch tape 27 (sometimes referred to herein as "cleaning tape" to differentiate it from final substrate tape 12) was applied and stick to the PDMS surface, with an intent to clean the PDMS surface by removing the unwanted graphene 42 from the PDMS top surface (see ref. nos. 42 which include both graphene at the top surface of the PDMS but also sometimes graphene at and partially down the steps/sidewalls between the top surface and the bottom of the negative features 22 in the PDMS). However, as shown schematically in FIG. 3A and experimentally in FIG. 3B, some portions 41 of the graphene 40 inside the channels were also removed by the Scotch cleaning tape. A possible explanation for this is that the tape peeling could not easily break such a thick graphene film at the step and sidewall of the channel 22 completely covered by the continuous graphene film. Therefore, to successfully produce thick graphene patterns in the PDMS channels, sequential D2SP processes were applied multiple times (each time producing a thin film until the desired film thickness was achieved (FIG. 3C) (e.g. two or more drop cast graphene layers 26(#1, #2, ...). Specifically, our experiment shows that when the drop-casted graphene film was no more than ≈1.5 μm thick, Scotch tape worked perfectly to break the film at the step of the channel, almost regardless of the channel depth, as long as the tape was not in direct contact with the graphene inside the channel. Therefore, in the subsequent experiments, graphene suspensions (concentration: 20 mg mL$^{-1}$) were loaded to the PDMS surface (the volume of graphene suspensions per unit surface area: 100 μL cm$^{-2}$) to form an ~1.45 μm thick graphene film (FIG. 3C, top). Next, this thin film was patterned to form the graphene structures inside the channel using the stick-and-peel process with Scotch tape (FIG. 3C, middle). To increase the thickness of the graphene patterns inside the channel, the whole D2SP process (described in FIG. 1A, subparts a-e) was repeated multiple times until a desired thickness was obtained (FIG. 3C, bottom). FIG. 3D shows the PDMS channel filled by an ~10.3 μm thick graphene film after seven times repeated D2SP processes. FIG. 3E shows the optical images for the graphene patterns in the PDMS channels obtained with 1-7 times repeated D2SP processes. FIG. 3F shows that the graphene patterns exhibit a linear increase in thickness and a linear decrease in electrical resistance with the number of repeated D2SP processes (or the number of coatings).

Figure 3G:
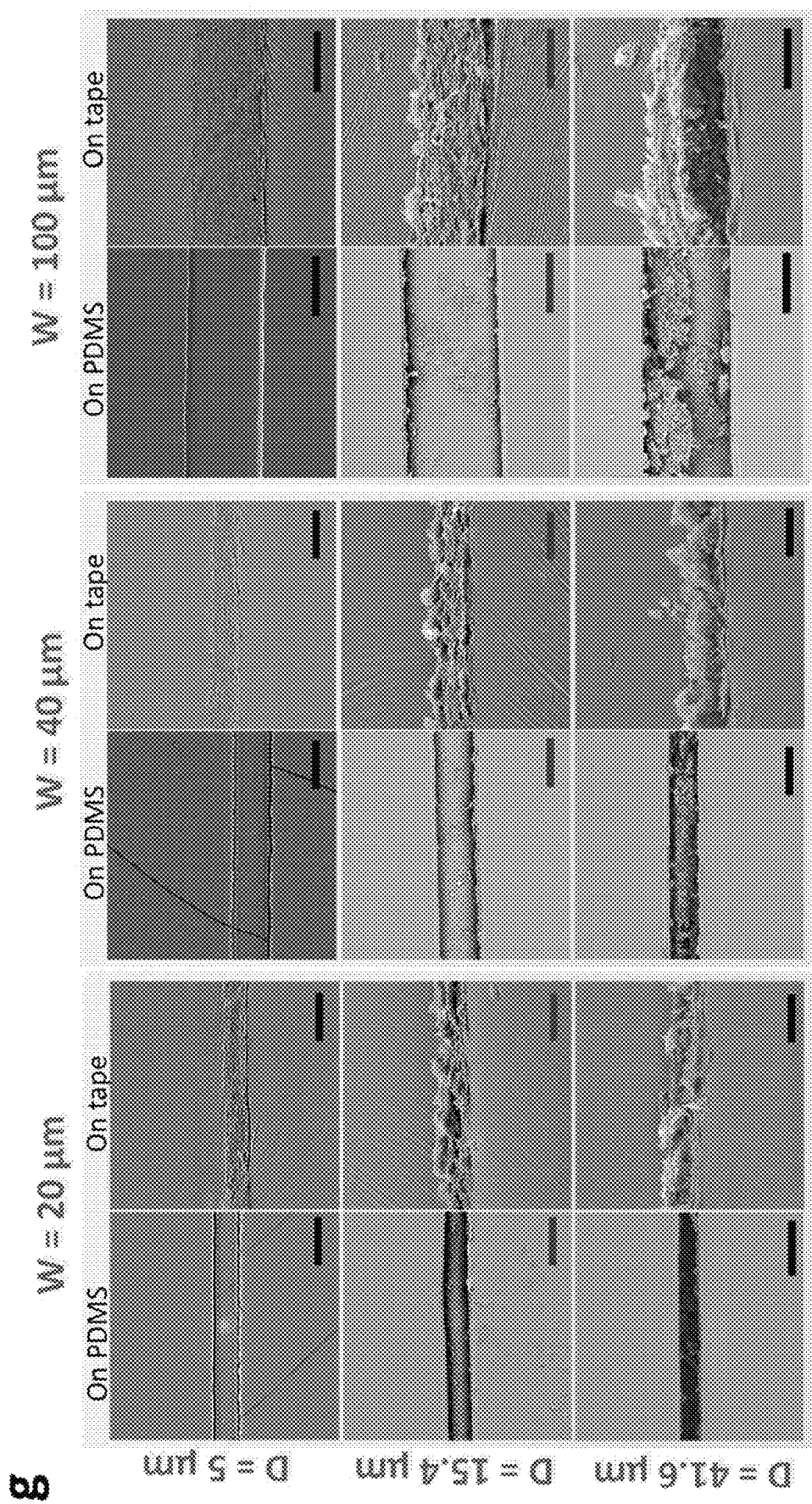

Next, to transfer the patterned graphene from the PDMS channels onto a final tape via the ST process, we investigated the influences of the channel width and depth on the transfer quality. The experiment here utilized the PDMS channels with depths of 5, 15.4, and 41.6 μm, and widths of 20, 40, and 100 μm. By performing sequential D2SP processes, the channels were almost fully filled by graphene, with a few micrometers gap distance to the channel top. Polyimide tapes with silicone adhesive were used to transfer the graphene patterns, with results indicating that, after the graphene structures were transferred onto the tape, the 41.6 μm deep channels of all the different widths contained graphene residues as shown in FIG. 3G. This may be because the van der Waals force within the drop-casted graphene film was not large enough to hold the 36.7 μm thick graphene structure together during transferring using the tape. The other plausible cause may be due to an increased drag force occurring at the large-area side-walls of the deep channel and acting on the graphene during peeling. When the channel depth decreased to 15.4 μm and contained 10.3 μm-thick graphene, the tape transfers of graphene became easier and only a very minor residue remained in the channels. With decreasing channel width from 100 to 20 μm, the increased aspect ratio of the channel led to some-what increased amounts of residue at the channel edges, but overall the transferred graphene on the tape retained the original pattern features of the graphene structures in the channels. Furthermore, in the case of transferring 2.3 μm thick graphene from the 5 μm deep channels, no residues were observed to remain in the channels for all widths.

Figure 3H:
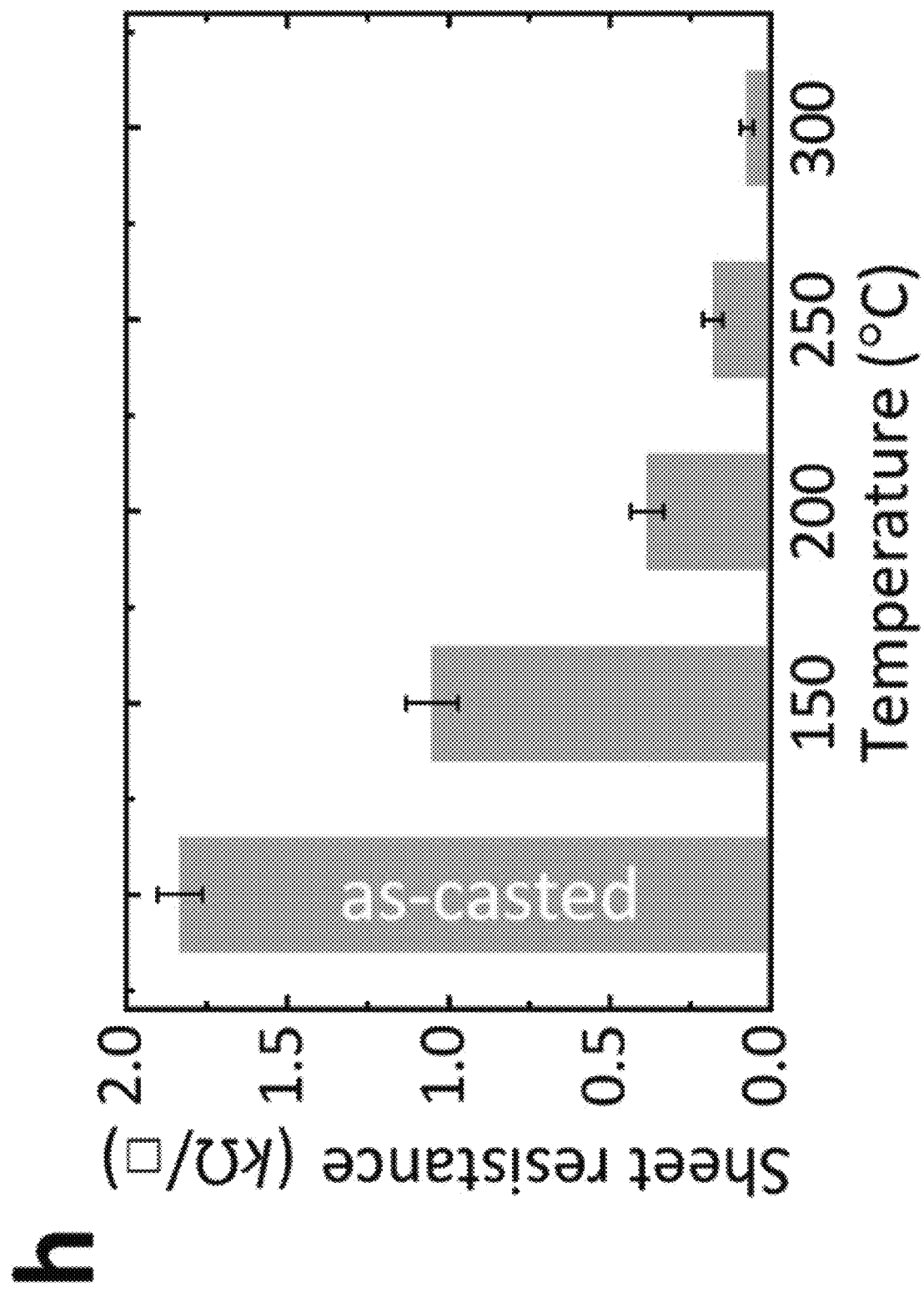
Figure 3I:
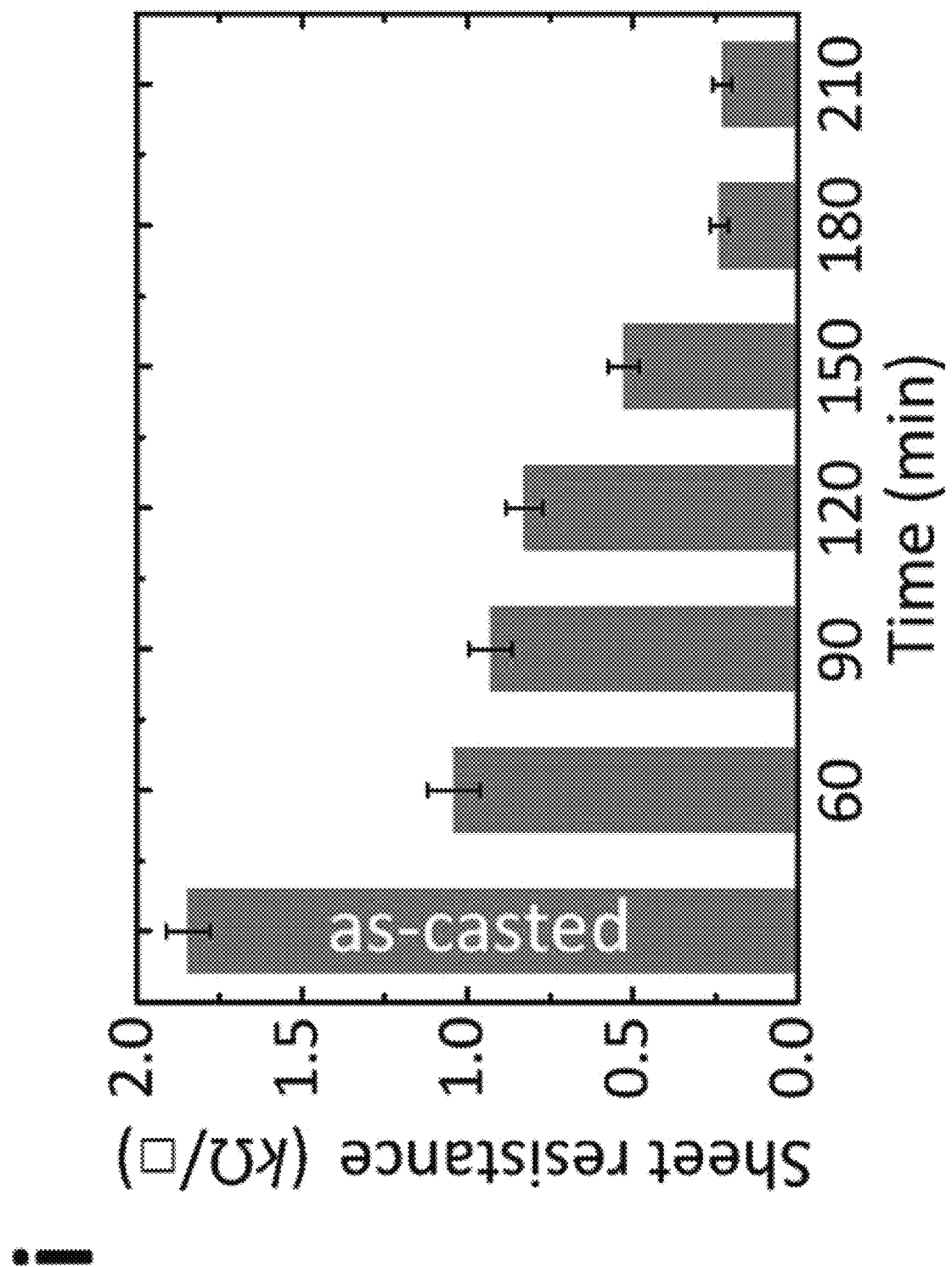

To increase electrical conductivity of the transferred graphene, the transferred graphene patterns on the polyimide tape were annealed in air. Essentially, thermal treatment may improve contacts between graphene nanoplatelets, and thus increase electrical conductance of the formed graphene pat-terns. [58] Because polyimide tapes are dimensionally stable below 400° C., [62] the annealing was carried out at temperatures ranging from 150 to 300° C. (FIG. 3H) over different treating times ranging from 60 to 210 min (FIG. 3I). The results show that the sheet resistance of the transferred graphene (≈10.3 μm thickness) was decreased by about seven times after the treatment at 250° C. for 180 min. Increased annealing time did not help to further decrease the sheet resistance. As the annealing temperature increased toward 300° C., the sheet resistance was found to decrease, but, the optimum annealing temperature was chosen as 250° C. because of the above-mentioned critical temperature restriction of polyimide tape. [62]

Figure 3J:
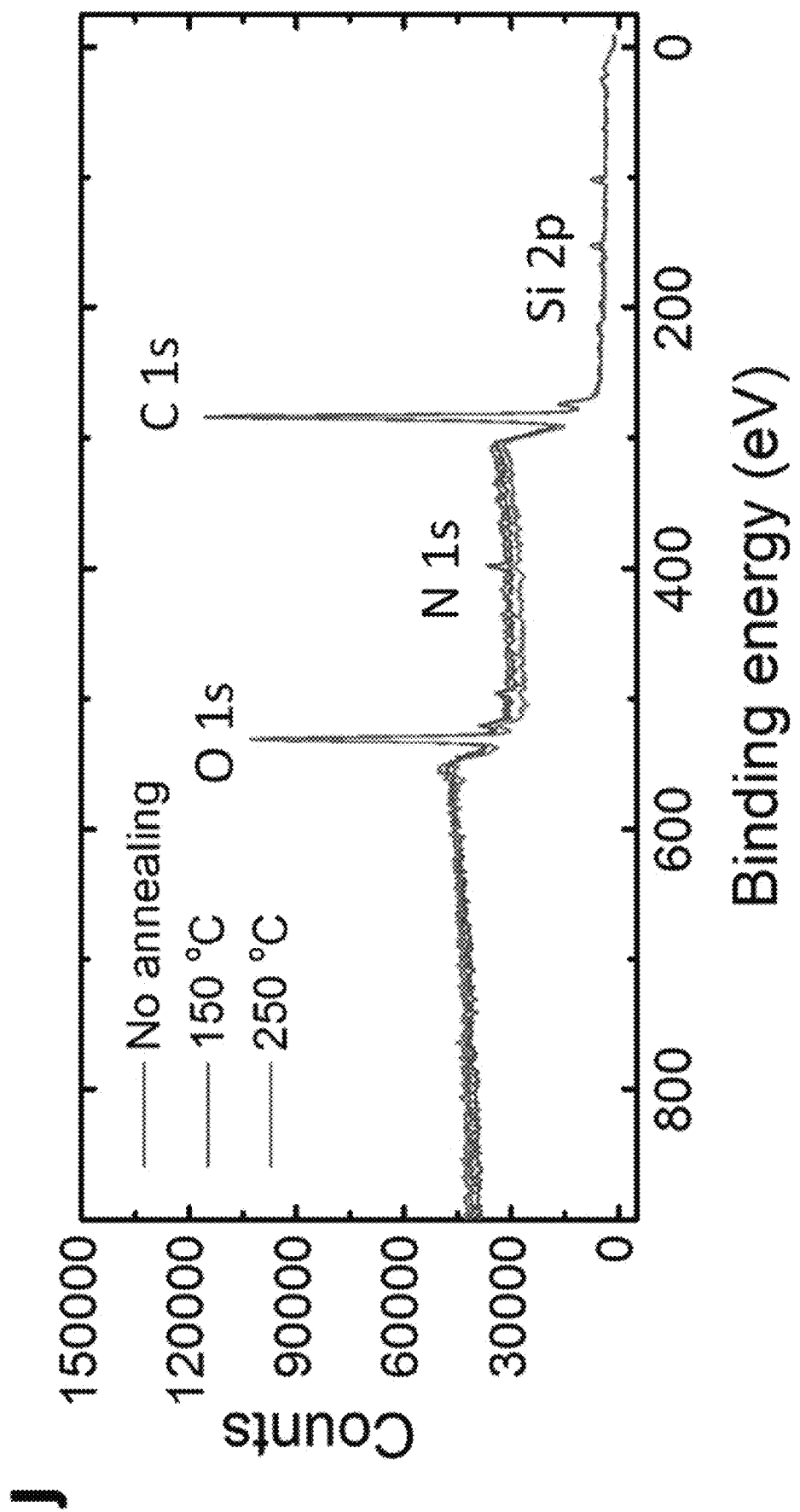
Figure 3K:
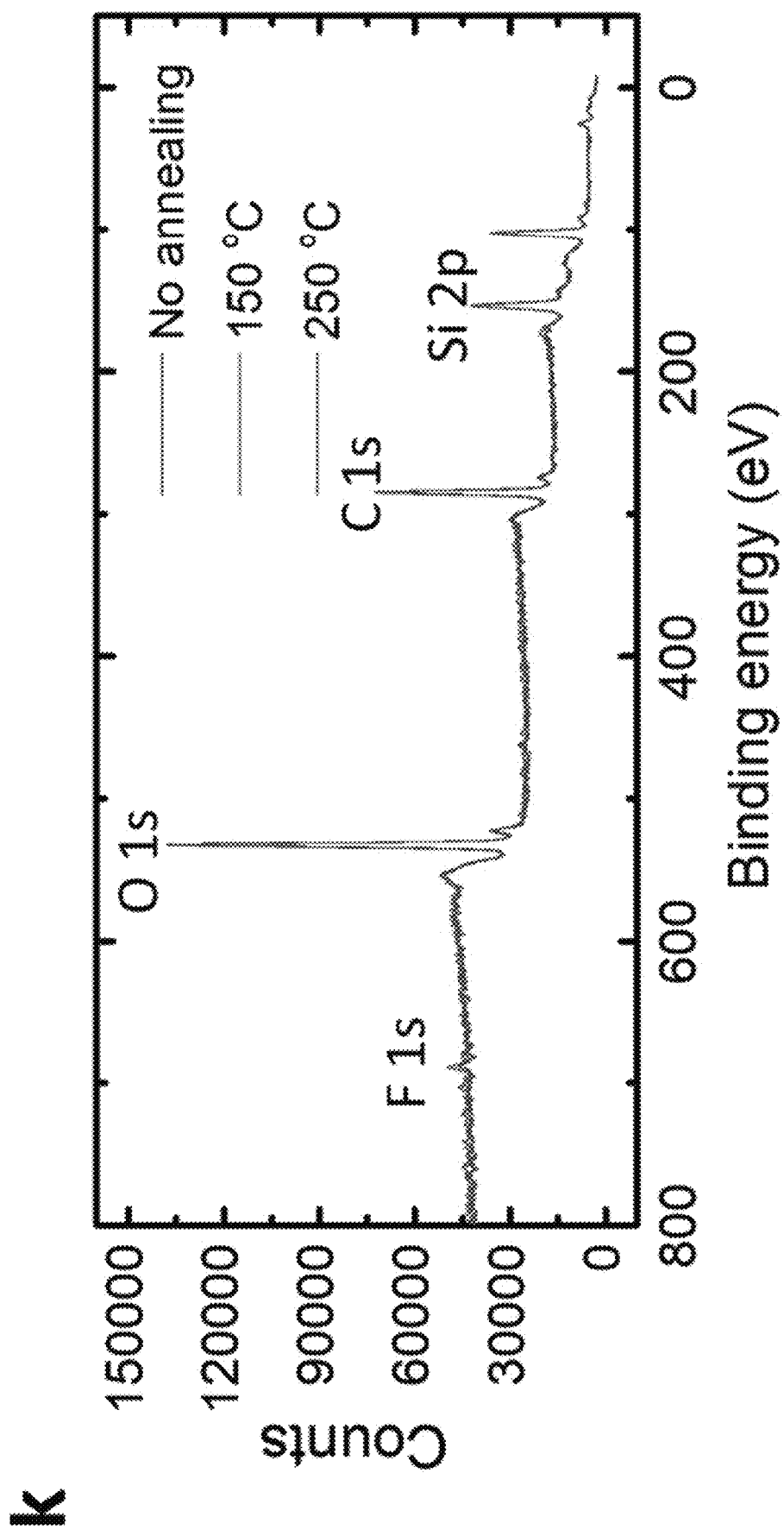

X-ray photoelectron spectroscopy (XPS) was used to characterize the composition of the transferred graphene structures on tape before and after thermal treatment. FIGS. 3J, K depicts the XPS survey spectra for two groups of samples, that is, the transferred graphene (thickness: 10.3 μm) on a 25 μm thick polyimide tape, and the polyimide tape alone. There were three samples in each group, including one treated at 150° C. for 180 min, one 250° C. for the same time, and another not treated. The results show that all the on-tape graphene samples contain peaks assigned to C 1s (284 eV), O 1s (531.3 eV), N 1s (398.6 eV), and Si 2p (101.4 eV) (FIG. 3J), and all the polyimide tape samples exhibited peaks belongs to C 1s (284.6 eV), O 1s (532.7 eV), F 1s (688.6 eV), and Si 2p (102.4 eV) (FIG. 3K). For the on-tape graphene samples, O 1s peak occurs due to the physically adsorbed oxygen; [63] Si 2p peak might originate from the adhesive of the polyimide tape; and N 1s peak was observed because the graphene used here is N-doped graphene nanoplatelets. [64] Further, high-resolution spectra analysis (FIGS. 10A-D and 11A-D, Supporting Information) confirm that the thermal treatment did not make distinct changes to the chemical structure of the graphene and polyimide tape samples, although the intensity of C 1s peak decreased slightly at 250° C. The intensity of Si 2p peak of the graphene pattern decreased as the temperature increased up to 250° C. (FIGS. 10A-D, Supporting Information).

Figure 4A:
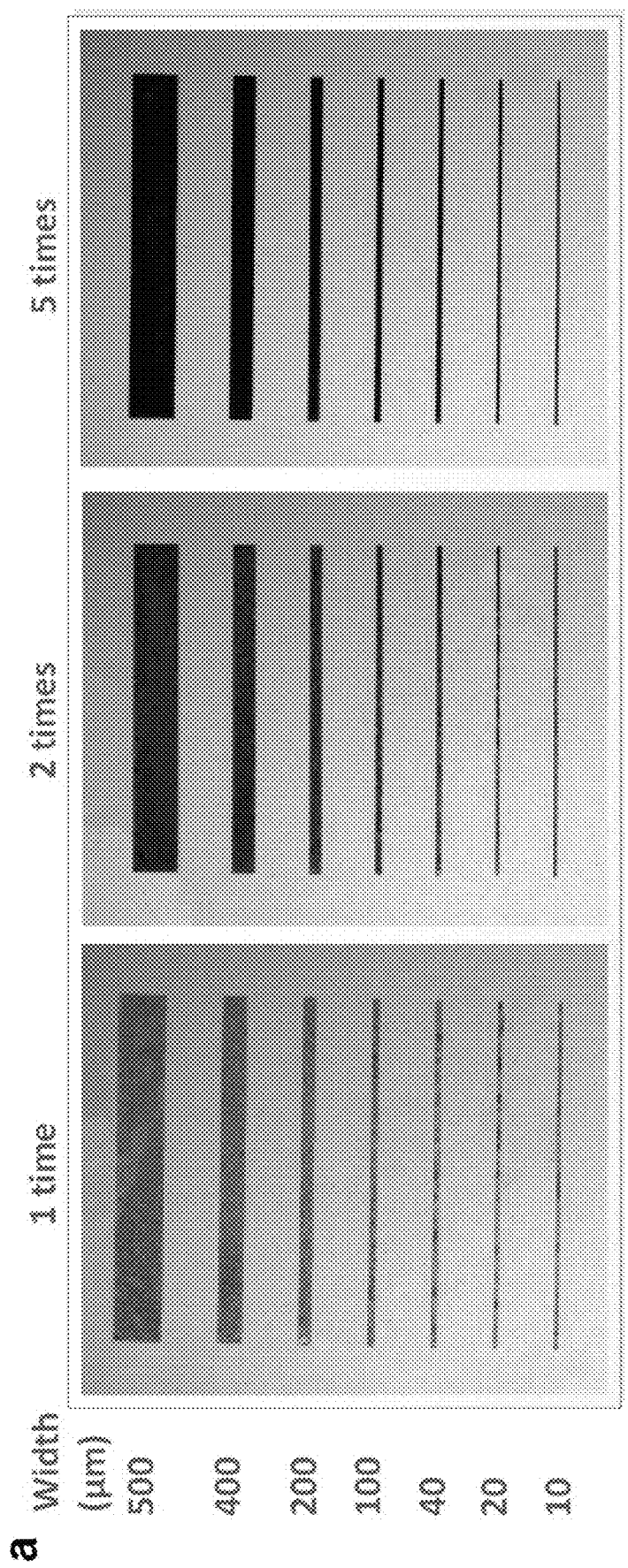
Figure 4B:
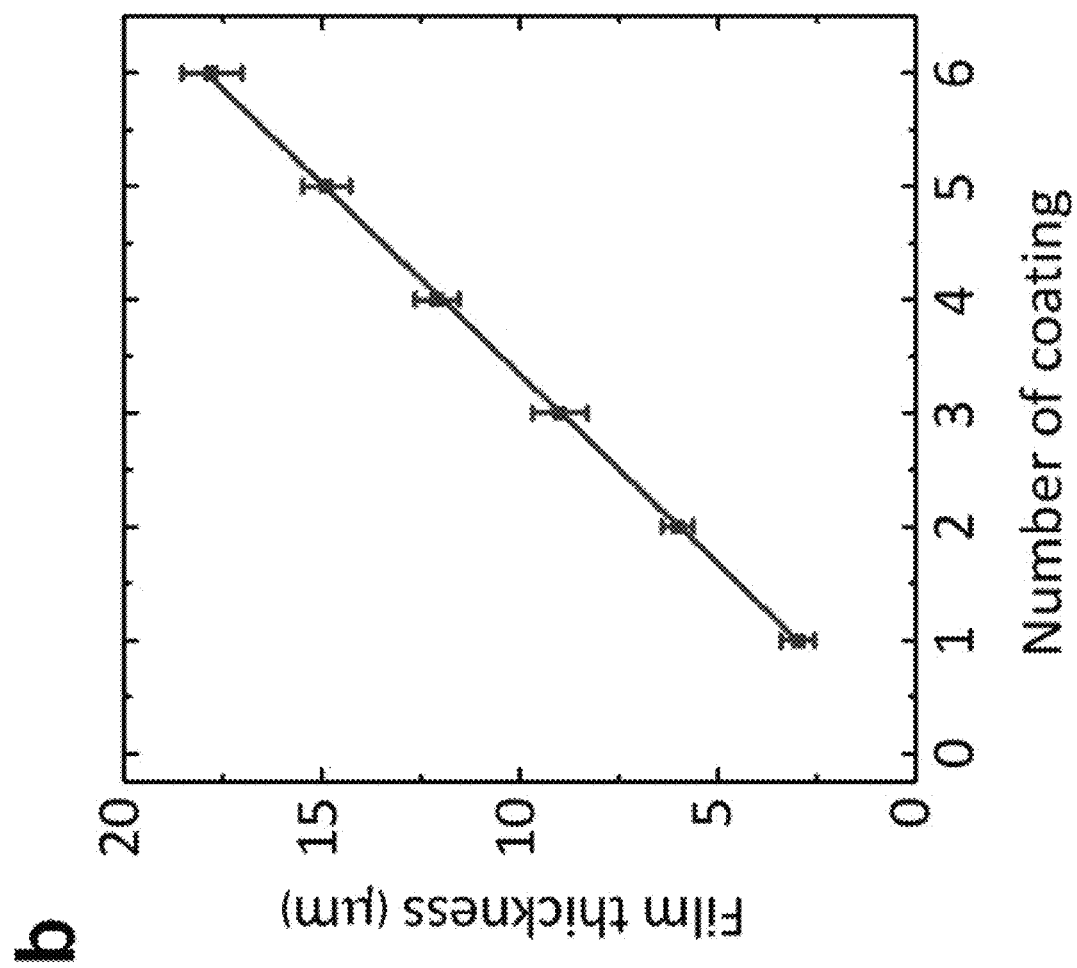
Figure 4C:
Figure 4D:
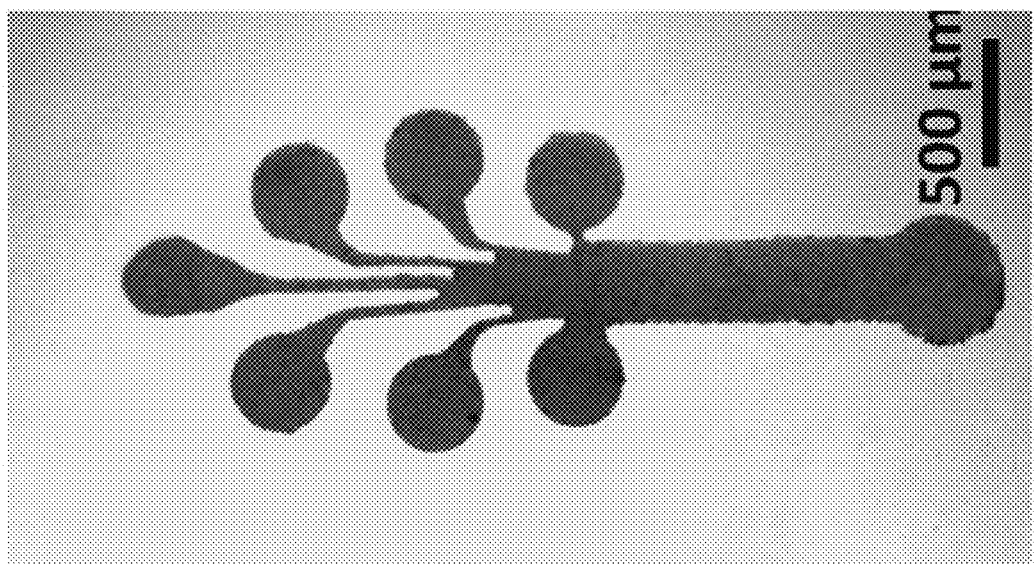
Figure 4E:
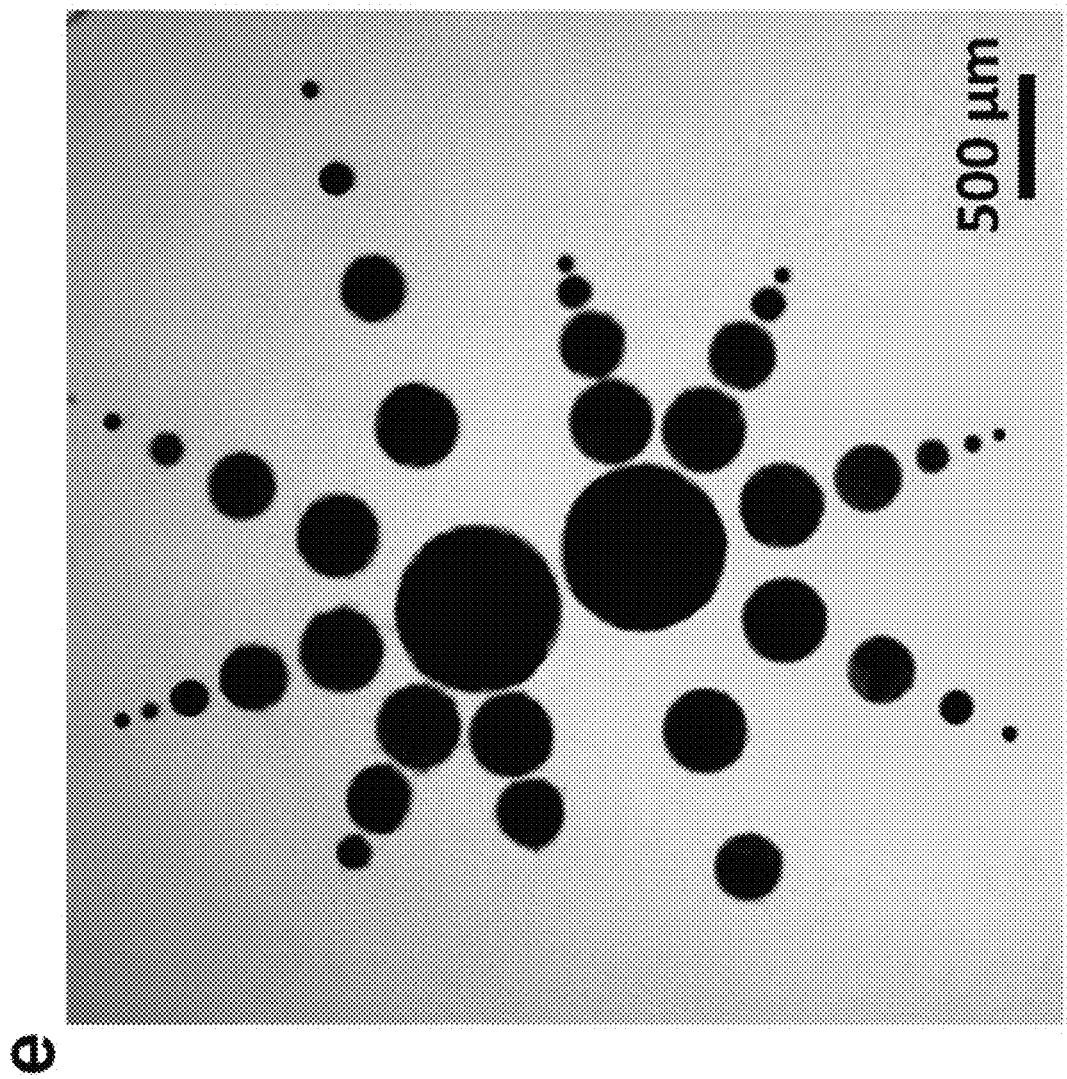

The present patterning and transferring method could also be employed to obtain rGO patterns on tape. FIG. 4A shows some rGO strip patterns formed inside the PDMS channels at different coating (or D2SP) times, and FIGS. 4C-E shows the rGO patterns transferred onto the polyimide tape, using essentially the same method as described in FIGS. 1A-B. The film thickness of the rGO linearly increased with coating time (FIG. 4B). The experiments here utilized a PDMS substrate with 15.4 μm deep negative features at its surface. Five repeated D2SP processes were sequentially applied to obtain the rGO patterns inside the negative features. For each coating, 100 μL cm-2 of rGO suspensions (20 mg mL-1 in the mixture of ethanol and DI water at a volume ratio of 7:3) were drop-coated over the entire PDMS surface.

Figure 4F:
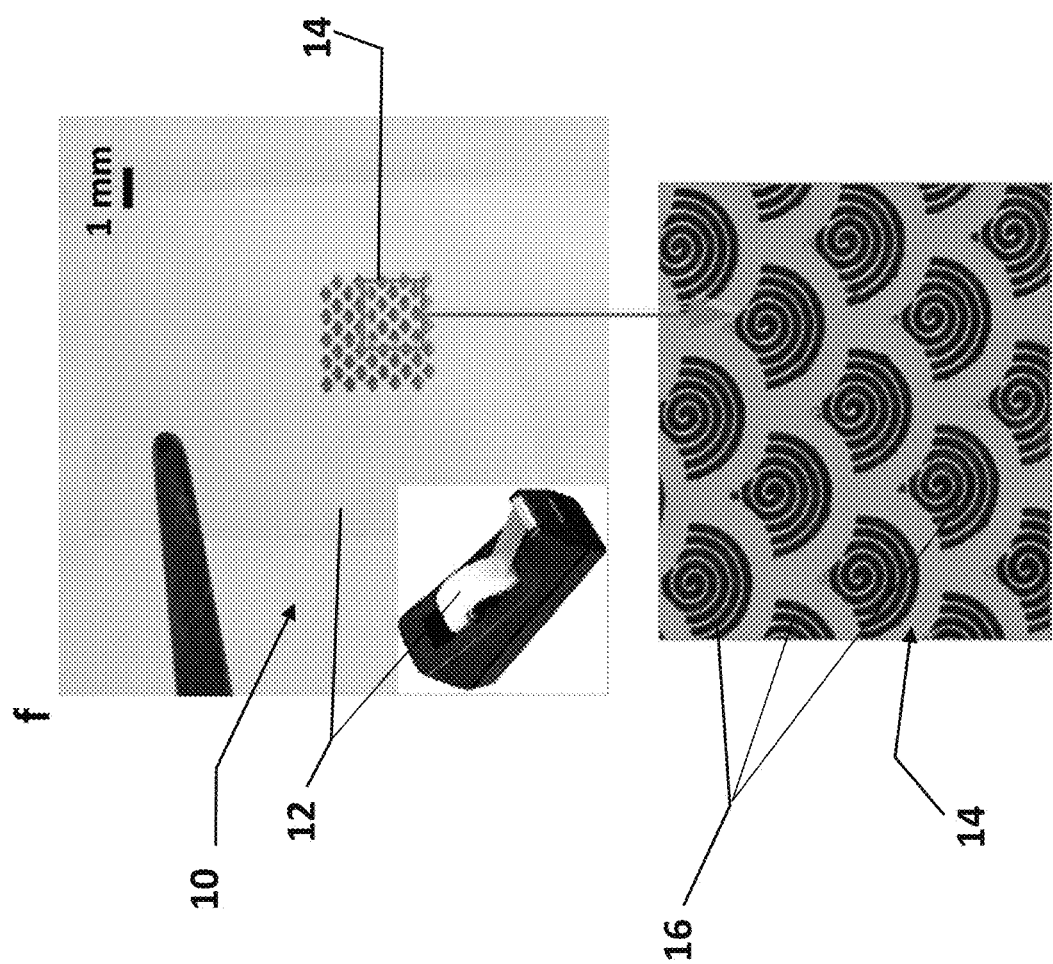
Figure 4H:
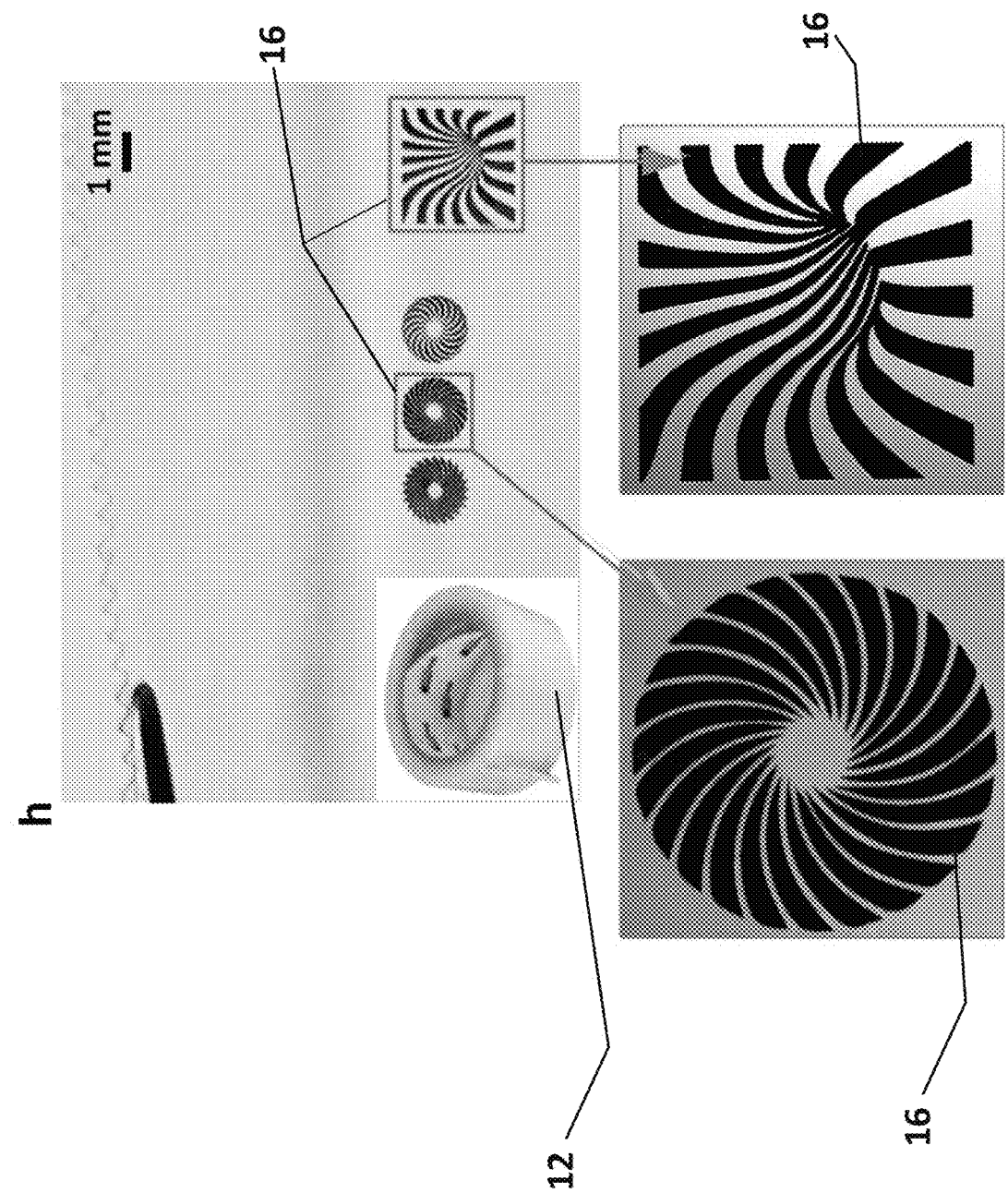

In addition, the present method can also be used to pro-duce graphene patterns on different adhesive substrates such as Scotch and aluminum foil tapes, both with acrylic adhesive (FIGS. 4F, G), and Scotch tape with synthetic rubber adhesive (FIG. 4H). All the graphene patterns in FIGS. 4F-H were formed with five repeated D2SP times and transferred onto the target tapes with the ST process.

2.2. Application Demonstrations
2.2.1. On-Tape Strain Sensors

Figure 5A:
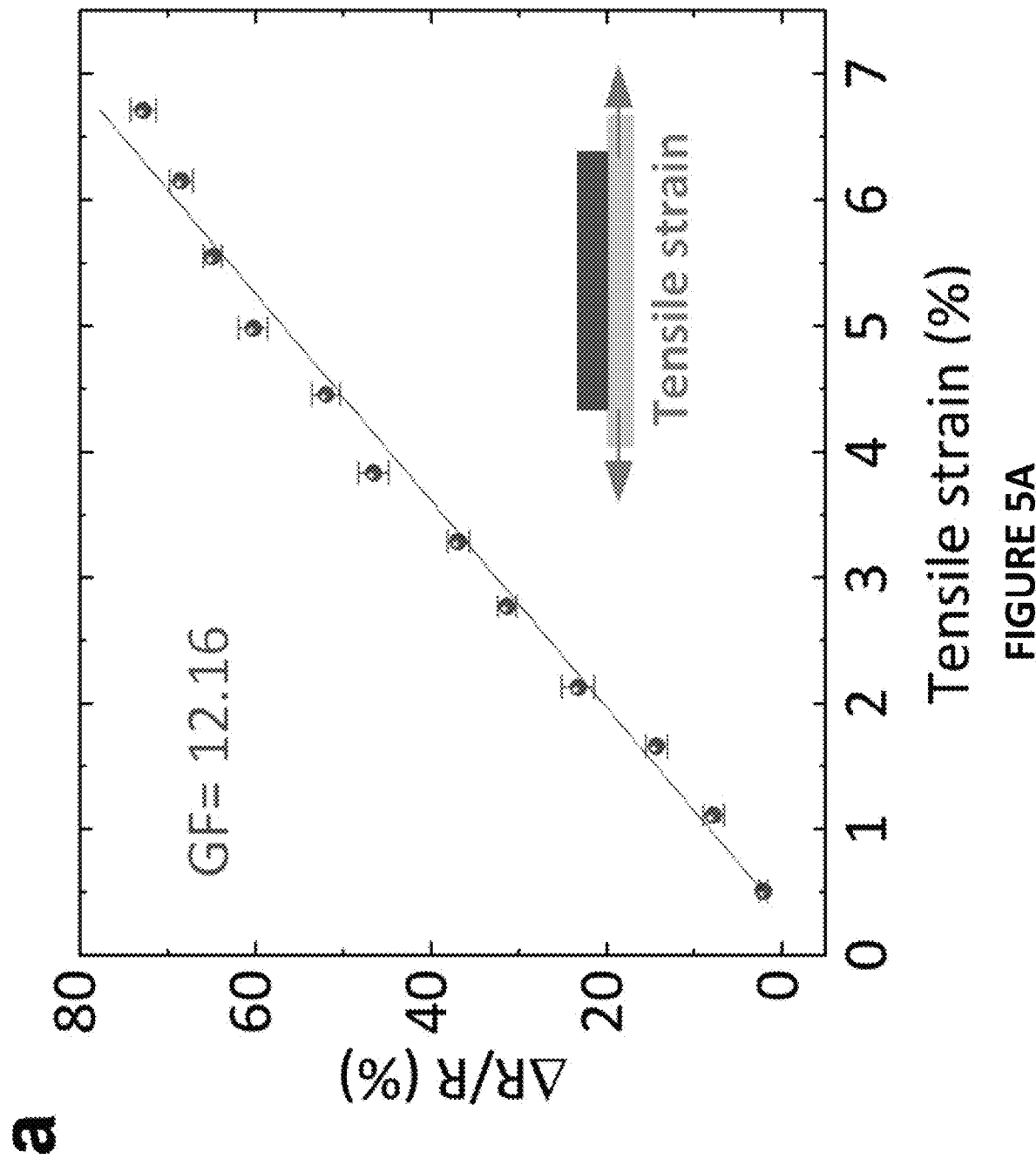
Figure 5B:
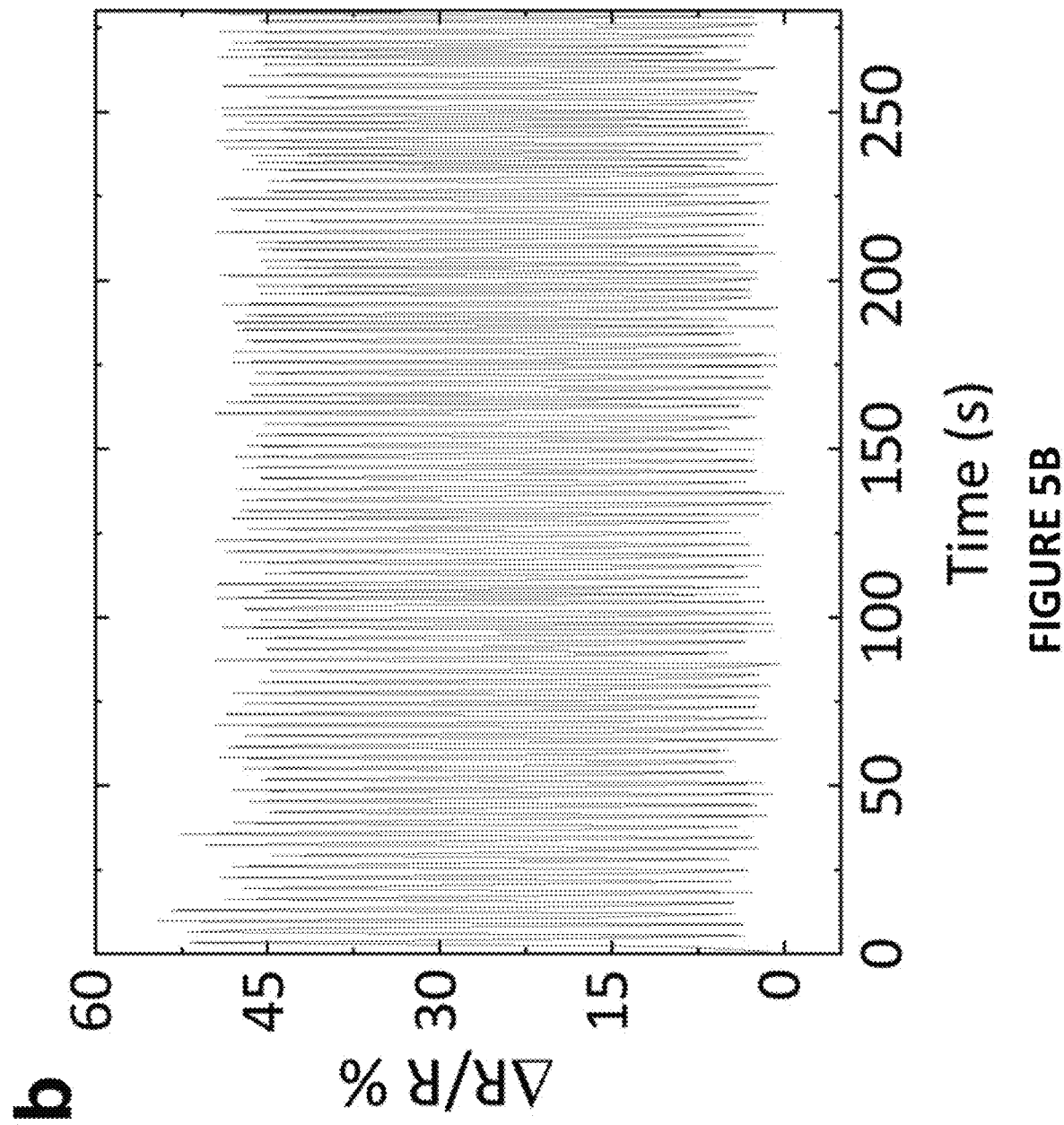
Figure 5C:
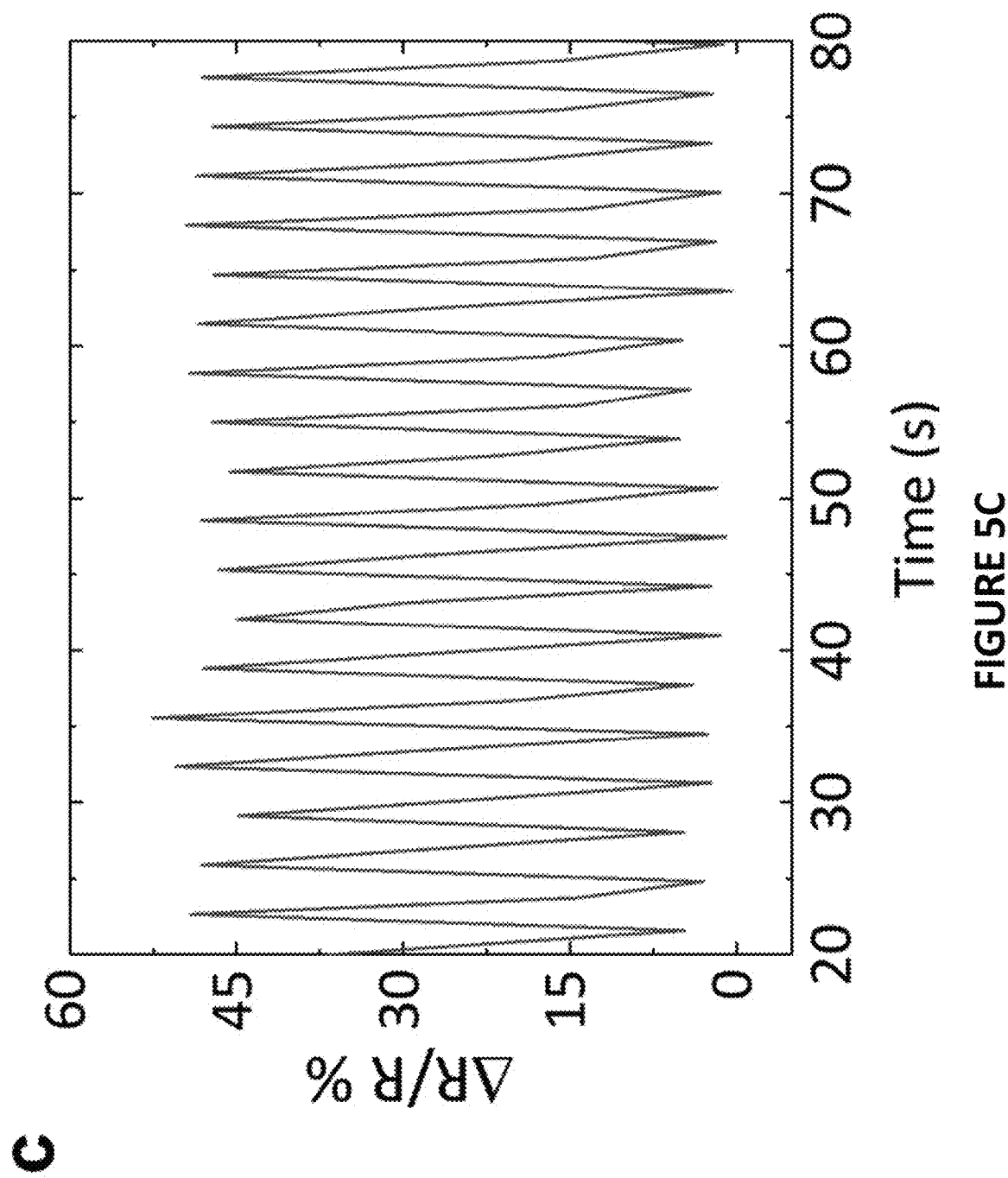
Figure 5D:
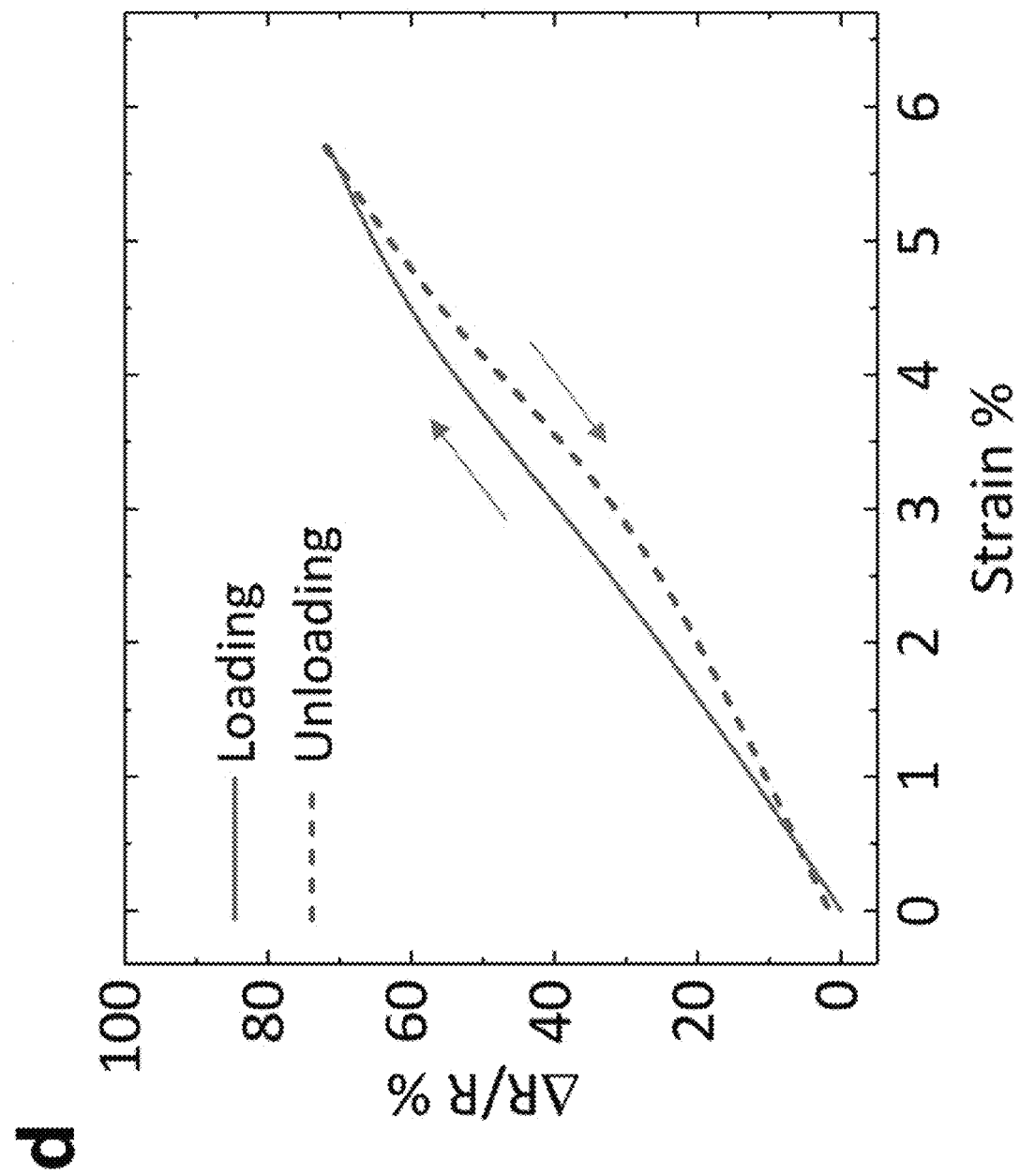
Figure 5E:
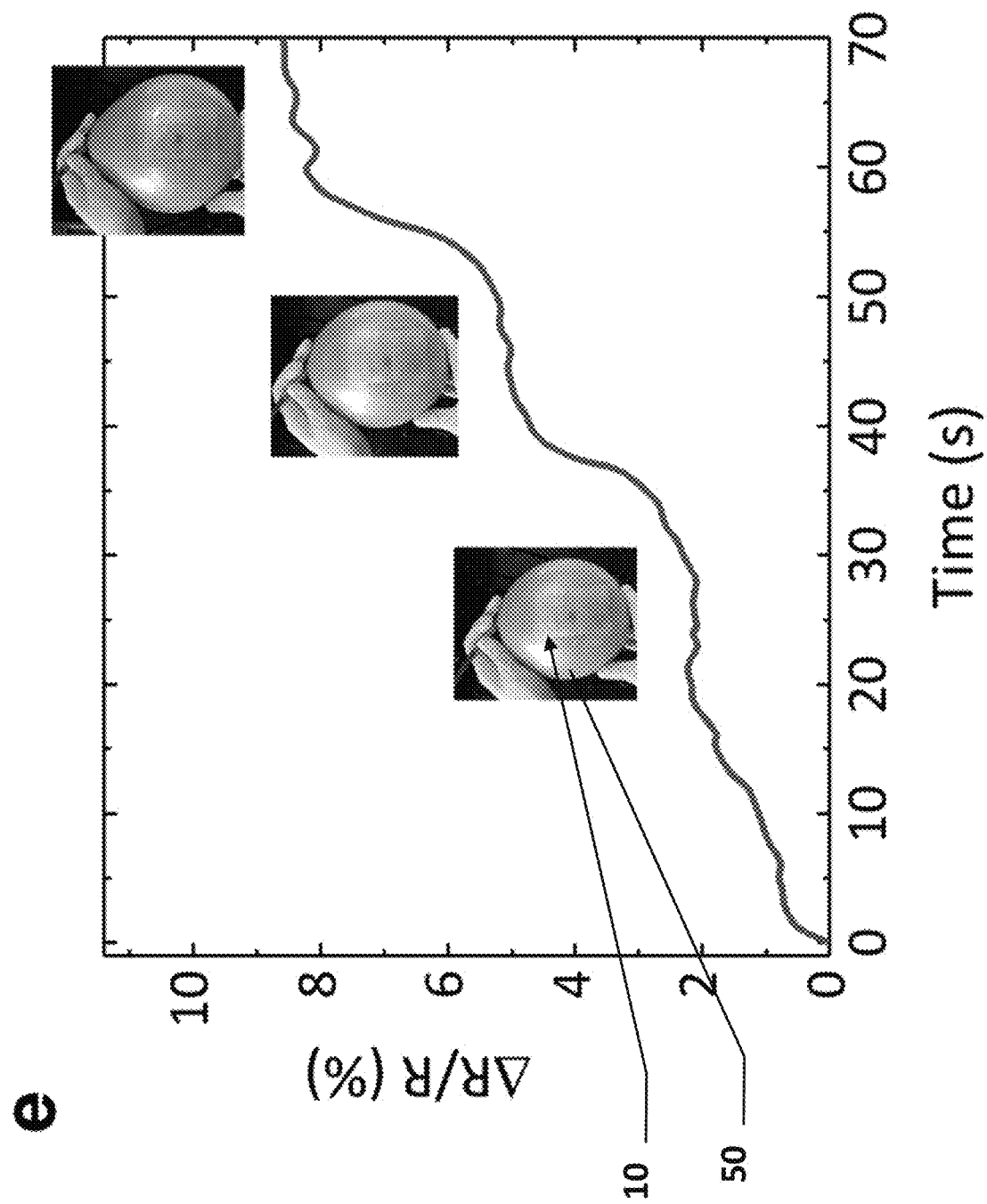

A graphene strip pattern (6 mm length, 800 μm width, and 10.3 μm thickness) was transferred onto the polyimide tape as a strain sensor. The sheet resistance of the patterned graphene was 0.22±0.12 $\Omega$k sq$^{-1}$. Electrical contacts between the graphene pattern and external tin copper electronic wires (Gauge 20) were realized with silver paste. FIG. 5A shows the resistance response of the sensor to a tensile strain applied along the length direction of the graphene pattern. The relative resistance changes of the sensor ($\Delta R/R$) increased linearly with applied tensile strain. The gauge factor of the sensor was found to be 12.16 from the slope of the linear fitting curve in FIG. 5A. FIGS. 5B, C demonstrated the stability of the sensor by loading and unloading a 4.4% tensile strain for 100 times. The hysteretic behavior of the sensor was also investigated. The sensor was stretched up to 6% strain at the rate of 1.2% s-1, and then released back to the initial position at the same rate (FIG. 5D), exhibiting a low hysteretic behavior, which may be attributed to the elastic deformation of the sensor materials. [65] When the sensor was attached to the surface of a growing balloon 50, the value of $\Delta R/R$ increased due to the stretching of the graphene strip 10 (FIG. 5E). When the balloon 50 was in a temporarily static state, the sensor 10 resistance remained constant. The tape-based strain sensor 10 was therefore capable of monitoring strain variations at an object's surface.

Figure 5F:
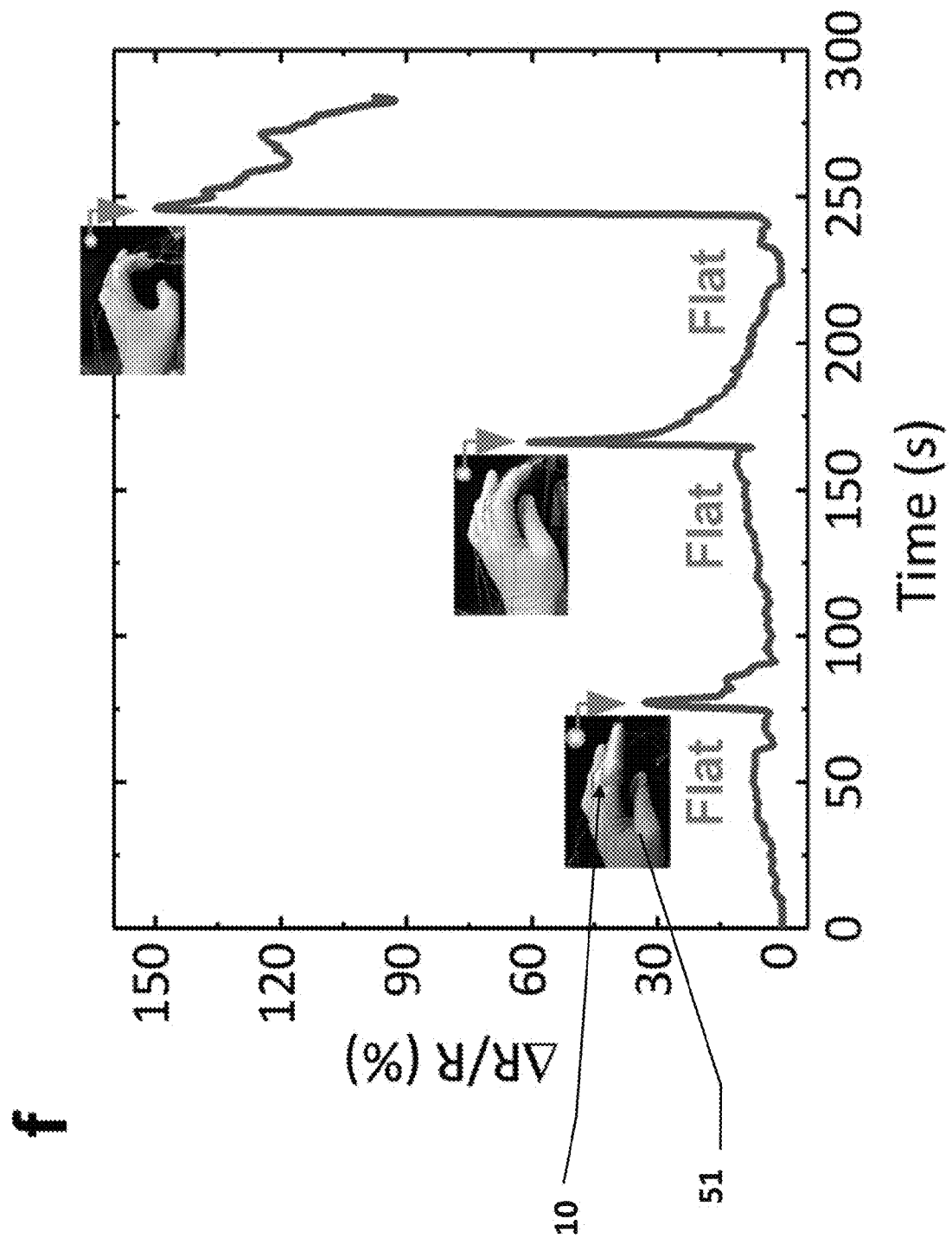

In another test, the same type of sensor 10 was attached to the middle joint of an index finger 52 to measure the tensile strain formed during finger bending (FIG. 5F). As the degree of bending increased from 5° to 90°, the value of $\Delta R/R$ of the sensor 10 increased from 33.8 to 147.5%. After the finger 52 returned to its original position, the sensor resistance immediately resumed its initial value, demonstrating good reversibility of the sensor response.

2.2.2. On-Tape Pressure Sensors

Figure 6A:
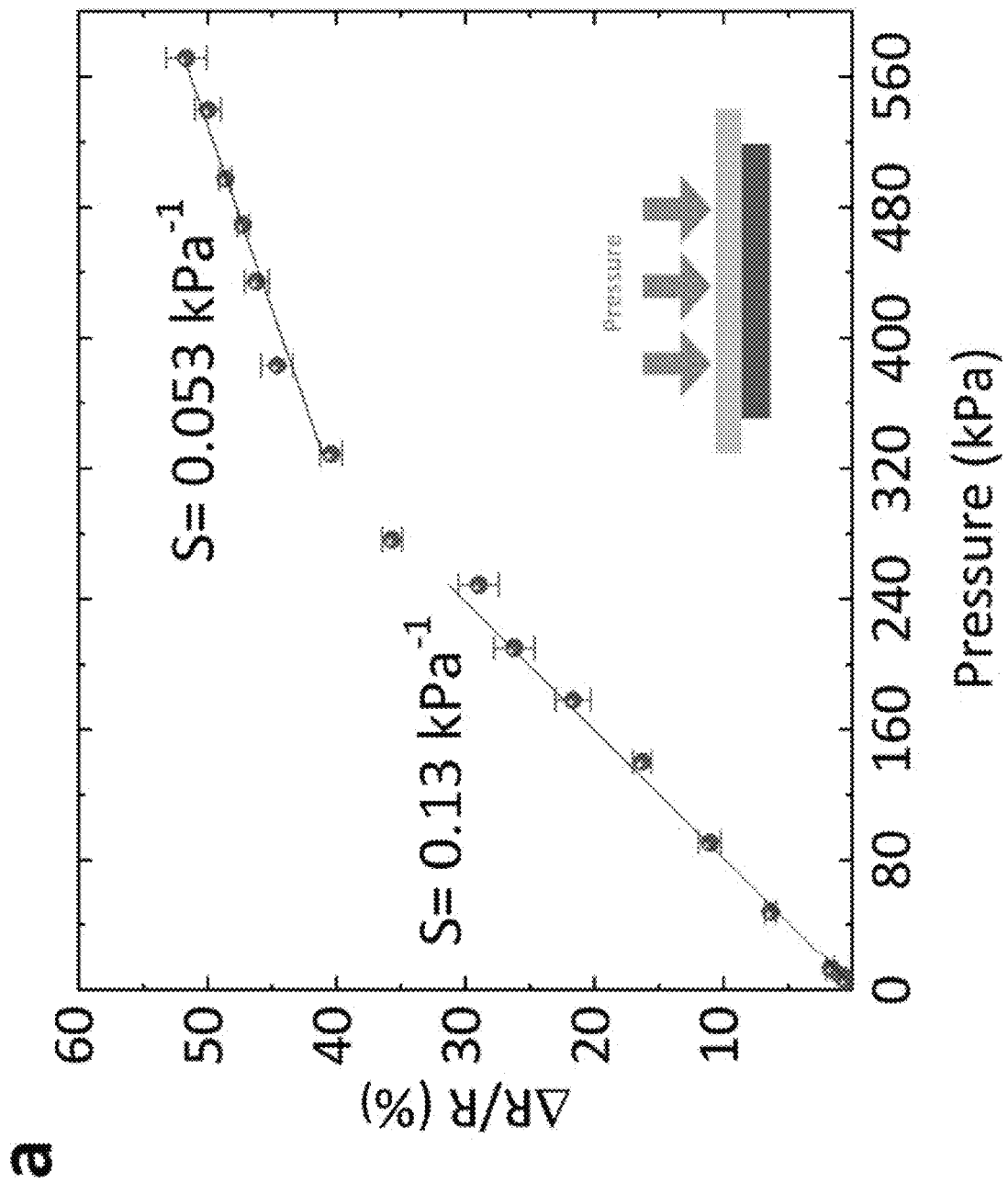
Figure 6B:
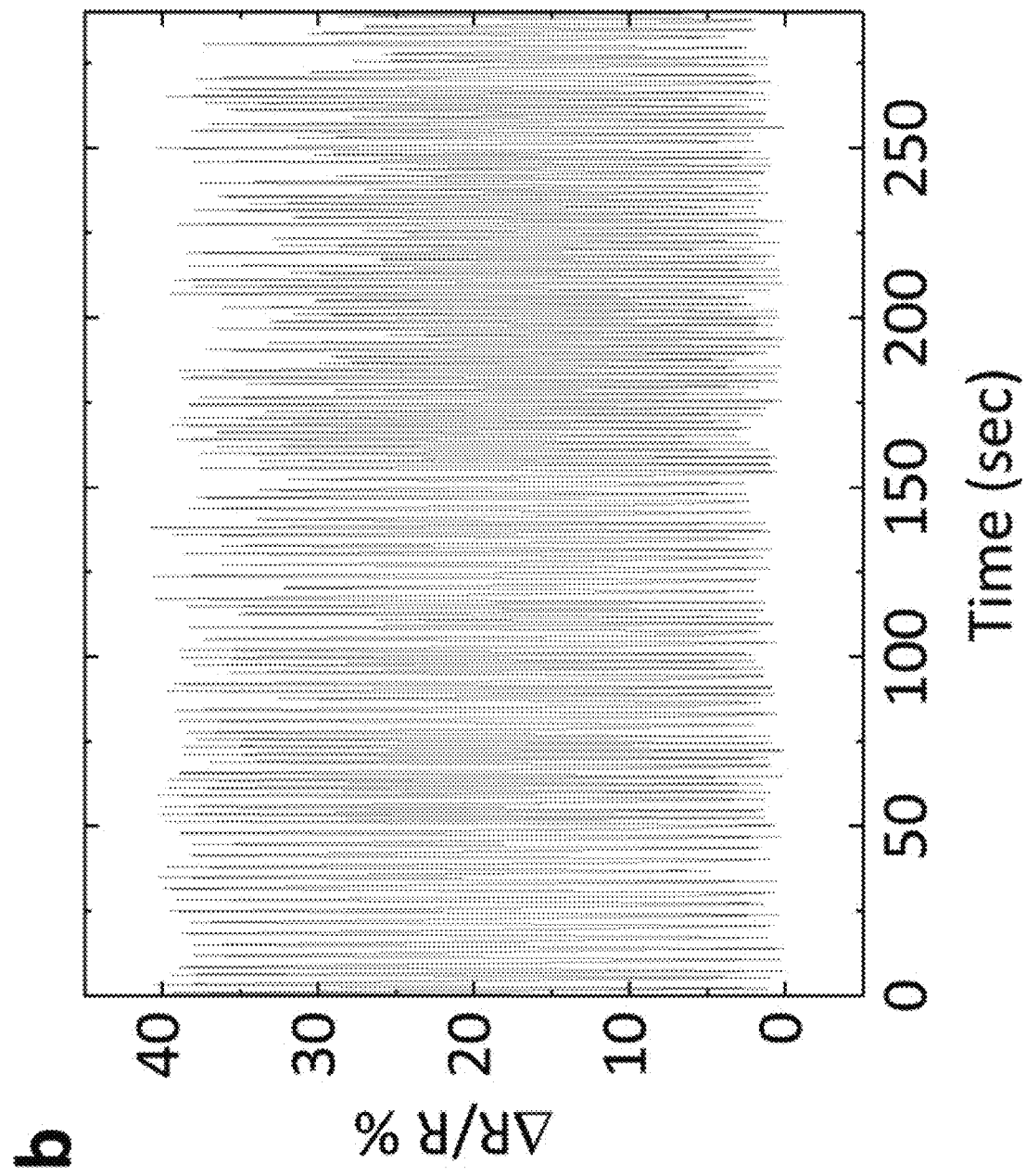
Figure 6C:
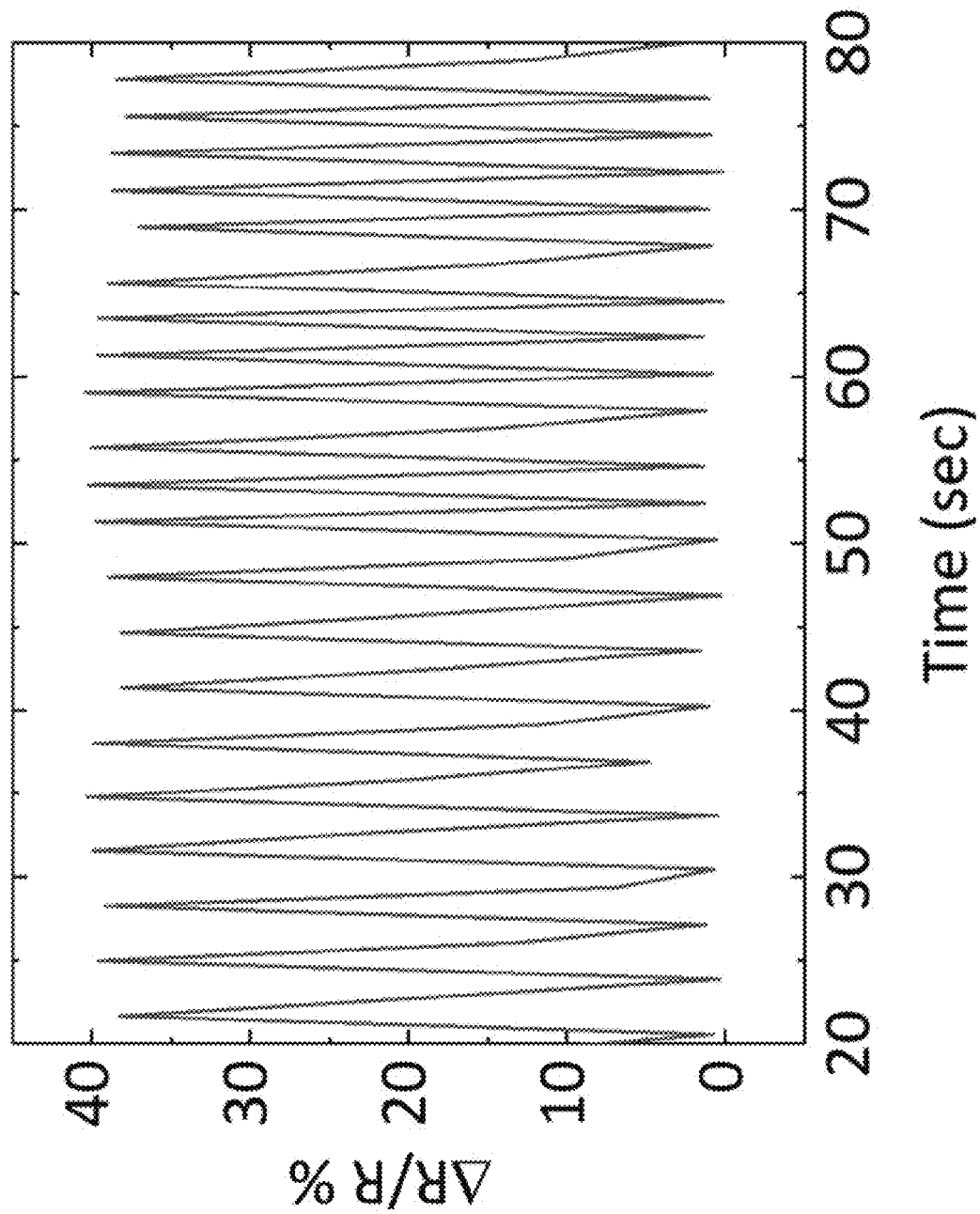
Figure 6D:
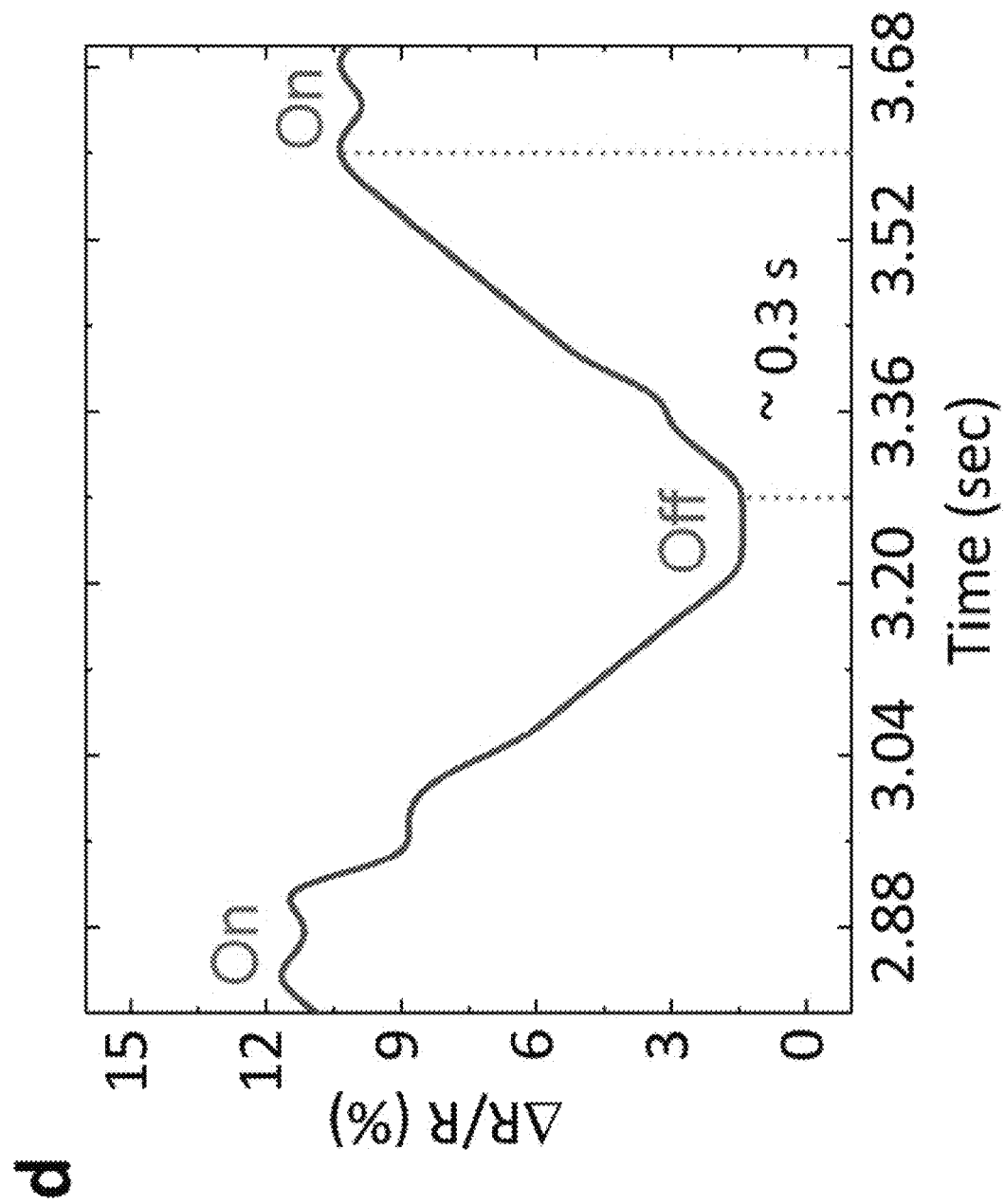

The above-mentioned strain sensor was adopted as an on-tape pressure sensor 10 in this demonstration. FIG. 6A shows that the $\Delta R/R$ value produced by the sensor increased with increasing pressure applied normal to the surface of the sensor. Based on the slopes of the linear fitting curves in different pressure ranges, the sensitivity of the sensor was found to be S=0.13 kPa$^{-1}$ for applied pressures below 300 kPa, and S=0.053 kPa$^{-1}$ in a higher pressure range up to 575 kPa. To verify durability of the sensor, the device was loaded (pressure normal to the sensor surface: 330 kPa) and unloaded for 100 cycles. No obvious degradation of the sensor response was observed after the testing (FIGS. 6B, C). In addition, the sensor exhibited a response time of ≈0.3 s (FIG. 6D).

Figure 6E:
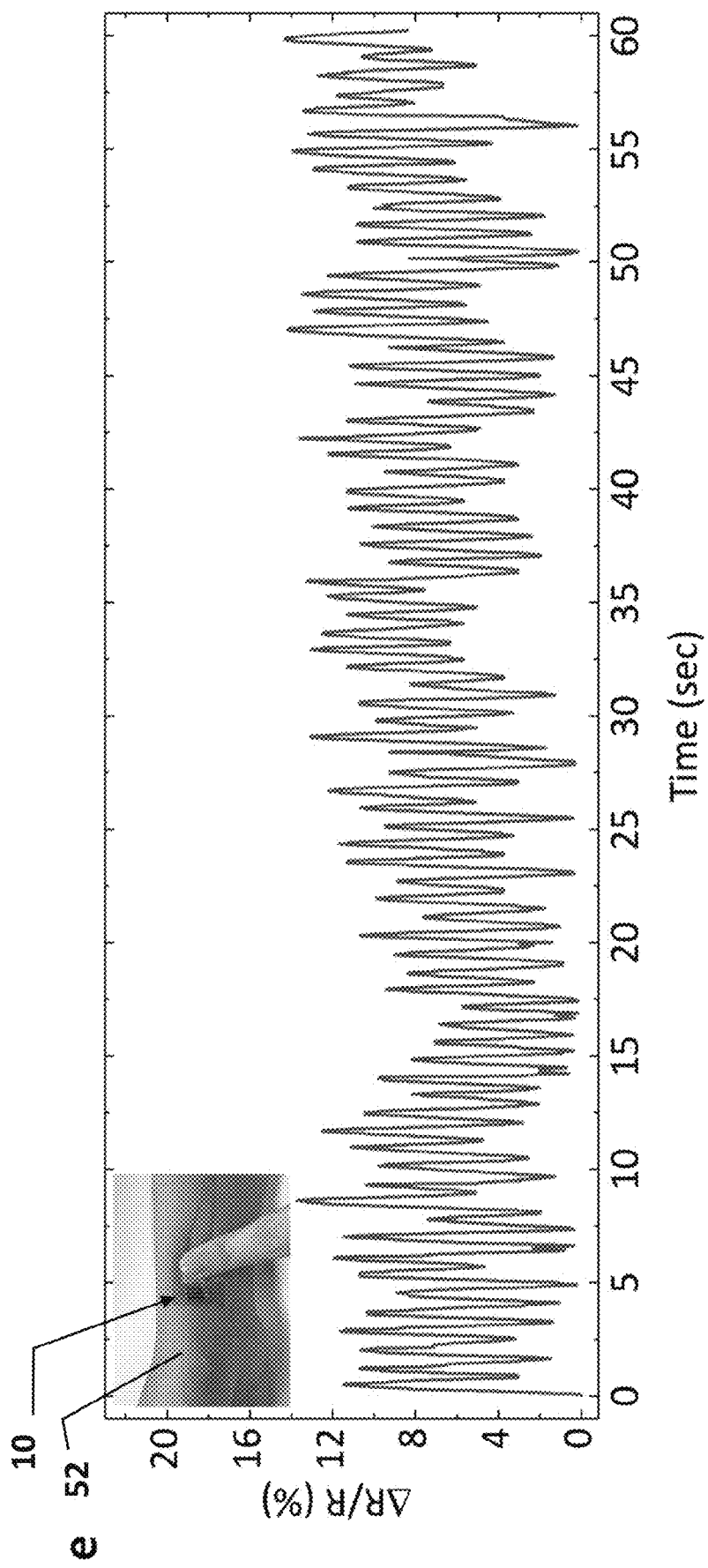
Figure 6F:
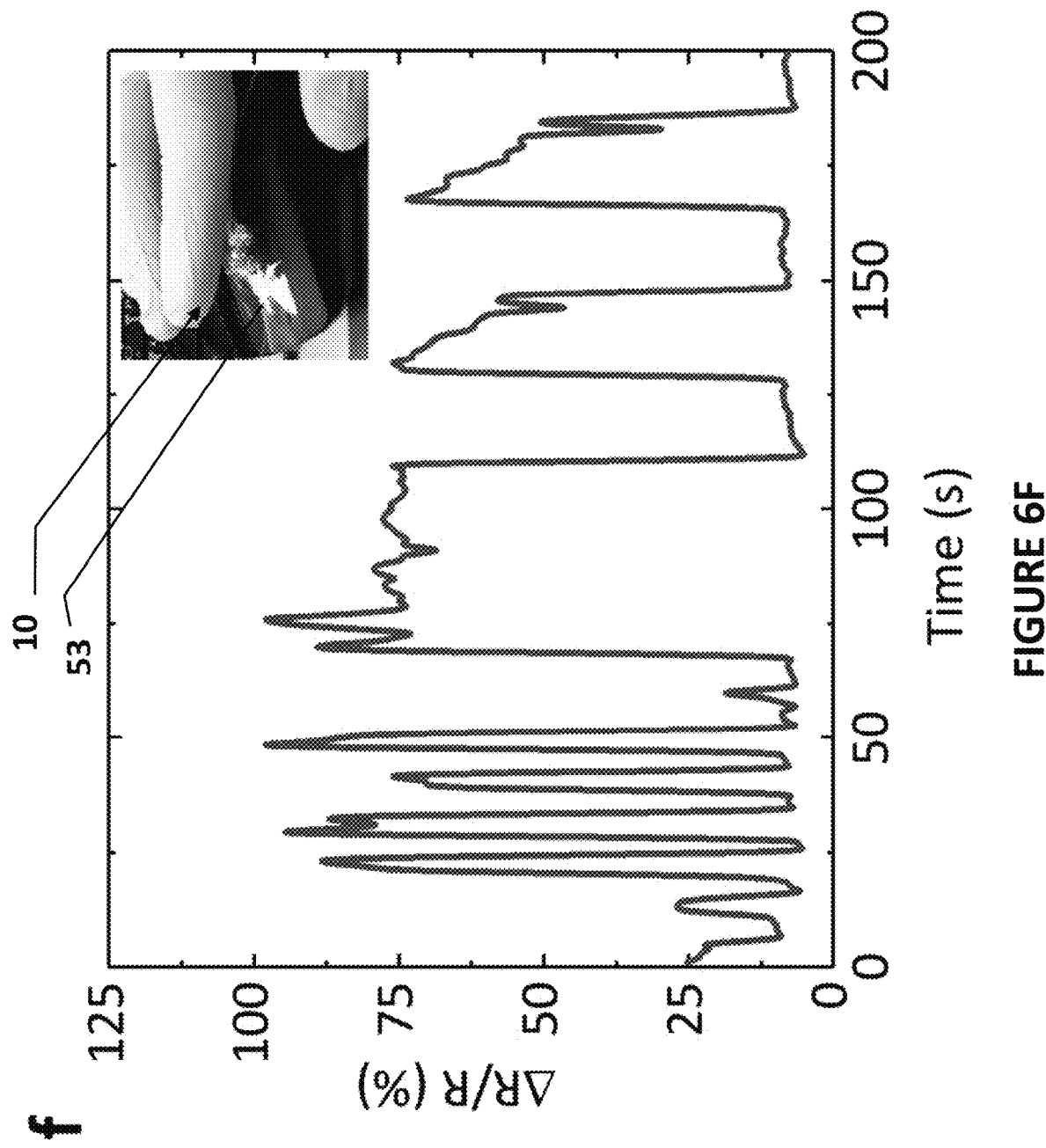

This sensor 10 was used to measure the pulse in the wrist 52. FIG. 6E shows that the wrist pulses, 75 beats min-1, were counted via the time-varying relative resistance changes. Next, the sensor 10 monitored repetitive finger clicking of a computer mouse 53. When the mouse was clicked, the $\Delta R/R$ value of the interacting sensor increased. FIG. 6F demonstrates that the sensor continuously tracked various clicking pressures and frequencies.

Figure 6G:
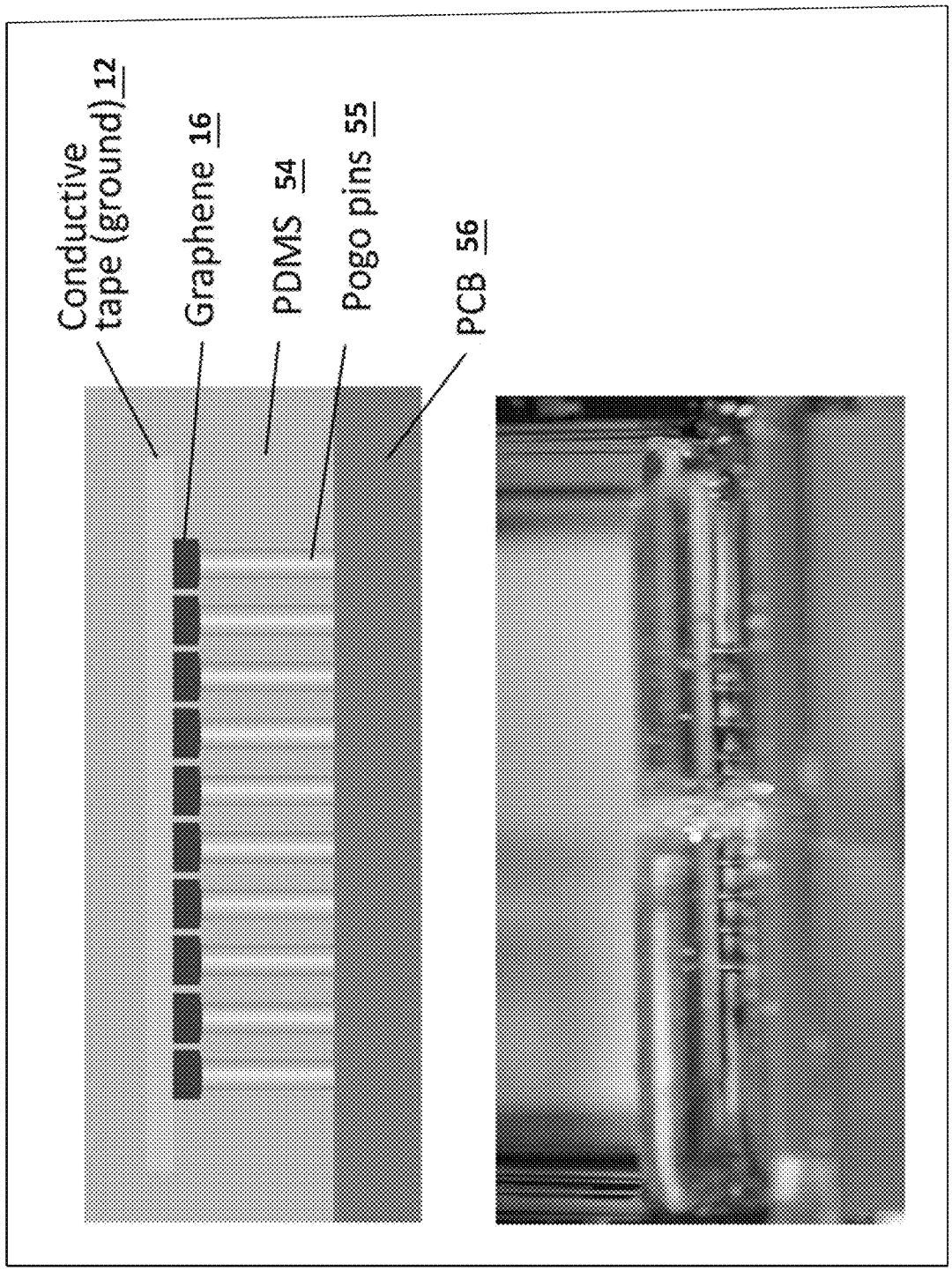

As another example application, an array of 10×10 round-shaped graphene sensors 16 was formed on 3M electrically conductive tape 12 (Conductive adhesive transfer tape 9707) (FIG. 6G). Each sensing element 16 had a diameter of 1 mm, a thickness of ≈10.3 μm, and a pitch of 1.5 mm. Because this type of tape could sustain temperatures up to 85° C., [66] the transferred graphene was further annealed in air at 80° C. for 4 h to reduce its sheet resistance to 4.05±0.18 kΩsq$^{-1}$. These sensing elements 16 were connected to an external detection circuit through an array of 10×10 vertical pogo pins 55 (No.

Figure 6H:
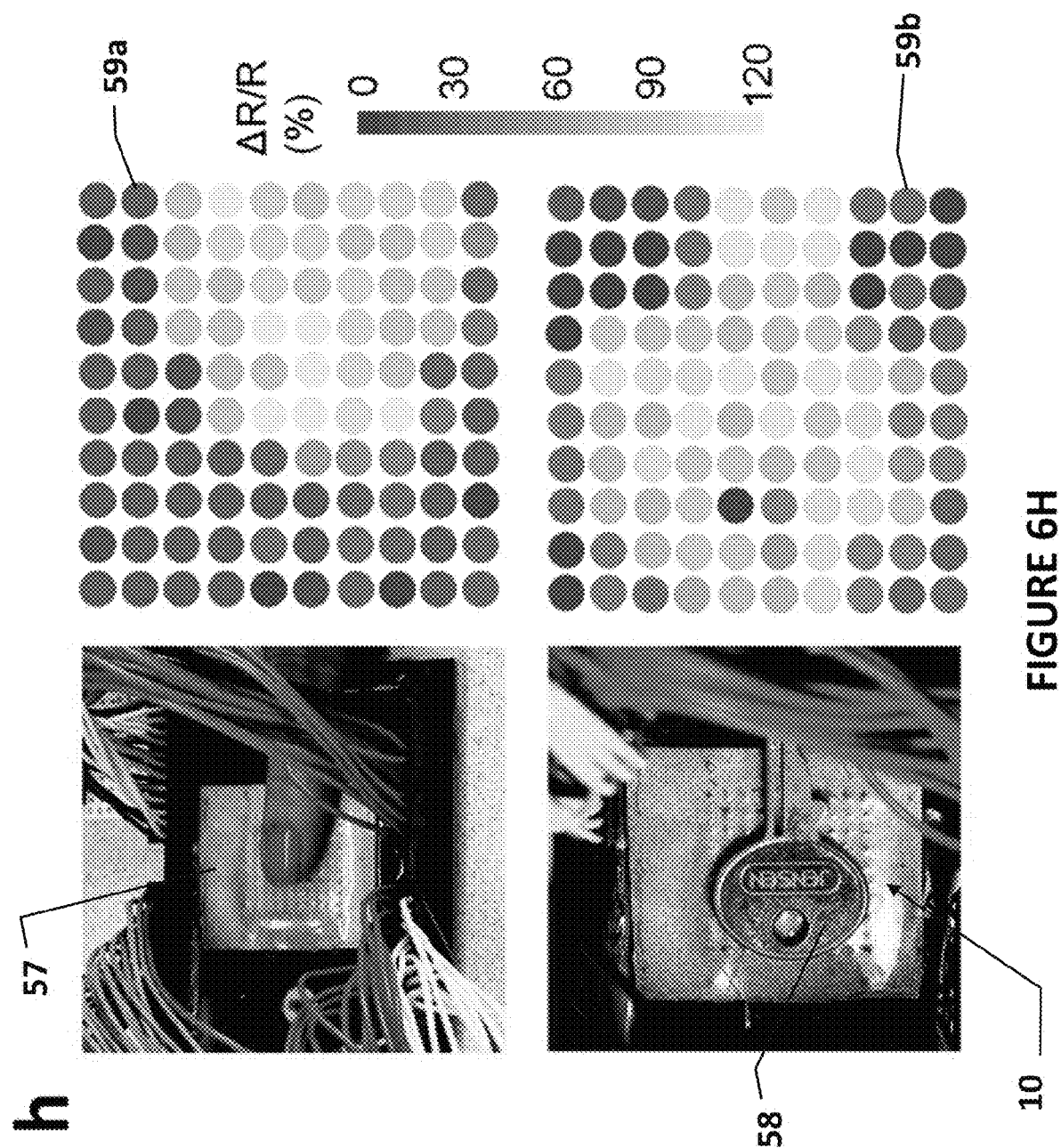

575-09510152071, Mouser Electronics) formed on a printed circuit board 56 and arranged in the same manner as the sensing elements (FIG. 6g). The conductive tape served as a common ground for the sensing elements. To facilitate pressure application to the sensor array, the tape and pogo pins were embedded in a PDMS layer 54. After applying external pressure, changes in resistance were recorded by a multimeter through a multiplexer. FIG. 6H shows that when a finger 57 was pressed or a key 58 was positioned on the surface of the device, the embedded sensor array 16 could monitor its interaction with the object and identify the shape and pressure (or resistance) profile of the object (see display 59a associated with the finger 57 press, and display 59b associated with the key impression).

2.2.3. Smart Glove

Figure 7A:
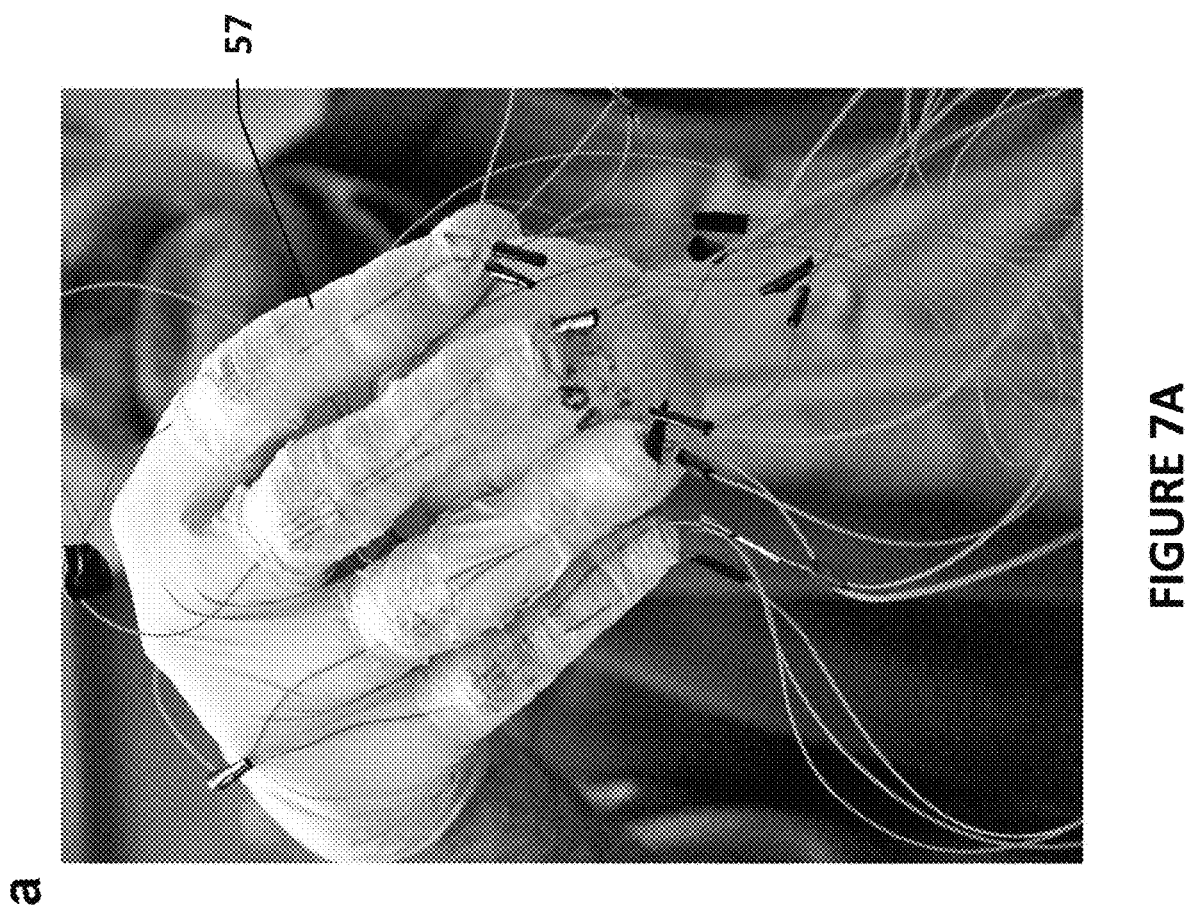
Figure 7B:
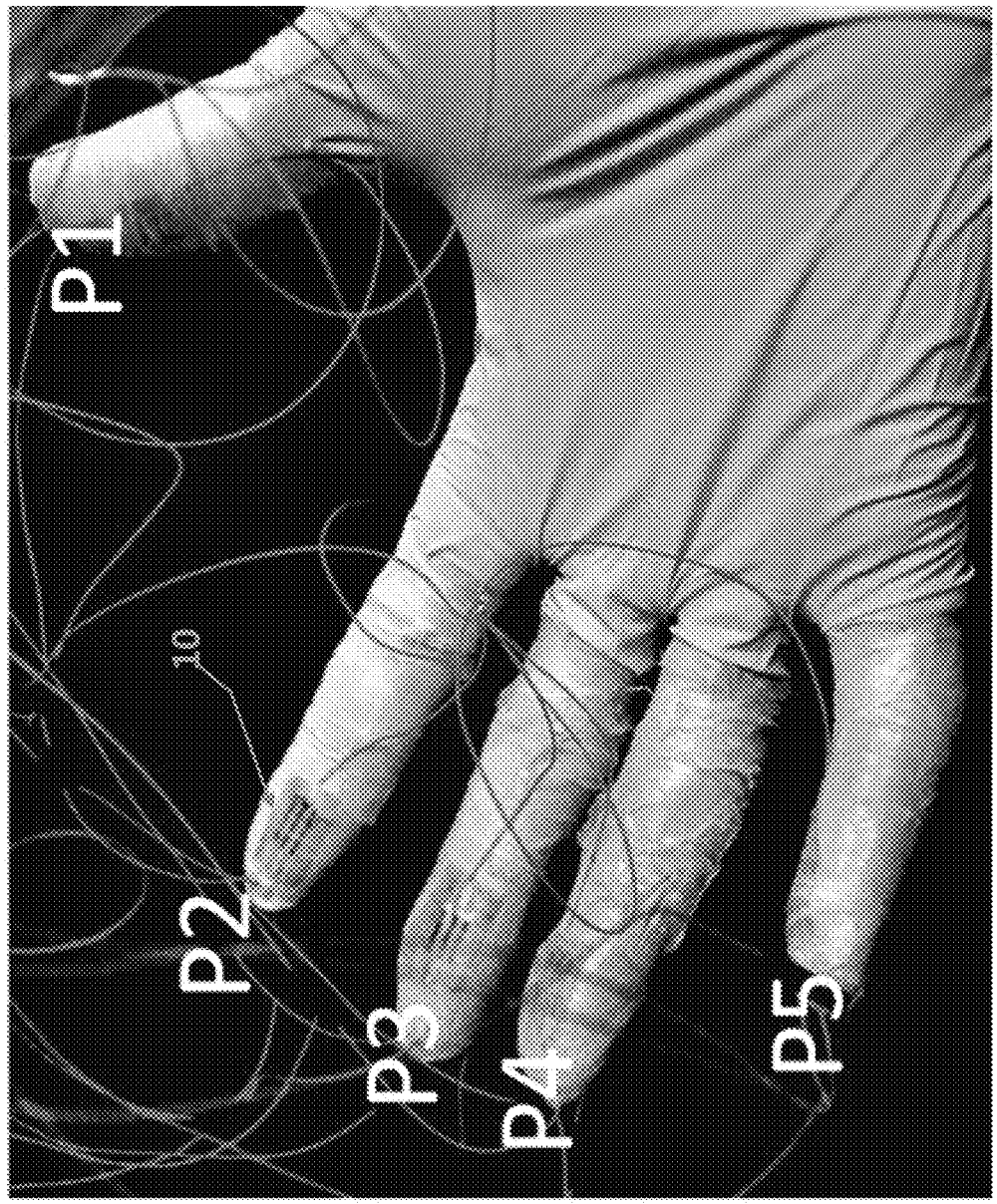
Figure 7C:
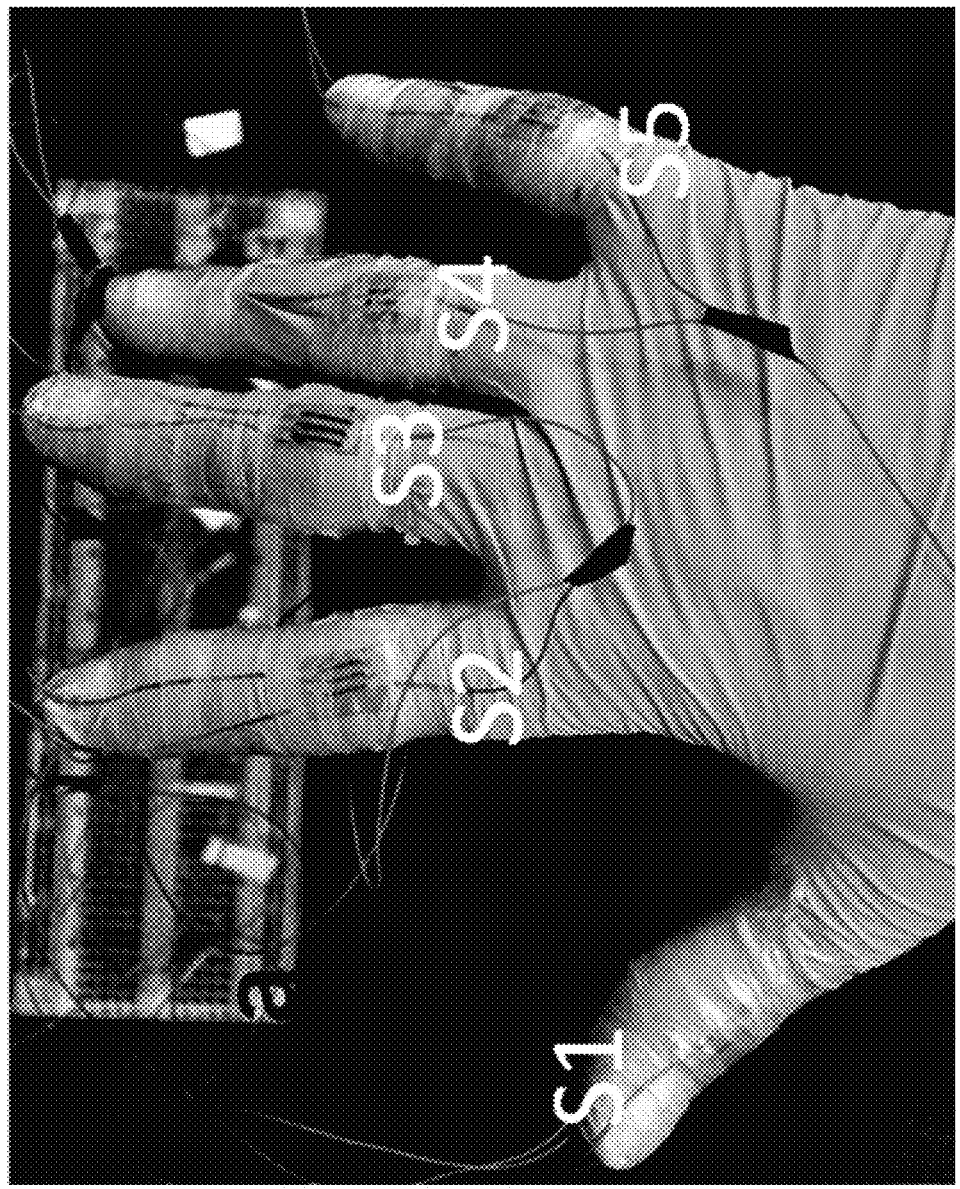
Figure 7D:
Figure 7E:
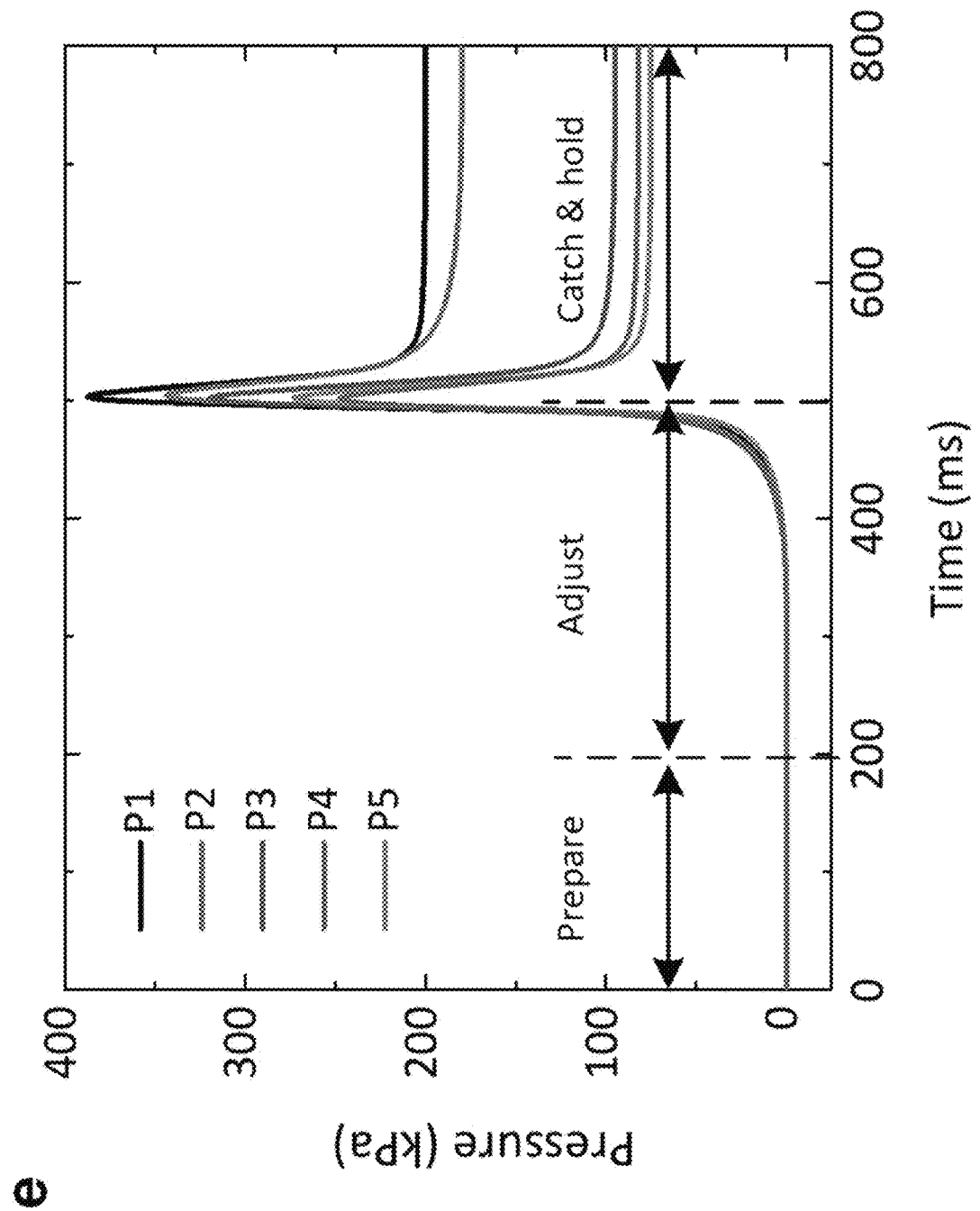
Figure 7F:
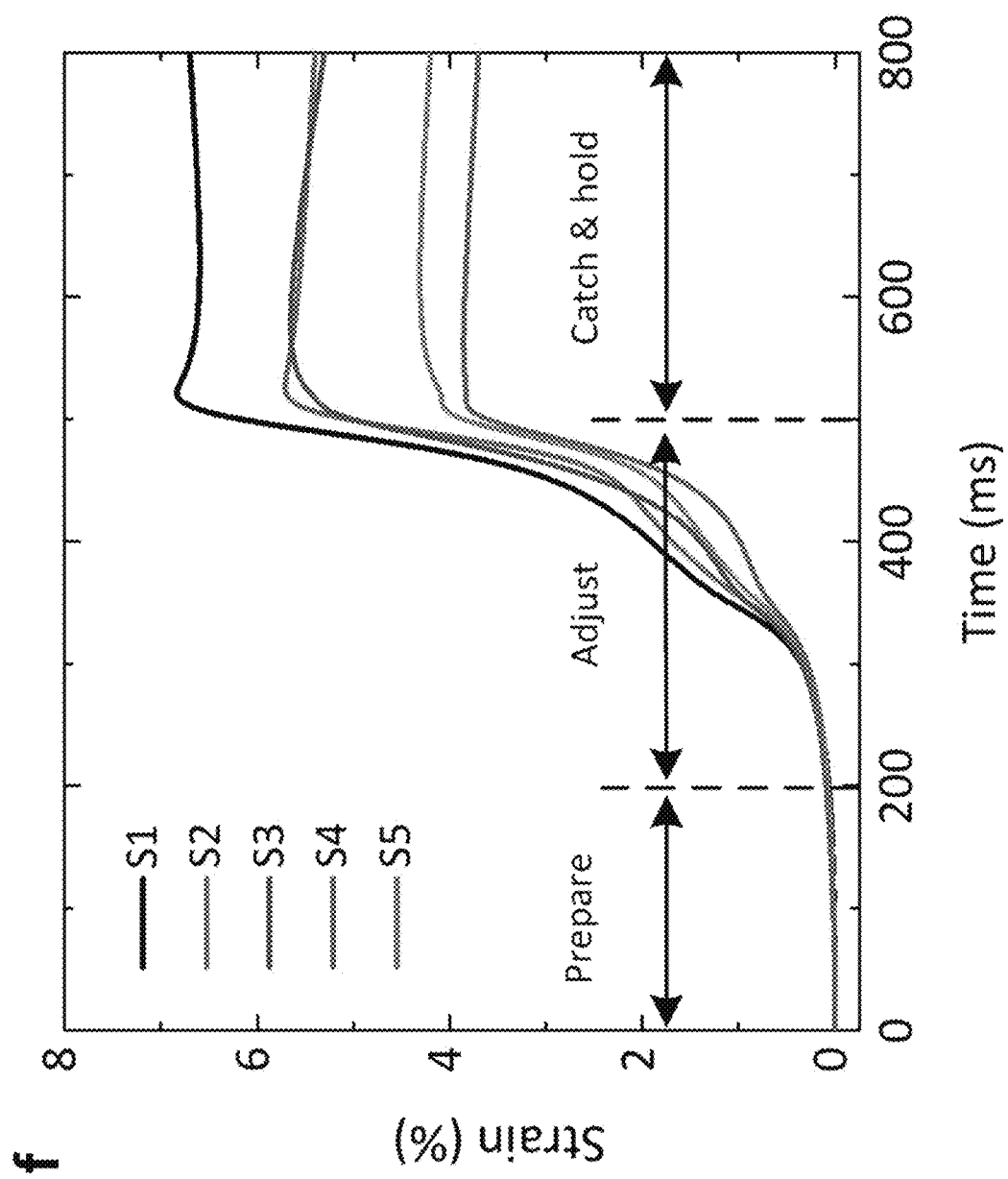

FIG. 7A depicts a smart glove 51 equipped with on-tape strain and pressure sensors 10 for monitoring mechanical response of fingers when interacting with an object. Specifically, each finger was equipped with a pressure sensor at its fingertip and a strain sensor 10 at the top of the finger joint, respectively (FIGS. 7B, C). These sensors 10 enabled real-time monitoring of changes in important mechanical parameters due to hand movements. As an example, the glove 51 was worn while catching a tennis ball bounced from a hard floor (FIG. 7D). The pressure (FIG. 7E) and strain (FIG. 7F) variations during preparing, adjusting, catching, and holding were obtained by the smart glove. As the ball bounced upward, the fingers adjusted to bend more, increasing the tension on the sensors. When the ball was about to reach the palm, the fingers acted to catch the ball, producing immediate increases in the applied pressure. The flexibility of these tape-based graphene sensors allowed for conformable contact with the fingers. Such a smart glove would be useful in measuring hand mechanical function and control in many applications, such as providing real-time data streams for medical rehabilitation therapies and human-computer interaction.

2.2.4. On-Tape Plant Leaf Sensors

Figure 8A:
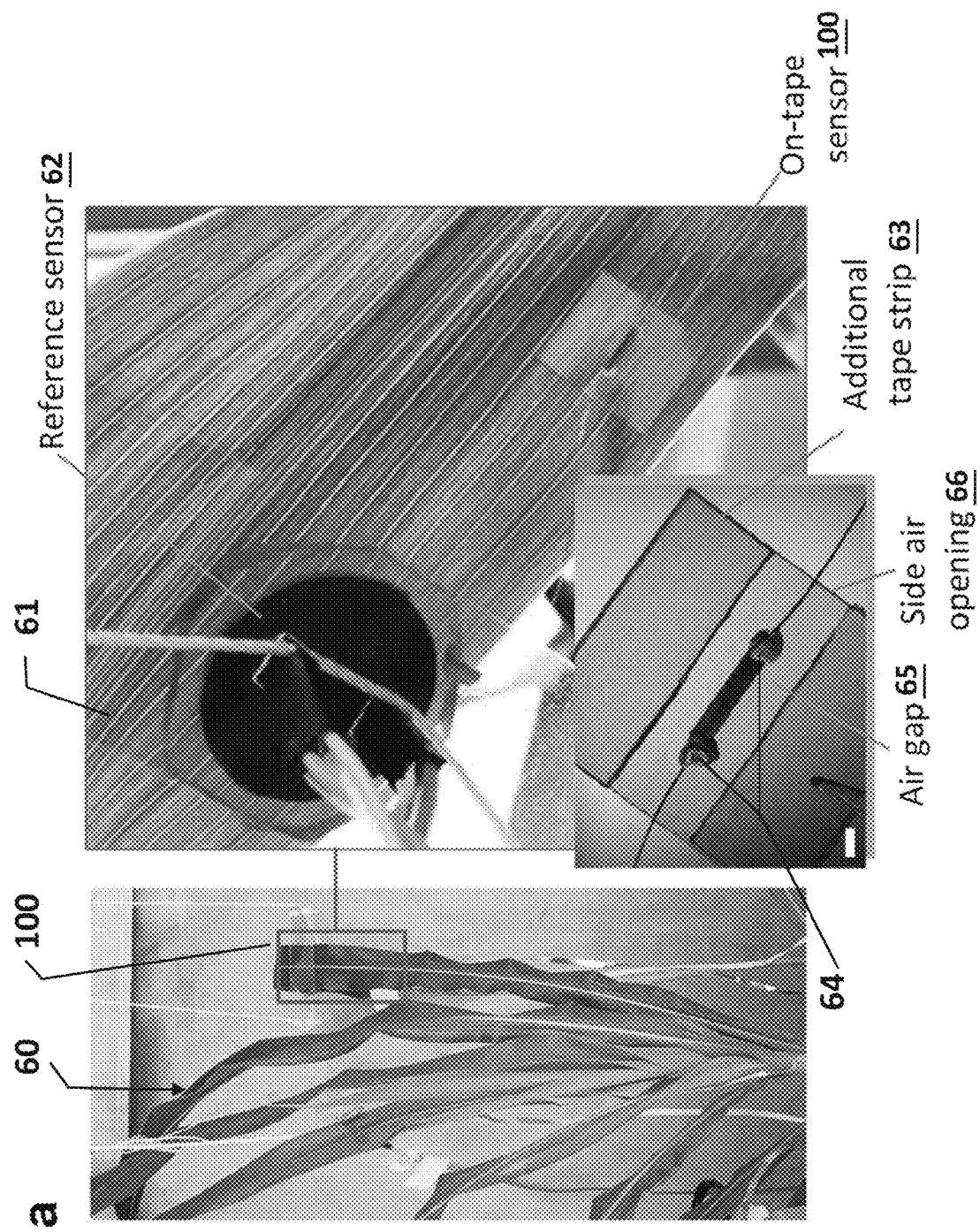
Figure 8B:
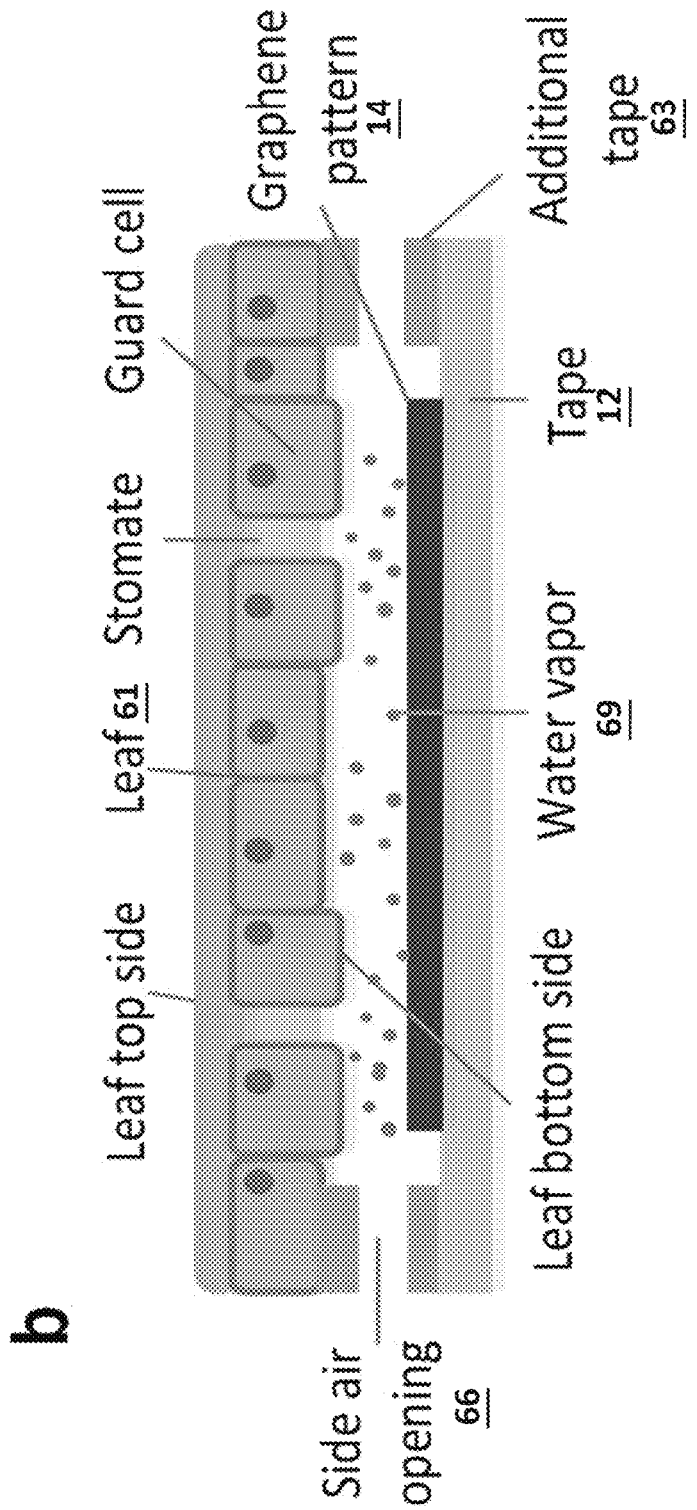
Figure 8C:
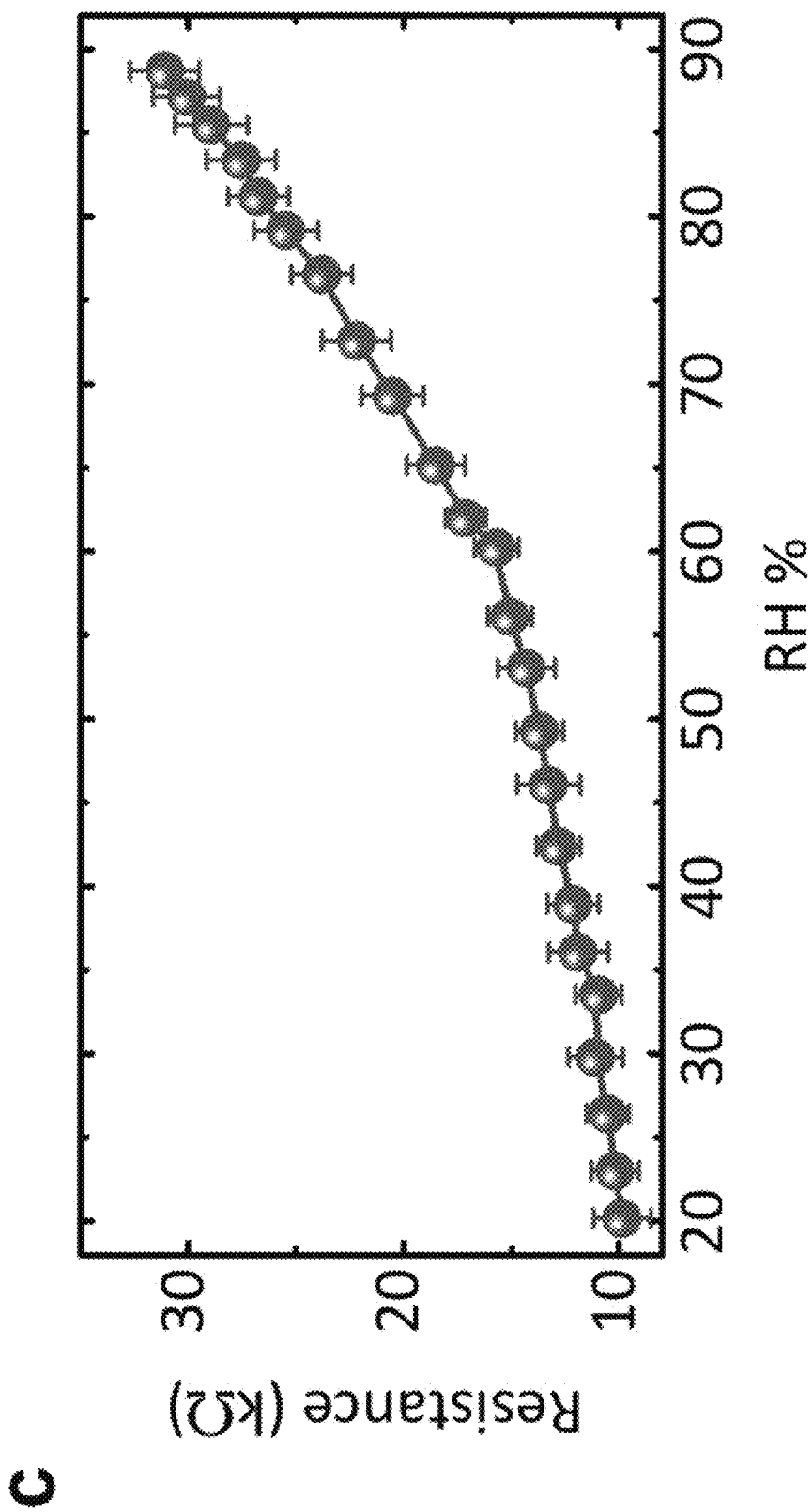
Figure 8D:
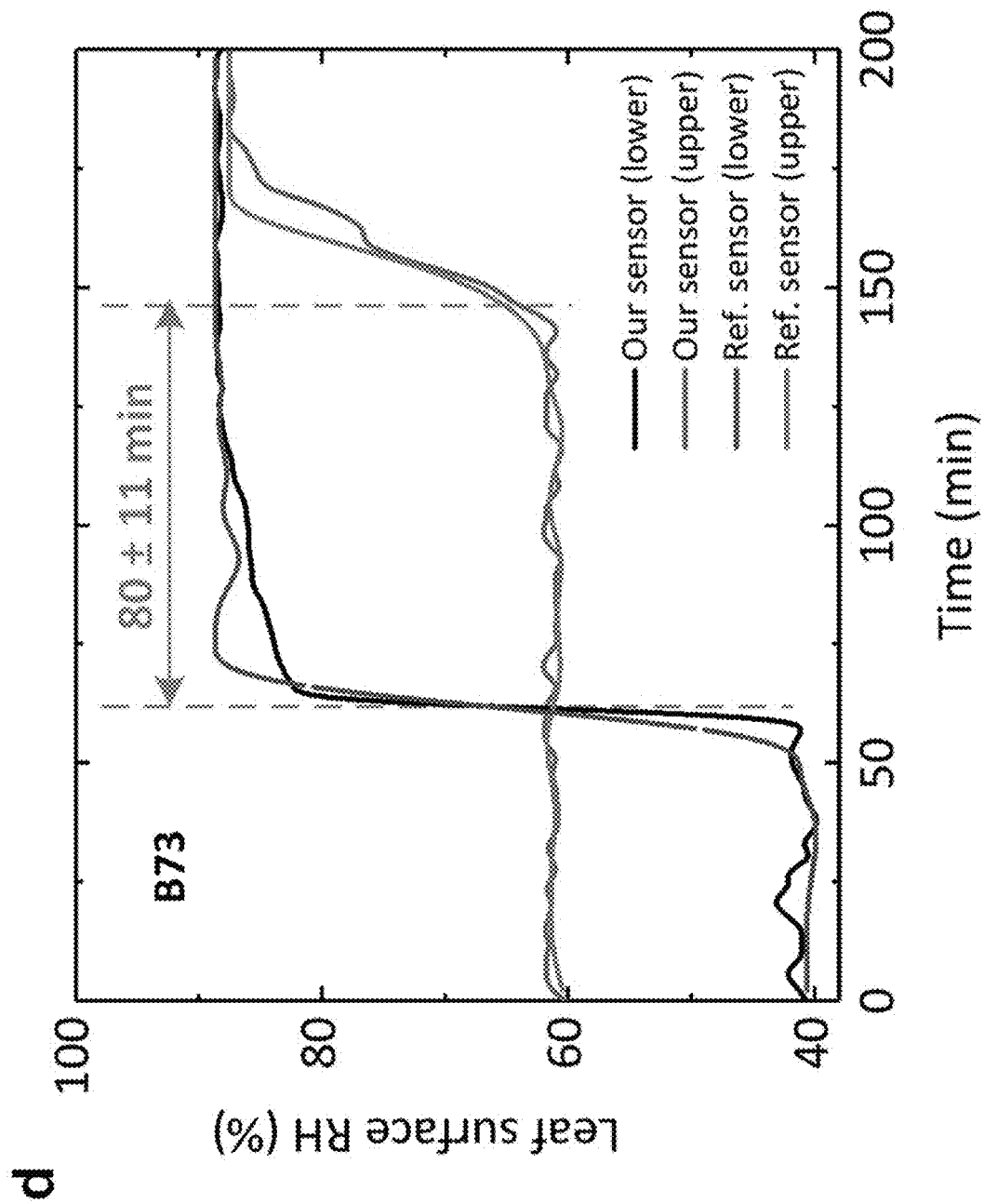

Water uptake by roots, transport through the xylem, and transpiration from the stomata of leaves to the atmosphere are an important physiological process in plants. Using tape-based graphene RH sensors, we demonstrated a unique capability to estimate the time required for water movement within a plant from the roots to the lower and upper leaves (FIG. 8A). When the stomata are open, water vapor escapes from the leaves, increasing the local humidity level on the leaf surface (FIG. 8B). Consequently, by installing multiple RH sensors on different leaves to dynamically monitor RH variation at the leaf surfaces, it is possible to track the key time points at which significant water loss occurs at the leaves, thus quantifying water transport time via the xylem from the roots to each of the measured leaves. The RH sensors were structured as graphene strips (6 mm length, 800 µm width, and 10.3 µm thick-ness) transferred onto the polyimide tape and are the same as those used in the above-mentioned pressure and strain sensing applications. The sensing mechanism is based on changes in the electrical resistance of graphene in different moisture environments. FIG. 8C shows the resistance response of the fabricated sensor exposed to different RH levels at room temperature. To facilitate the installation of the sensor onto the leaf surface, two additional tape strips (acrylic adhesive; No. 6915001 from Gorilla) were adhered to the two sides of the graphene pattern (see the inset of FIG. 8C). This also created a 170 µm thick air gap between the sensor surface and the leaf, as well as two side openings that allow air exchange between inside and outside of the gap space for avoiding accumulation of water vapor. The air gap was determined by the thickness of the additional tape strips. FIGS. 8D, E describes real-time monitoring of RH using the sensors installed on the back surfaces of the fourth and ninth leaf of two-month old maize plants. Here, one type of plant (FIG. 8D) was inbred line B73. [67] The other type (FIG. 8E) was a mixed genetic stock (having a more complicated pedigree in which the female parent was a hybrid with no close relationship to B73, and the male parent was in a B73 background; they were grown in Dr. Patrick Schnable's lab at Iowa State University). The testing was initiated 15 min before irrigation. After irrigation, for B73, the lower and upper sensors exhibited a resistance increment and thus an increase in RH at 55 and 135 min, respectively. Similarly, for the mixed genetic stock, the sensor outputs of the show that the lower and upper leaves had an increase in RH at 82 and 110 min, respectively. Therefore, in both the B73 plants and plants with mixed genetic backgrounds, it took less time for water to be transported from the roots to the fourth leaf than from the roots to the ninth leaf. Significantly, these two genetic stocks exhibited differences in the delta between the fourth and ninth leaves (80±11 min, mean±standard deviation obtained from the measurements on three plants for B73 versus 28±10 min, mean±standard deviation obtained from the measurements on three plants for the plants with a mixed genetic background). Because water transport is a critical process for plants, the on-tape RH sensor technology would be useful to select plants with a desirable water transport character or improved tolerance to increasing water stress, a major objective of crop breeding.

The above demonstrations provide only a few application examples of using tape-based flexible sensors, and many other graphene sensors could be designed and manufactured on tape for use in a variety of emerging applications. For example, the graphene pressure and strain sensors could be fastened to the surfaces of mechanical and infrastructure systems for structural health monitoring purposes. By functionalizing the patterns of graphene-based nanomaterials on the tape with an enzyme substrate or a receptor ligand that respond to a specific receptor or enzyme, or by transferring materials already functionalized inside the PDMS negative features onto a tape, it would be possible to develop many wearable and disposable biological and chemical sensors on tape for applications in biomedical diagnostics (e.g., sweat glucose and electrolyte sensing), environmental monitoring (e.g., gas sensing), and agricultural monitoring (e.g., nutrient and pesticide sensing). In addition, this fabrication approach allows formation of high-resolution patterns on the surfaces of versatile tapes as long as their free surface energies are different enough to enable strong adhesion to one another. This advantage, in conjunction with the ability to control the patterns along three dimensions with high spatial resolution, would further extend the application potential of this method. Further work will aim at using the presented technology to develop on-tape sensors with different nanomaterials. We believe that this technology will open a new route for low-cost, scalable, and roll-to-roll production of various types of nanomaterials-based sensors.

3. Conclusion

In summary, a novel tape-based graphene patterning and transfer approach has been developed. It is simple and effective and has potential to support realization of roll-to-roll production of various graphene sensors. Once PDMS negative patterns are formed via conventional soft lithography, only adhesive tapes are required to produce graphene patterns with feature resolution of a few micrometers. The method can be applied to many tapes to realize various flexible sensors, such as the demonstrated wearable graphene-based sensors for mechanical and RH sensing on surfaces of humans and crop plants.

4. Experimental Section

Graphene Suspension Preparation: Dispersion of graphene nanoplatelets in n-butyl acetate (total graphene content: 23 wt %; SKU: UHC-NPD; Graphene Supermarket, Calverton, NY) was heated on a hotplate at 85° C. until it all became dried due to evaporation of the solvent from it. The average thickness of graphene nanoplatelets is ≈7 nm. [71] Subsequently, aqueous suspensions of graphene nanoplatelets (20 mg mL-1) were prepared by thoroughly dispersing 20 mg of the obtained graphene nanoplatelet powder in 1 mL of a mixed solution of ethanol and deionized water at a ratio of 7:3 (vol/vol), followed by sonication at room temperature for 400 min. Here, 20 mg mL-1 concentration of the obtained graphene dispersions was chosen because it allowed easy spreading of the solution, while forming a continuous film over the PDMS surface. In addition, the specific 7:3 (vol/vol) ethanol-to-water volume ratio was chosen to allow sufficient dispersion and maximum concentration of graphene [58] (see the graphene dispersions prepared at different volume ratios in FIG. S3, Supporting Information).

PDMS Substrate Fabrication: The PDMS negative patterns used here were fabricated using soft lithography. In this step, a silicon wafer with photoresist SU-8 (3050; Micro-Chem, Westborough, MA) was spin-coated to produce different thicknesses by adjusting rotation speed and duration. The wafer was then baked at 65° C. for 5 min and 90° C. for 1 h. Subsequently, the wafer was exposed to an ultraviolet light with photomask, baked at 90° C. for 30 min, and developed to form a master mold for the microfluidic channels. Following that, a precursor solution of PDMS was prepared by mixing Sylgard 184 Silicone Elastomer base and curing agent (Dow Corning, Auburn, MI) at a weight ratio of 10:1, and then degassed in a vacuum desiccator for 20 min. Finally, it was poured on the master mold and thermally cured at 65° C. for 2 h on a hotplate. Finally, the cured PDMS containing negative patterns were peeled from the master mold.

D2SP and ST Processes: The D2SP process was used to pattern graphene structures in the negative features on the PDMS substrate (FIG. 1A, subparts a-e). First, the PDMS substrate was horizontally placed on a hotplate. A 3 mm high, 50 mm diameter acrylic plastic ring was then placed on the edges of the PDMS substrate to confine graphene dispersions on the substrate surface. Next, the graphene dispersions (20 mg mL-1) were loaded into the plastic ring using a medical syringe. The volume of graphene dispersions per unit surface area was 100 μL cm-2. The loaded graphene solution was then heated on the hotplate at 90° C. for 5 min, thus forming a casted graphene film. Subsequently, Scotch tape with synthetic rubber adhesive (Scotch Heavy Duty Shipping Packaging Tape) was manually applied and stick to the PDMS top surface. As the tape was then peeled, the graphene in the nonpatterned areas was removed from the PDMS surface. The D2SP process was repeated multiple times until the PDMS top surface was cleaned. Therefore, the graphene patterns (thickness: 1.45 μm) were obtained in the negative features on the PDMS surface, without any residues left on the nonpatterned areas. To increase the thickness of graphene patterns, the D2SP process was repeated. For example, to obtain 10.3 μm thick graphene patterns, one needs to repeat the D2SP process for seven times.

Next, the ST process was conducted to transfer the formed graphene patterns from the PDMS surface onto a final tape. In this step, the final tape was applied and stick to the PDMS surface. A minor pressure was applied to achieve a conformal contact between the tape and the graphene flakes filled in the negative surface features. Subsequently, the tape was manually peeled from the PDMS substrate, and thus the graphene patterns were stick and transferred onto the surface of the tape.

To increase electrical conductivity of the transferred graphene patterns, thermal annealing was conducted at 250° C. for 180 min in air (Thermolyne Benchtop Muffle Furnace; Thermo Scientific, Waltham, MA).

X-Ray Photoelectron Spectroscopy Analysis: The XPS measurements were performed using a PHI ESCA 5500 instrument (Perkin-Elmer Co., MN). Each sample was irradiated with 200 W unmonochromated Al Kα X-rays. The pass energy was set at 188 eV for survey scans and 47 eV for narrow scans.

Thickness Measurement for Graphene Patterns in PDMS Channel: The thickness of graphene formed in the PDMS channel was measured using a surface profilometer (XP-100; Ambios Technology, Santa Cruz, CA). First, the profilometer was used to measure the surface profile and depth (H1) of the PDMS channel. After the D2SP process was completed, the graphene structures were formed in the channel. The profilometer was then used to determine the new depth (H2) of the channel filled with graphene. Therefore, the thickness of the graphene patterns was calculated as H1–H2. In this study, informed and signed consent was obtained from the participants of the experiments performed on human subjects.

Supporting Information

REFERENCES (EACH OF WHICH IS INCORPORATED BY REFERENCE HEREIN IN ITS ENTIRETY)

[1] A. R. Madaria, A. Kumar, F. N. Ishikawa, C. Zhou, Nano Res. 2010, 3, 564.
[2] F. E. Wiria, C. L. Tham, A. S. Subramanian, J. N. Tey, X. Qi, C. K. Cheng, B. Salam, J. Solid State Electrochem. 2016, 20, 1895.
[3] H. Kizil, M. O. Pehlivaner, L. Trabzon, Adv. Mater. Res. 2014, 970, 132.
[4] C. Wang, J. Chien, K. Takei, T. Takahashi, J. Nah, A. M. Niknejad, A. Javey, Nano Lett. 2012, 12, 1527.
[5] Y. Wang, R. Yang, Z. Shi, L. Zhang, D. Shi, E. Wang, G. Zhang, ACS Nano 2011, 5, 3645.
[6] G. Schwartz, B. C.-K. Tee, J. Mei, A. L. Appleton, D. H. Kim, H. Wang, Z. Bao, Nat. Commun. 2013, 4, 1859.
[7] Y. Zheng, Z. He, Y. Gao, J. Liu, Sci. Rep. 2013, 3, 1786.
[8] F. N. Ishikawa, H.-K. Chang, K. Ryu, P.-C. Chen, A. Badmaev, L. G. De Arco, G. Shen, C. Zhou, ACS Nano 2009, 3, 73.
[9] Y.-H. Lee, J.-S. Kim, J. Noh, I. Lee, H. J. Kim, S. Choi, J. Seo, S. Jeon, T.-S. Kim, J.-Y. Lee, J. W. Choi, Nano Lett. 2013, 13, 5753.
[10] X. Pu, L. Li, H. Song, C. Du, Z. Zhao, C. Jiang, G. Cao, W. Hu, Z. L. Wang, Adv. Mater. 2015, 27, 2472.
[11] Y. H. Kim, S. J. Kim, Y.-J. Kim, Y.-S. Shim, S. Y. Kim, B. H. Hong, H. W. Jang, ACS Nano 2015, 9, 10453.
[12] G. Lu, S. Park, K. Yu, R. S. Ruoff, L. E. Ocola, D. Rosenmann, J. Chen, ACS Nano 2011, 5, 1154.

[13] H. G. Sudibya, Q. He, H. Zhang, P. Chen, ACS Nano 2011, 5, 1990.
[14] S. J. Park, O. S. Kwon, S. H. Lee, H. S. Song, T. H. Park, J. Jang, Nano Lett. 2012, 12, 5082.
[15] P. Labroo, Y. Cui, Biosens. Bioelectron. 2013, 41, 852.
[16] Y. Pang, H. Tian, L. Tao, Y. Li, X. Wang, N. Deng, Y. Yang, T.-L. Ren, ACS Appl. Mater. Interfaces 2016, 8, 26458.
[17] S. Chun, Y. Kim, H. Jin, E. Choi, S.-B. Lee, W. Park, Carbon 2014, 78, 601.
[18] K. K. Sadasivuni, A. Kafy, L. Zhai, H.-U. Ko, S. Mun, J. Kim, Small 2015, 11, 994.
[19] S. Lee, A. Reuveny, J. Reeder, S. Lee, H. Jin, Q. Liu, T. Yokota, T. Sekitani, T. Isoyama, Y. Abe, Z. Suo, T. Someya, Nat. Nanotechnol. 2016, 11, 472.
[20] M. S. Romano, N. Li, D. Antiohos, J. M. Razal, A. Nattestad, S. Beirne, S. Fang, Y. Chen, R. Jalili, G. G. Wallace, R. Baughman, J. Chen, Adv. Mater. 2013, 25, 6602.
[21] S. Han, D. Wu, S. Li, F. Zhang, X. Feng, Adv. Mater. 2014, 26, 849.
[22] M. Ali, W. Hong, S. Oren, Q. Wang, Y. Wang, H. Jiang, L. Dong, RSC Adv. 2016, 6, 67184.
[23] Q. Wang, W. Hong, L. Dong, Nanoscale 2016, 8, 7663.
[24] M. Ali, K. Mondal, Y. Jiao, S. Oren, Z. Xu, A. Sharma, L. Dong, ACS Appl. Mater. Interfaces 2016, 8, 20570.
[25] K. I. Bolotin, K. J. Sikes, Z. Jiang, M. Klima, G. Fudenberg, J. Hone, P. Kim, H. L. Stormer, Solid State Commun. 2008, 146, 351.
[26] K. Xu, K. Wang, W. Zhao, W. Bao, E. Liu, Y. Ren, M. Wang, Y. Fu, J. Zeng, Z. Li, W. Zhou, F. Song, X. Wang, Y. Shi, X. Wan, M. S. Fuhrer, B. Wang, Z. Qiao, F. Miao, D. Xing, Nat. Commun. 2015, 6, 8119.
[27] C. Lee, X. Wei, J. W. Kysar, J. Hone, Science 2008, 321, 385.
[28] B. An, Y. Ma, W. Li, M. Su, F. Li, Y. Song, Chem. Commun. 2016, 52, 10948.
[29] M. S. Mannoor, H. Tao, J. D. Clayton, A. Sengupta, D. L. Kaplan, R. R. Naik, N. Verma, F. G. Omenetto, M. C. McAlpine, Nat. Commun. 2012, 3, 763.
[30] Y. Jiao, C. W. Young, S. Yang, S. Oren, H. Ceylan, S. Kim, K. Gopalakrishnan, P. C. Taylor, L. Dong, IEEE Sens. J. 2016, 16, 7870.
[31] M. Amjadi, K.-U. Kyung, I. Park, M. Sitti, Adv. Funct. Mater. 2016, 26, 1678.
[32] T. Yang, W. Wang, H. Zhang, X. Li, J. Shi, Y. He, Q.-S. Zheng, Z. Li, H. Zhu, ACS Nano 2015, 9, 10867.
[33] J. W. Park, J. Jang, Carbon 2015, 87, 275.
[34] T. T. Tung, M. Castro, T. Y. Kim, K. S. Suh, J.-F. Feller, J. Mater. Chem. 2012, 22, 21754.
[35] C. Hou, H. Wang, Q. Zhang, Y. Li, M. Zhu, Adv. Mater. 2014, 26, 5018.
[36] D. H. Ho, Q. Sun, S. Y. Kim, J. T. Han, D. H. Kim, J. H. Cho, Adv. Mater. 2016, 28, 2601.
[37] C. Wu, J. Feng, L. Peng, Y. Ni, H. Liang, L. He, Y. Xie, J. Mater. Chem. 2011, 21, 18584.
[38] K. S. Novoselov, A. K. Geim, S. V. Morozov, D. Jiang, Y. Zhang, S. V. Dubonos, I. V. Grigorieva, A. A. Firsov, Science 2004, 306, 666.
[39] L. Wang, J. Yu, Y. Zhang, H. Yang, L. Miao, Y. Song, ACS Appl. Mater. Interfaces 2017, 9, 9089.
[40] F. Tehrani, L. Reiner, B. Bavarian, PLoS One 2015, 10, e0145036.
[41] B. Alemn, W. Regan, S. Aloni, V. Altoe, N. Alem, C. Girit, B. Geng, L. Maserati, M. Crommie, F. Wang, A. Zettl, ACS Nano 2010, 4, 4762.
[42] L. Zhang, S. Diao, Y. Nie, K. Yan, N. Liu, B. Dai, Q. Xie, A. Reina, J. Kong, Z. Liu, J. Am. Chem. Soc. 2011, 133, 2706.
[43] Z. Sun, C. L. Pint, D. C. Marcano, C. Zhang, J. Yao, G. Ruan, Z. Yan, Y. Zhu, R. H. Hauge, J. M. Tour, Nat. Commun. 2011, 2, 559.
[44] D. Kuzum, H. Takano, E. Shim, J. C. Reed, H. Juul, A. G. Richardson, J. De Vries, H. Bink, M. A. Dichter, T. H. Lucas, D. A. Coulter, E. Cubukcu, B. Litt, Nat. Commun. 2014, 5, 5259.
[45] S.-H. Bae, Y. Lee, B. K. Sharma, H.-J. Lee, J.-H. Kim, J.-H. Ahn, Carbon 2013, 51, 236.
[46] X. Li, W. Cai, J. An, S. Kim, J. Nah, D. Yang, R. Piner, A. Velamakanni, I. Jung, E. Tutuc, S. K. Banerjee, L. Colombo, R. S. Ruoff, Science 2009, 324, 1312.
[47] A. M. H. Ng, Y. Wang, W. C. Lee, L. C. Teck, K. P. Loh, H. Y. Low, Carbon 2014, 67, 390.
[48] K. Yong, A. Ashraf, P. Kang, S. Nam, Sci. Rep. 2016, 6, 24890.
[49] M. Hofmann, Y.-P. Hsieh, A. L. Hsu, J. Kong, Nanoscale 2014, 6, 289.
[50] M. F. El-Kady, R. B. Kaner, Nat. Commun. 2013, 4, 1475.
[51] B. Senyuk, N. Behabtu, A. Martinez, T. Lee, D. E. Tsentalovich, G. Ceriotti, J. M. Tour, M. Pasquali, I. I. Smalyukh, Nat. Commun. 2015, 6, 7157.
[52] J. Lin, Z. Peng, Y. Liu, F. Ruiz-Zepeda, R. Ye, E. L. G. Samuel, M. J. Yacaman, B. I. Yakobson, J. M. Tour, Nat. Commun. 2014, 5, 5714.
[53] H. Tian, Y. Shu, Y.-L. Cui, W.-T. Mi, Y. Yang, D. Xie, T.-L. Ren, Nanoscale 2014, 6, 699.
[54] H. Tian, Y. Shu, X.-F. Wang, M. A. Mohammad, Z. Bie, Q.-Y. Xie, C. Li, W.-T. Mi, Y. Yang, T.-L. Ren, Sci. Rep. 2015, 5, 8603.
[55] S. R. Das, Q. Nian, A. A. Cargill, J. A. Hondred, S. Ding, M. Saei, G. J. Cheng, J. C. Claussen, Nanoscale 2016, 8, 15870.
[56] J. S. Lee, N. H. Kim, M. S. Kang, H. Yu, D. R. Lee, J. H. Oh, S. T. Chang, J. H. Cho, Small 2013, 9, 2817.
[57] Q. He, H. G. Sudibya, Z. Yin, S. Wu, H. Li, F. Boey, W. Huang, P. Chen, H. Zhang, ACS Nano 2010, 4, 3201.
[58] W. Zheng, in Polymer Thin Films (Ed: A. A. Hashim), InTech, Rijeka, Croatia 2010, Ch. 10.
[59] S. Ebnesajjad, C. Ebnesajjad, Surface Treatment of Materials for Adhesion Bonding, 2nd ed., William Andrew Publishing, Norwich, NY, USA 2014, Ch. 5.
[60] H. Kim, B. Yoon, J. Sung, D.-G. Choi, C. Park, J. Mater. Chem. 2008, 18, 3489.
[61] W.-W. Liu, B.-Y. Xia, X.-X. Wang, J.-N. Wang, Front. Mater. Sci. 2012, 6, 176.
[62] Dupont Kapton Summary of Properties, https://www.dupont.com/content/dam/dupont/products-and-services/membranes-and-films/polyimde-films/documents/DEC-Kapton-summary-of-proper-ties.pdf (accessed: March 2017).
[63] I.-Y. Jeon, H.-J. Choi, M. J. Ju, I. T. Choi, K. Lim, J. Ko, H. K. Kim, J. C. Kim, J.-J. Lee, D. Shin, S.-M. Jung, J.-M. Seo, M.-J. Kim, N. Park, L. Dai, J.-B. Baek, Sci. Rep. 2013, 3, 2260.
[64] X. Feng, Y. Zhang, J. Zhou, Y. Li, S. Chen, L. Zhang, Y. Ma, L. Wang, X. Yan, Nanoscale 2015, 7, 2427.
[65] Y. R. Jeong, H. Park, S. W. Jin, S. Y. Hong, S.-S. Lee, J. S. Ha, Adv. Funct. Mater. 2015, 25, 4228.
[66] 3M™ Electrically Conductive Adhesive Transfer Tape 9707, https://multimedia.3m.com/mws/media/5369570/3mtm-electrically-con-ductive-adhesive-transfer-tape-9707.pdf (accessed: May 2014).

[67] P. S. Schnable, D. Ware, R. S. Fulton, J. C. Stein, F. Wei, S. Pasternak, C. Liang, J. Zhang, L. Fulton, T. A. Graves, P. Minx, D. Reily, L. Courtney, S. S. Kruchowski, C. Tomlinson, C. Strong, K. Delehaunty, C. Fronick, B. Courtney, S. M. Rock, E. Belter, F. Y. Du, K. Kim, R. M. Abbott, M. Cotton, A. Levy, P. Marchetto, K. Ochoa, S. M. Jackson, B. Gillam, W. Chen, L. Yan, J. Higginbotham, M. Cardenas, J. Waligorski, E. Applebaum, L. Phelps, J. Falcone, K. Kanchi, T. Thane, A. Scimone, N. Thane, J. Henke, T. Wang, J. Ruppert, N. Shah, K. Rotter, J. Hodges, E. Ingenthron, M. Cordes, S. Kohlberg, J. Sgro, B. Delgado, K. Mead, A. Chinwalla, S. Leonard, K. Crouse, K. Collura, D. Kudrna, J. Currie, R. F. He, A. Angelova, S. Rajasekar, T. Mueller, R. Lomeli, G. Scara, A. Ko, K. Delaney, M. Wissotski, G. Lopez, D. Campos, M. Braidotti, E. Ashley, W. Golser, H. Kim, S. Lee, J. K. Lin, Z. Dujmic, W. Kim, J. Talag, A. Zuccolo, C. Fan, A. Sebastian, M. Kramer, L. Spiegel, L. Nascimento, T. Zutavern, B. Miller, C. Ambroise, S. Muller, W. Spooner, A. Narechania, L. Y. Ren, S. Wei, S. Kumari, B. Faga, M. J. Levy, L. McMahan, P. Van Buren, M. W. Vaughn, K. Ying, C. T. Yeh, S. J. Emrich, Y. Jia, A. Kalyanaraman, A. P. Hsia, W. B. Barbazuk, R. S. Baucom, T. P. Brutnell, N. C. Carpita, C. Chaparro, J. M. Chia, J. M. Deragon, J. C. Estill, Y. Fu, J. A. Jeddeloh, Y. J. Han, H. Lee, P. Li, D. R. Lisch, S. Liu, Z. Liu, D. H. Nagel, M. C. McCann, P. SanMiguel, A. M. Myers, D. Nettleton, J. Nguyen, B. W. Penning, L. Ponnala, K. L. Schneider, D. C. Schwartz, A. Sharma, C. Soderlund, N. M. Springer, Q. Sun, H. Wang, M. Waterman, R. Westerman, T. K. Wolfgruber, L. Yang, Y. Yu, L. Zhang, S. Zhou, Q. Zhu, J. L. Bennetzen, R. K. Dawe, J. Jiang, N. Jiang, G. G. Presting, S. R. Wessler, S. Aluru, R. A. Martienssen, S. W. Clifton, W. R. McCombie, R. A. Wing, R. K. Wilson, Science 2009, 326, 1112.

[68] A. Kozbial, Z. Li, C. Conaway, R. McGinley, S. Dhingra, V. Vahdat, F. Zhou, B. D'Urso, H. Liu, L. Li, Langmuir 2014, 30, 8598.

[69] X. D. Huang, S. M. Bhangale, P. M. Moran, N. L. Yakovlev, J. Pan, Polym. Int. 2003, 52, 1064.

[70] Accu Dyne Test, https://www.accudynetest.com/polytable_02.html (accessed: April 2017).

[71] Graphene Supermarket, https://graphene-supermarket.com/Con-ductive-Graphene-Dispersion-100.html (accessed: January 2017).

5. Supporting Information for Adv. Mater. Technol., DOI: 10.1002/admt.201700223
High-Resolution Patterning and Transferring of Graphene-Based Nanomaterials onto Tape Toward Roll-to-Roll Production of Tape-Based Wearable Sensors
Supplementary Method As will be appreciated by those skilled in the art, variations on the foregoing specific example are possible. Some examples follow:
PDMS Mold Fabrication In the method illustrated at FIG. 1, PDMS negative patterns were fabricated using soft lithography. In this step, a silicon wafer with photoresist SU-8 (3050; Microchem, Westborough, MA) was spin-coated to produce different thicknesses by adjusting rotation speed and duration. Then, the wafer was baked at 65° C. for 5 min and 90° C. for 1 hr. Subsequently, the wafer was exposed to an ultraviolet light with another photomask, baked at 90° C. for 30 min, and developed to form a master mold for the microfluidic channels. Following that, PDMS solution and its curing agent (Sylgard 184, Dow Corning, Auburn, MI) with a weight ratio of 10:1 was mixed, degassed, poured on the master mold and thermally cured at 65° C. for 2 hr on a hotplate. Finally, the cured PDMS containing negative patterns was peeled from the master mold.

In a similar method, illustrated at FIGS. 9 A-B, is a schematic representation of the formation of graphene patterns 14/16 on a 1 meter long polyimide tape 12. (a) Negative features 93 created on a ¼-inch thick poly(methyl methacrylate) or PMMA sheet 92 using a high-precision CNC milling machine. (b) PDMS precursor solution 94 poured over and cured on the patterned PMMA sheet 92/93. (c) PDMS mold with positive features 94/95 peeled off from the PMMA surface 92/93. (d) PDMS precursor solution 22 poured over and curved on the PDMS mold 94/95 with positive features formed in (c). (e) PDMS mold 21 with negative features 22 peeled off from the mold 94/95 formed in (d). (f) Graphene patterns 14/16 formed inside the negative patterns 22 at the PDMS surface using the D2SP method. (g) A double-sided polyimide tape 12 adhered onto the PDMS surface containing the negative patterns 22. (h) Graphene patterns 14/16 transferred onto the double-sided polyimide tape 12 and then covered by non-adhesive liner.

FIGS. 10A-D. XPS high-resolution spectra of the graphene patterns on a polyimide tape (such as made by the method of FIG. 9) without thermal treatment and annealed at 150° C. and 250° C. for 180 min. (a) O s. (b) C 1s. (c) Si 2p. (d) N 1s. This shows how controlled annealing can improve at least adhesion of graphene pattern 14 to tape 12.

FIGS. 11A-D. XPS high-resolution spectra of the polyimide tape of FIGS. 10A-D alone, without thermal treatment and annealed at 150° C. and 250° C. for 180 min. (a) O 1s. (b) C 1s. (c) Si 2p. (d) F 1s. This further shows how annealing of both tape 12 and graphene pattern 14 is of benefit.

Figure 12:
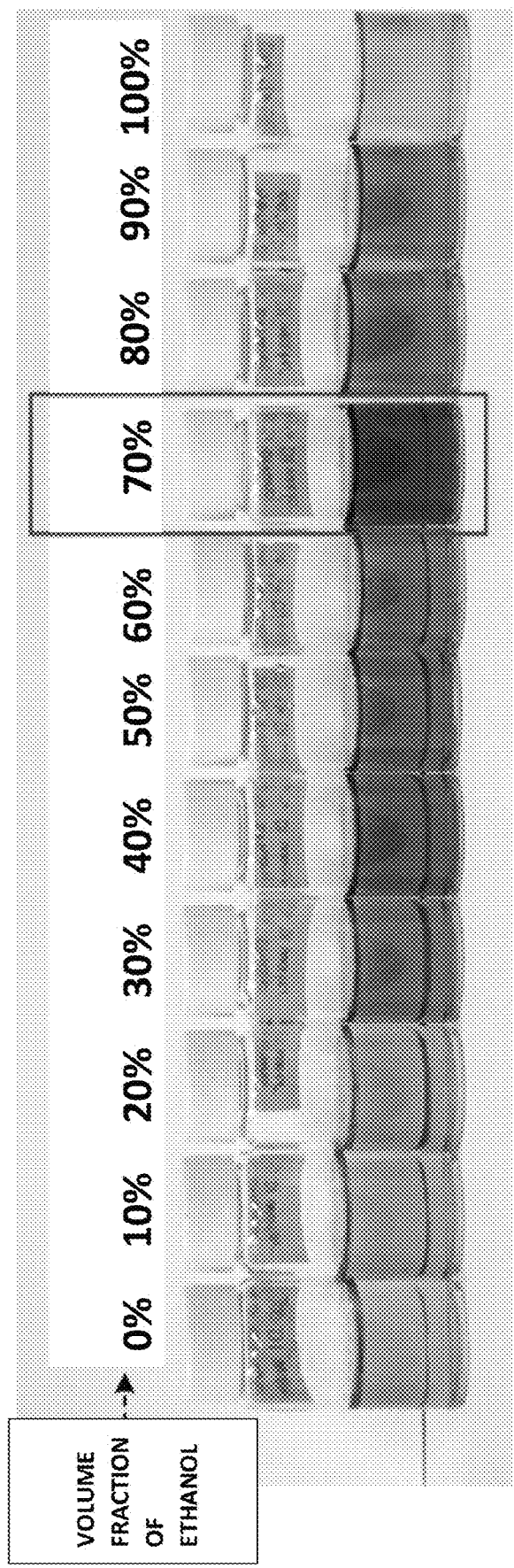

FIG. 12. Optical images of graphene dispersions in ethanol and distilled water (DI) mixture with different volume fraction ratios of ethanol. These are examples of possible starting solutions for drop casting in the methods of FIGS. 1 and 9.

TABLE S1

Surface energies of different materials and work of adhesion at the interfaces between two contacting materials utilized in this work.

| Materials | Surface energy (mJ · m$^{-2}$) | | | Work of adhesion (mJ · m$^{-2}$) |
| --- | --- | --- | --- | --- |
| | $\gamma$ | $\gamma^d$ | $\gamma^p$ | $W_{A-B}$ |
| PDMS [61] | 19.8 | 19 | 0.8 | |
| Graphene [68] | 51.6 | 43.5 | 8.1 | |
| Polyimide tape [69] | 46 | 44 | 2 | |
| Scotch tape (Synthetic rubber adhesive) [70] | 33.6 | 33.6 | 0 | |
| Scotch tape (Acrylic adhesive) [70] | | | | |
| 3M ™ conductive tape (Acrylic adhesive) [70] | 30.2 | 28.9 | 1.3 | |
| Aluminum foil tape (Acrylic adhesive) [70] | | | | |
| Graphene-PDMS | | | | 55.8 |
| Graphene-Polyimide tape | | | | 93.9 |
| Graphene-Scotch tape (Synthetic rubber adhesive) | | | | 75.8 |
| Graphene-Scotch, 3M ™, or Aluminum foil tape (Acrylic adhesive) | | | | 73.9 |

Essentially, adhesion is achieved due to the molecular contact and surface force formed over the interfacial surface of two materials [60]. Work of adhesion is defined as the energy required to separate two bonded materials by repelling surface force and damaging molecular contact at the interface between two contacting materials, as determined by their surface energies[59]. Removal of the excess graphene from the PDMS surface using a tape in the D²SP process, and subsequent transferring of the formed graphene patterns from the PDMS channel onto a target tape in the ST process result from having the difference of the work of adhesion at the interface of the graphene-tape and the graphene-PDMS. Table S1 presents the surface energies of the materials and work of adhesion (calculated by using Equation 1) when they are bonded with graphene. In our method, for the D2SP process, because $W_{Graphene-PDMS}$ (55.8 mJ·m⁻²)<$W_{Graphene-Scotch}$ (75.8 mJ·m⁻²; note: the Scotch tape used here use a synthetic rubber adhesive), it is possible to peel off the excess graphene from the PDMS surface. Further, for the ST process, the requirements of $W_{Graphene-PDMS}$ (55.8 mJ·m⁻²)<$W_{Graphene-Polyimide}$ (93.9 mJ·m⁻²) and $W_{Graphene-PDMS}$ (55.8 mJ·m⁻²)< $W_{Graphene-Scotch}$ (73.9 mJ·m⁻²; note: the Scotch tape used here has an acrylic adhesive which is also used at the 3M™ and aluminum foil tapes) are also met, thus ensuring the successful transfer of the patterned graphene onto the polyimide, Scotch, 3M™ and aluminum foil tapes.

The foregoing provides additional guidance on some of the features and factors a designer could consider in implementing aspects of the invention.

D. Specific Example 2—Wrinkled Tape

Figure 13A:
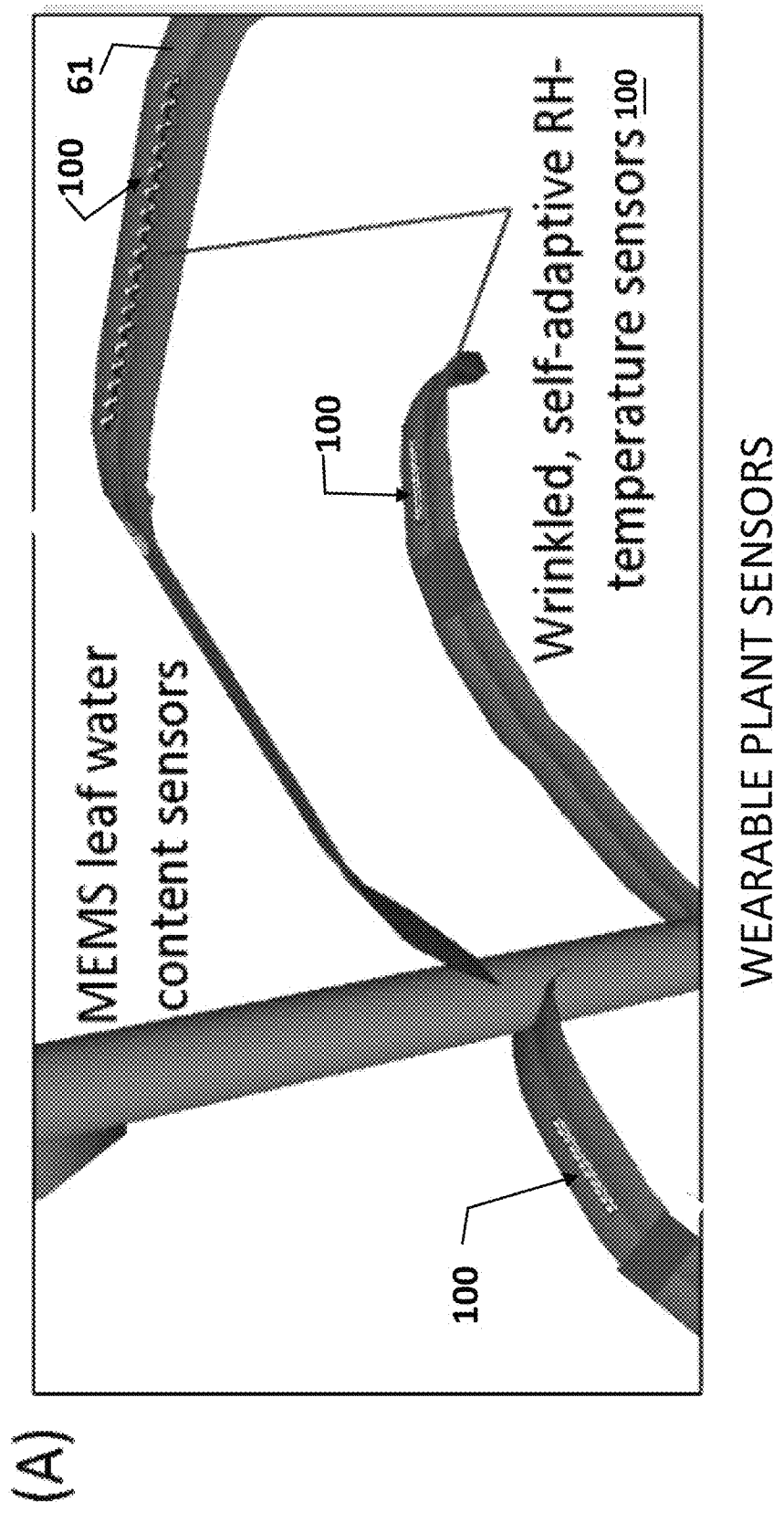
Figure 13B:
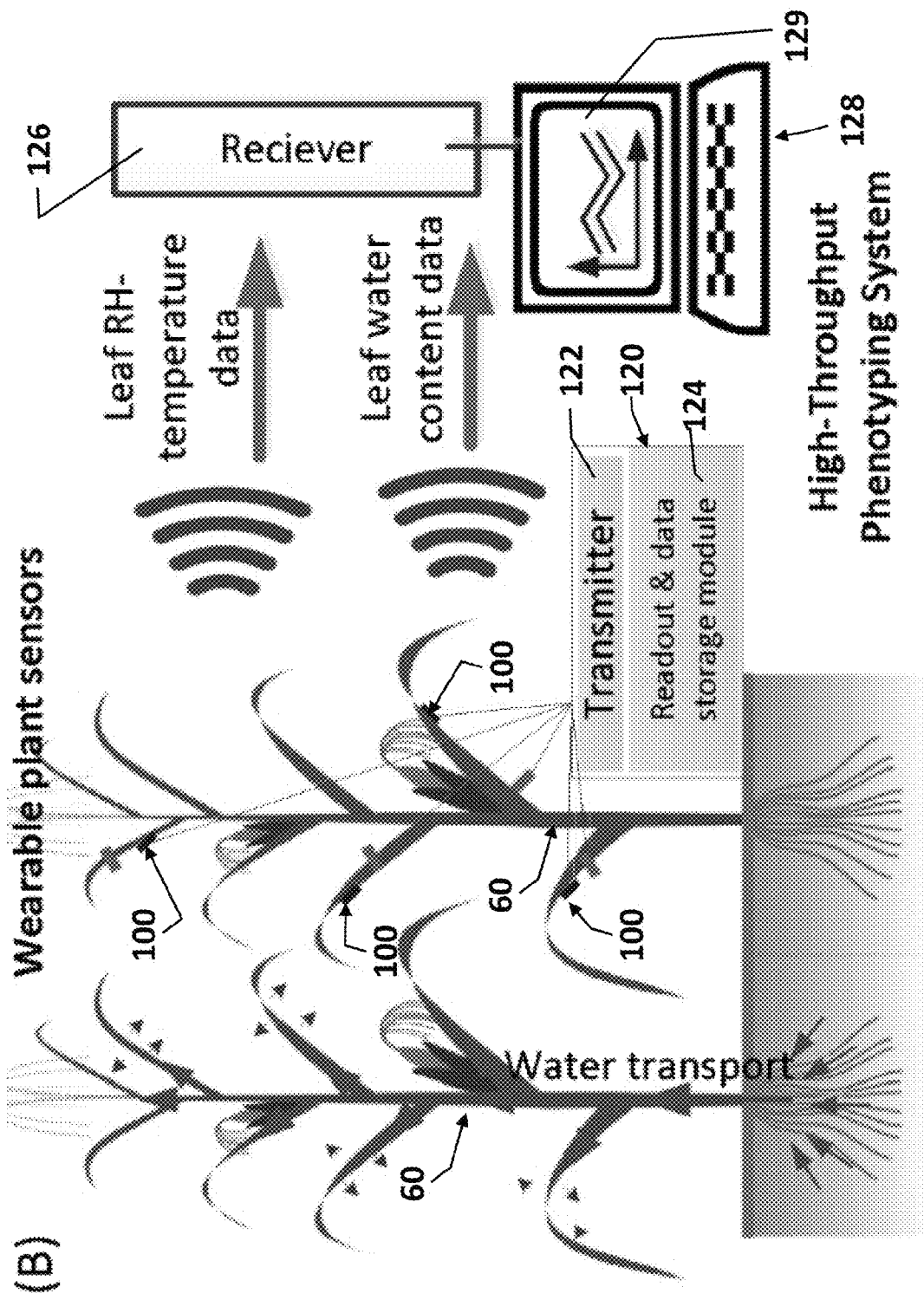

FIGS. 13A and B through 17 illustrate an alternative embodiment according to aspects of the invention. Using techniques previously described regarding high resolution patterning of a flexible tape, this embodiment 100 has features beneficial at least to mounting on a surface that either itself flexes, elongates or contracts, or otherwise has anchors to a surface under investigation (e.g. plant leaf 61) that translate relative to one another (e.g. as the leaf flexed and grows).

As indicated in these Figures, one example application is mounting on live plants. As will be appreciated, the mounting and the structure of an assembly 100 allows assembly 100 to move with movement of a plant leaf 61 when disrupted (e.g. by machine or animal, rain, and the like). But also, importantly, it can allow retention of assembly 100 on the plant as it grows over the growing season or at least a substantial part of the same.

Figure 14:
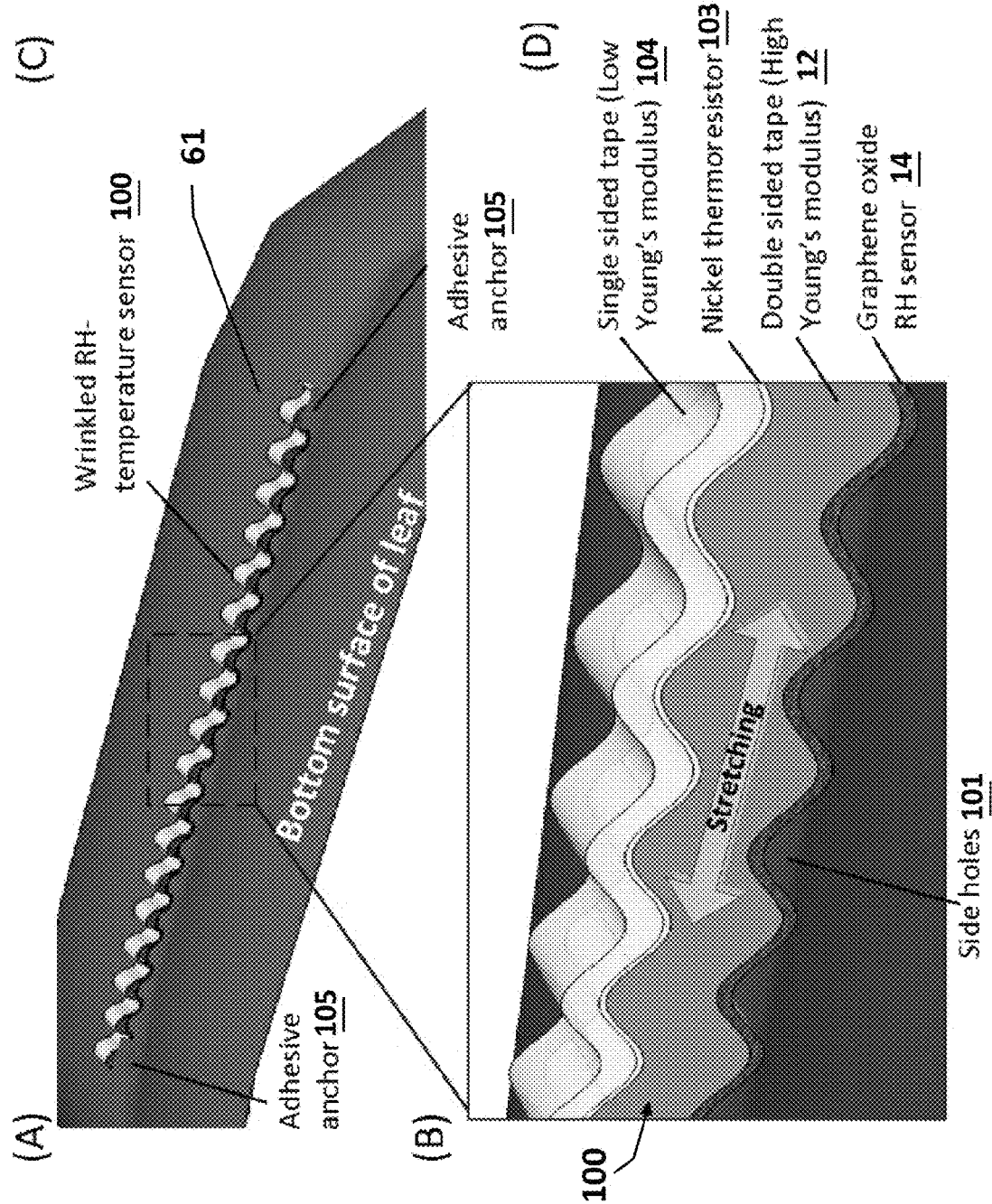

In this example, methodologies described elsewhere herein are utilized to pattern 14 with nanomaterials a flexible tape 12. As described below, by controlled fabrication of the set of components, the patterned tape 10 can itself be adhered to a pre-stretched layer (104 at FIG. 17) and adhere in that pre-stretched or elongated state. When allowed to release to a natural state, the patterned tape 10 is then wrinkled or forms undulations as shown in FIG. 14A. See also FIG. 17.

FIG. 14B illustrates this potential feature. Additional layers can be added of appropriate material to an additional functionality to assembly 100. In this example, nickel layer 103, with enough for flexibility, allows building into assembly 100 other sensor functionalities over and above what the sensor 100 will be used with the graphene pattern.

Figure 15:
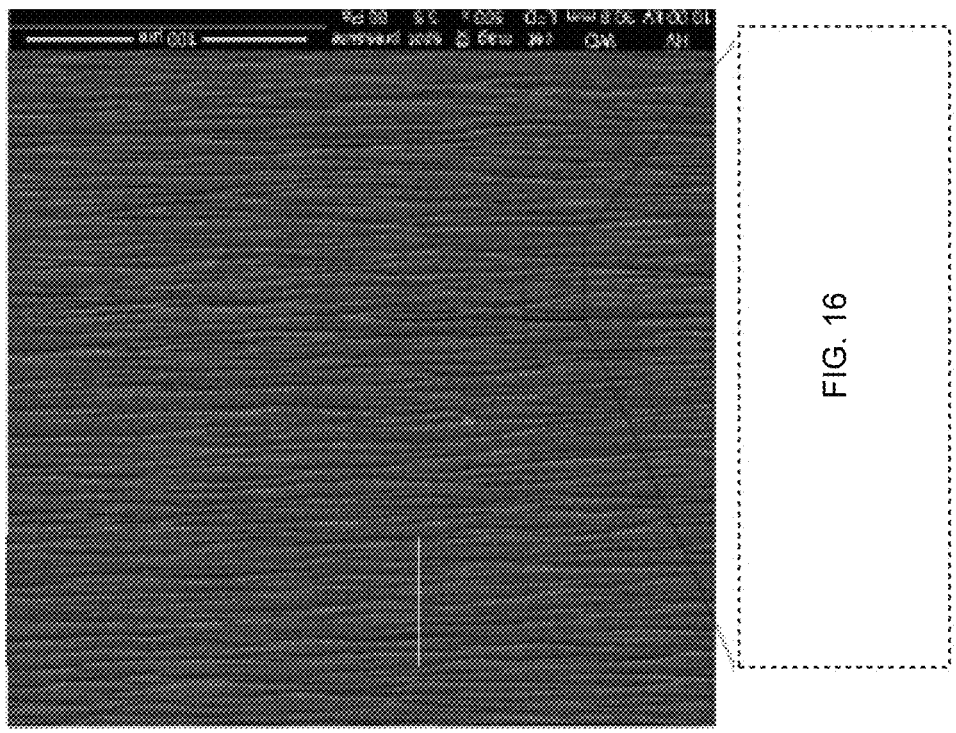
FIG. 15 shows a microscope image of such a surface with a further enlarged section in the extract to the bottom.
Figure 16:
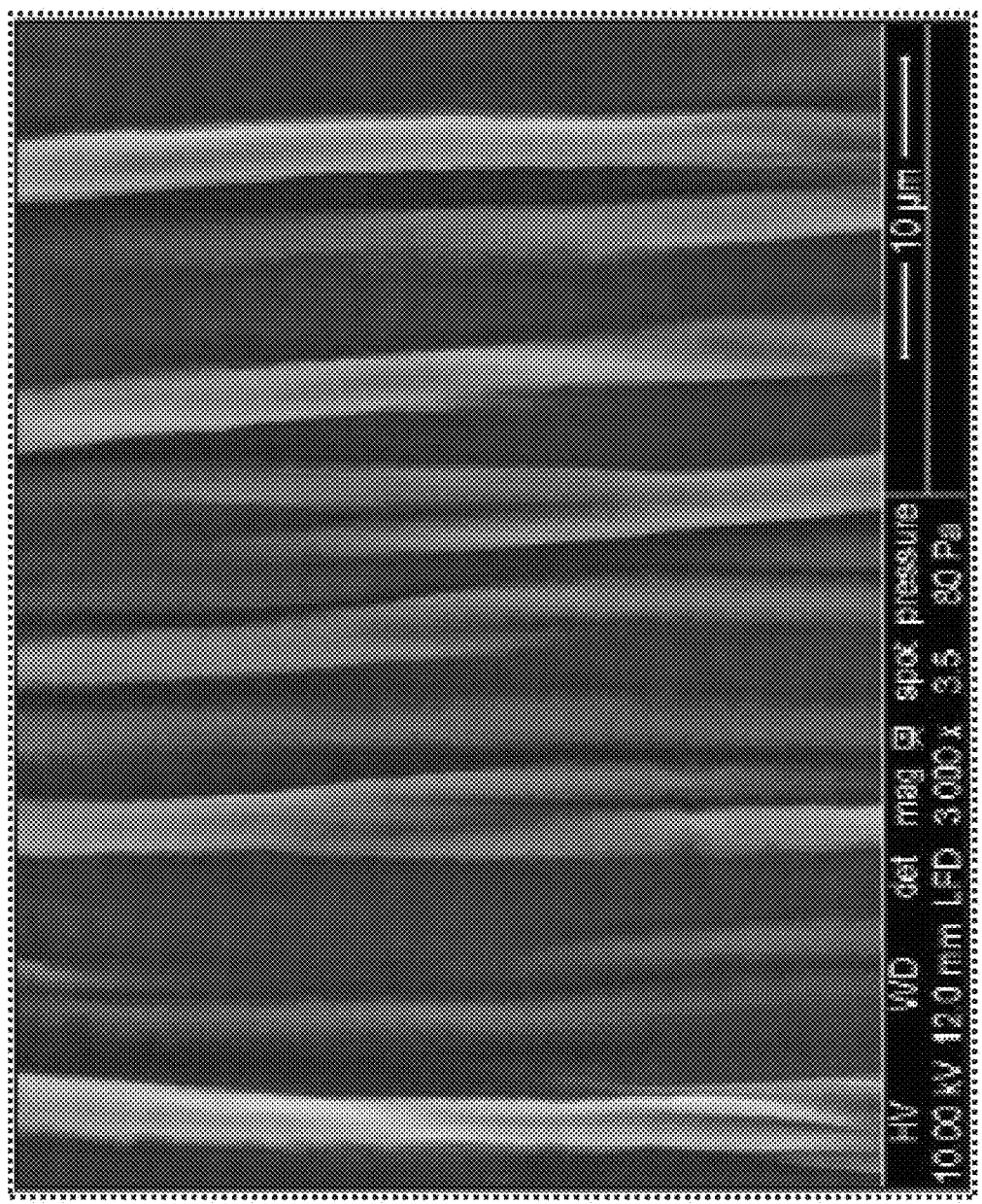
FIG. 16 shows the extract of FIG. 15 (bottom) in further enlarged scale.

FIGS. 15 and 16 illustrate further all aspects of this embodiment. Using higher Young's modulus double adhesive sided tape for sensor substrate 12 (to receive transferred graphene oxide sensor pattern 14), and lower but pre-stretched Young's modulus single adhesive sided tape 104, wrinkles the sensor combination 12/14. It has enough contact or proximity to leaf surface 61 to sense (here relative humidity) but can stay attached to leaf 61 as follows.

Opposite ends of assembly 100 are exposed adhesive 105 that anchor the relaxed assembly 100 to spaced apart locations of leaf 61. The adhesive can be bio-compatible (commercially available such as from Master Bond, Inc., Hackensack, NJ (USA) and sufficient to adhesively attached assembly 100 to leaf 61 over both typical range of mechanical forces and stresses (wind, machines, precipitation, animals) against leaf 61 or assembly 100 while growing. But eh wrinkled configuration allows leaf 61 to grow while assembly 100 stays anchored to leaf 61. Still further, a subtle feature of wrinkled assembly ley 100 is as follows. Side holes 101 (or spaces to ambient air) transversely under assembly 100 between the wrinkles allow transpiration from the plant leaf 61 to be sensed. Here, for example, the patterned graphene is adapted to measure relative humidity (RH) at leaf 61. The graphene is configured to attract water vapor toward that end.

But additionally, adding the nickel layer 103 also provides on-board sensor 100 a temperature sensor at leaf 61 for concurrent RH/temperature measurements.

FIG. 17 show one fabrication method for the wrinkled assembly 100. As can be seen, this simple but coordinated combination adds enhanced to functionalities to the same sensor assembly.

Note further that by the simple addition of appropriate its use of adhesive anchors spaced apart locations on the assembly 100 (the anchor points in the Figures). The whole assembly 100 can be attached it to spaced apart positions on the plant leaf 61. As the plant leaf grows over time, those anchor points would move farther apart with such growth. The unwrinkling of the sensor body can then elongate with that growth. The designer would design the amount of wrinkling to be effective for at least substantial growth of a leave. This can be adjusted according to need or desire.

Additional details showing how different sensors on a plant can work together for beneficial results follows.

E. Specific Example 3—Sensors to Advance High-Throughput Phenotyping for Water Use Dynamics Examples of development, optimization, and application of sensors according to one or more aspects of the invention are set forth below. In one application, they can be used to provide direct, reliable and affordable measurements for water use dynamics, including water vapor evaporation induced variation in relative humidity (RH) at leaf surfaces.

The approach is to use a structurally transformable plant sensor 100 for detection of RH at the leaf surface. The wearable RH plant sensor 100 integrates a temperature sensing unit (e.g. ref. no. 103, FIG. 17) to monitor both RH and temperature changes near the leaf surface in real time with high accuracy, enabling calculation of vapor pressure deficit (VPD). Because the sensors are fabricated on surfaces of air/water permeable, biocompatible, and flexible tape, the installation of sensors on leaf surfaces is simple. More importantly, the sensor 100 can self-adjust its overall size and transform its shape to adapt to the growth of leaves, thus minimizing any possible physical and physiological influences on plant growth during long-term monitoring of RH and temperature.

The sensors 100 can be used to phenotype plant water use dynamics, which is a critical aspect of plant health. To produce biomass, plants must open their stomata (pores in the leaf) that provide access to atmospheric carbon dioxide which is necessary for photosynthesis. When the stomata are open, carbon dioxide flows freely into the leaf along a diffusion gradient. However, at the same time, water flows out of the leaf along the opposite diffusion gradient. This loss of water from the leaf, known as transpiration, represents an inescapable trade-off for plant production: as plants gather carbon dioxide, they lose water. If a crop is water stressed, stomata will close to reduce transpiration, but carbon dioxide uptake will also decline, resulting in reduced yield [16].

The sensors ability to transform the pace of agricultural research through the development of a proof-of-concept phenotyping platform that characterizes variation in crop water use through measurements that were previously impossible due to costs of materials and labor. The platform can enable the development of new crop cultivars for improved water use. The phenotyping system includes hundreds of flexible RH sensors 100 (with additional ability to monitor temperature and calculate VPD), a readout and data storage module 124, and a wireless data transfer and collection module 122 (together readout device 120).

This sensor application can measure differences in water dynamics across multiple hybrids, which exhibit substantial variation in all measured phenotypic traits. The selection for these water dynamics traits may result in the production of higher yielding hybrids.

The sensors also have the potential to assist in the development of hybrids whose deployment could provide positive environmental impacts. There is phenotypic variation for water use that can be harnessed to develop crop varieties that access more water and waste less water. Crops with greater transpiration reduce water and nutrient loss to subsurface drainage [9, 30]. Although plant breeding programs have made significant progress in collecting aboveground, in-field trait data using non-destructive cameras and imaging, high throughput and high-accuracy measurements of plant water dynamics have so far not been possible. Modern methods rely on proxies of water use such as $^{13}C$ abundance. Sensing of the plant processes that control water use are time-intensive, laborious, destructive and have low information relative to the spatiotemporal variability in water supply and demand.

Relative Humidity Plant Sensor and Water-Use Phenotyping: Preliminary Data

An adhesive tape-based RH sensor technology for direct measurement of RH at the leaf surface is shown in FIGS. 8A-E and 13A and B. The sensor 100 is advantageous over existing RH sensors due to easy installation, low-cost of manufacturing, and light weight. The sensor uses a gas/vapor permeable tape 12 as the device substrate. A water vapor-sensitive material 14, consisting of a mixture of graphene and graphene oxide (GO), is patterned on the tape 12 surface using the nanomaterial patterning and transferring method described in [27]. The graphene pattern 14 serves as an electrical resistor whose resistance changes with varying moisture levels in the surrounding environment. In principle, the chemical structure of GO is described as a graphene sheet bonded to oxygen in the form of carboxyl, hydroxyl, or epoxy functional groups, which provide GO with high hydrophilicity allowing the intercalation of different types of molecules (especially, polar molecules) [4]. As water vapor from a leaf 61 enters the carbon interlayer of GO, protons are generated via the reaction between water molecules with the functional groups, thus decreasing electrical impedance or increasing resistance of GO [36].

A platform for manufacturing tape-based wearable, conformable and flexible electronic sensors using high-resolution patterns of graphene and other nanomaterials is discussed above (see also [27]). The method is schematically described in FIGS. 1A-B and involves (i) creating graphene patterns inside pre-patterned negative features at the surface of a polydimethylsiloxane (PDMS) substrate using a "Drop cast-Dry-Stick-Peel" ($D^2SP$) method, (ii) transferring the resulting graphene patterns onto a final sticky tape via an easy-to-implement "Stick-and-Transfer" (ST) process, (iii) low-temperature thermal annealing to adjust electrical resistivity of the patterned sensitive materials, and (iv) building electrical contacts with conventional wire bonding methods. The method does not require the use of any expensive equipment, except for needing a reusable PDMS substrate containing negative features, which can be easily manufactured. These fabricated on-tape sensors are flexible enough to conform well to various irregular shapes of the sensed objects. This method outperforms many alternative approaches in terms of pattern spatial resolution, thickness control, process simplicity, and diversity with respect to functional materials and pattern geometries [28]. FIGS. 1A-B shows some sample patterns. The wrinkled RH sensors can be manufactured based on this method.

The plant RH sensor (FIGS. 8 A-B) is structured as a graphene strip transferred onto a water vapor and gas permeable acrylic adhesive tape [28]. Two additional tape strips of the same type are adhered to the two sides of the graphene pattern. This creates an air gap between the sensor surface and the leaf, as well as side openings for air exchange between inside and outside of the gap space. When stuck to the leaf surface, this tape exhibits excellent bonding characteristics with leaves and allows rapid transmission of oxygen and carbon dioxide for photosynthesis.

Figure 8E:
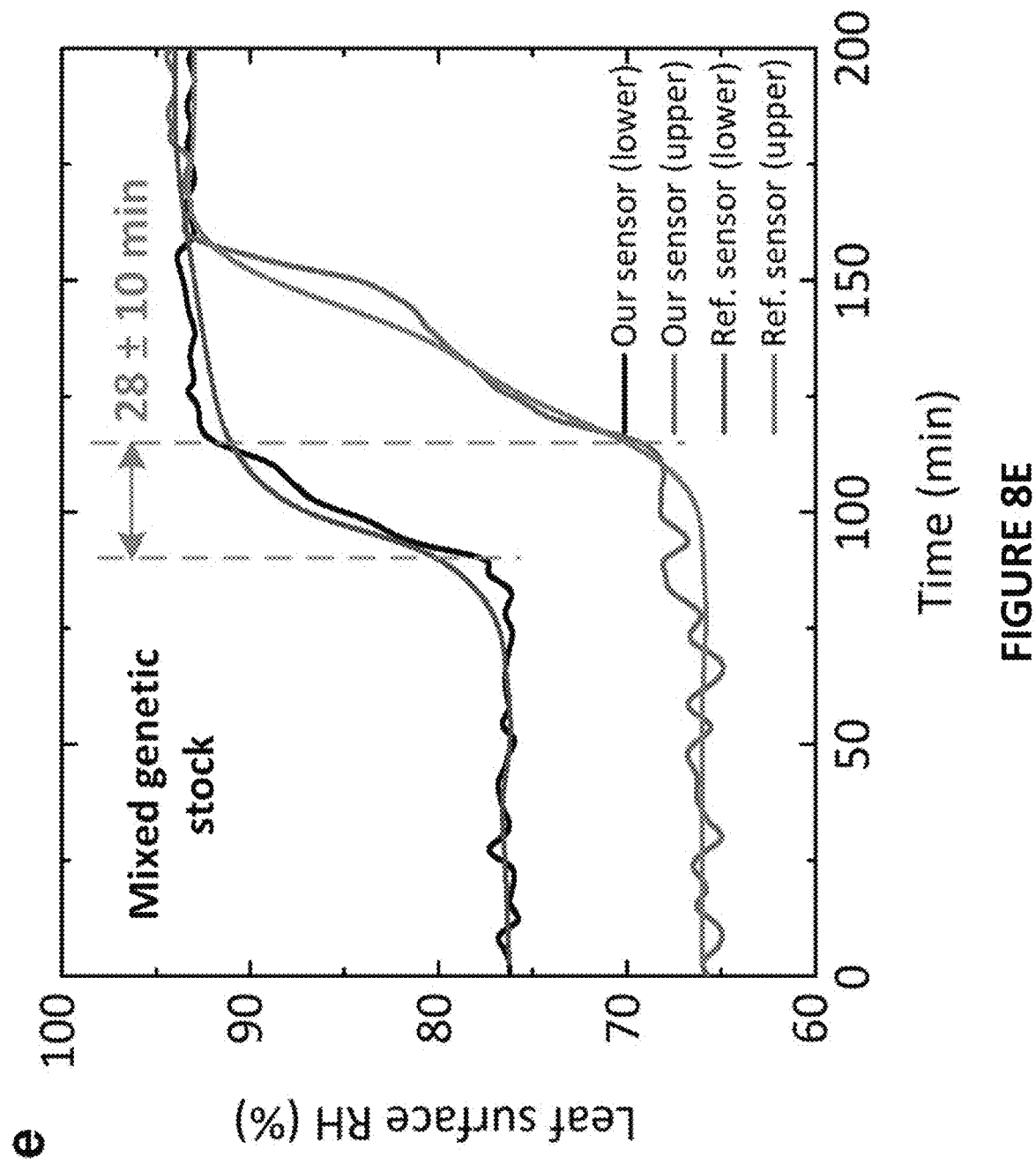

The tape-based RH sensors 100 can continuously monitor RH changes at the leaf surface in the greenhouse. We have used the sensors 100 to estimate the time required for water movement within a plant from the roots to the lower and upper leaves following simulated rain events that follow dry periods (FIGS. 8D-E). When water vapor escapes from the leaves, the local humidity level on the leaf surface increases (FIG. 8B). FIG. 8C shows the resistance response of the fabricated sensor exposed to different RH levels at constant room temperature. Importantly, by installing multiple RH sensors on different leaves to dynamically monitor variation in the RH at leaf surfaces, it is possible to track time points at which water loss increases on particular leaves, thus quantifying water transport time via the xylem from the roots to each of the measured leaves.

Anchors 64 to leaf 61 hold the graphene-based pattern 14 slightly above leaf 61 (see air gap 65) so that air movement for accurate readings is promoted. Side air openings 66 can be purposefully added to the senor 100 structure toward this end also. (see also FIG. 8B). Additional adhesive tape 63 (over and above any adhesive tape 12) can be used to help secure assembly 100 to leaf 61 and/or semi-enclose the sensor assembly 100 to leaf 61.

FIGS. 8D and 8E describe real-time monitoring of RH using the RH sensors installed on the back surfaces of the $4^{th}$ and $9^{th}$ leaf of two-month old maize plants. Here, one genotype (FIG. 8D) was the inbred line B73 [31]. The other genotype (FIG. 8E) was a mixed genetic stock (having a more complicated pedigree in which the female parent was a hybrid with no close relationship to B73, and the male parent was in a B73 background). The testing was initiated 15 min prior to irrigation. After irrigation, for B73, the lower and upper sensors exhibited a resistance increment and thus an increase in RH at 55 min and 135 min, respectively. Similarly, for the mixed genetic stock, the sensor outputs of the show that the lower and upper leaves had an increase in RH at 82 min and 110 min, respectively. Therefore, in both the B73 plants and plants with mixed genetic backgrounds, it took less time for water to be transported from the roots to the $4^{th}$ leaf than from the roots to the $9^{th}$ leaf. However, these two genetic stocks exhibited differences in the time lag between the increase in RH at the $4^{th}$ leaf and the increase in RH at the $9^{th}$ leaf (80±11 min, mean±standard deviation obtained from the measurements on three plants for B73 vs. 28±10 min, mean±standard deviation obtained from the measurements on three plants for the plants with a mixed genetic background). The low RH indicates the leaf pores are not open and thus the leaf is not photosynthesizing. The difference in time to increased RH (nearly one hour) is almost certainly agriculturally relevant because, in Iowa, there are only ~15 hours of light per day at the $9^{th}$ leaf stage (typically early June).

This method can easily transfer to other crops and lead to new basic and applied research capabilities. For example, the development of the sensors proposed in this project will enable researchers to address fundamental and important questions about crop physiology such as the relationship between variation in root morphology and variation in transpiration and water use efficiency. Hence, sub-daily real-time measurements of plant water dynamics could lead to new understanding of crop physiology, identify new traits to select for in breeding programs, improve irrigation efficiency and the deployment of climate resilient cultivars.

Testing occur under the following regime: Outfit individual field-grown plants with sensors. Begin sensing. Compare water transport dynamics of field-grown hybrids to their grain yields. Phenotyping will occur under conventional field operations (fertility, pesticides, etc.).

The RH sensor technology can be optimized from several aspects. First, integrate a temperature-sensing element into the RH sensor 100 to provide more reliable RH under varying temperature environments in practical field applications. This integration will allow calculation of vapor pressure deficit, which is the ultimate control on transpiration. This is because RH is a ratio of actual amount of water vapor in the air compared to the maximum water vapor the air is able to hold at a given temperature. Because RH is inversely related to the air temperature, i.e., if temperature increases, the value of RH decreases and vice versa. Second, introduce a stretchable, wrinkled substrate to the RH-temperature sensor capable of transforming and stretching its body size at the leaf surface to adapt to the plant growth during long-term, real-time RH monitoring (FIGS. 14A and B, 15 and 16). This will allow minimizing possible physical and physiological influences on the plant growth. In addition, aiming at field applications, we will design readout circuits and make a weather adaptable packaging for control, readout and data storage units and power supply. For example, the plant leaf sensors should be water-proof in wet environments such as rain.

Development of wearable RH-temperature sensor and adaptation to plant growth: Integrate a metallic temperature sensing unit 103 with the tape-based flexible RH sensor 100. Although many efforts are made to fabricate many kinds of flexible temperature sensing units, none have been able to conform to growing leaves. The sensor 100 has four layers (FIGS. 14 and 17), including from top to bottom, a patterned RH sensitive graphene oxide (with no piezoresistive effect) thin layer 14 (5 µm thick), a stiff gas permeable acrylic double-sided adhesive membrane 12 (20 µm thick), a patterned thermoresistive nickel thin layer 103 (0.5 µm thick), and a softer gas permeable polyurethane substrate 104 (200 µm thick). In this design, nickel is used as the thermosensitive material due to its large temperature coefficient of resistance or TCR=0.006° $C.^{-1}$ [12]. These laminated materials are in form of a wave-like wrinkled strip in one direction. In addition to the growth-adaptive stretching ability, the microscale wrinkles of the sensor will also help exiting of water vapor evaporation through the side holes 101 of the strip.

To form the wrinkles, we utilize a simple stretch-and-release method (FIGS. 14-17). The same method was previously used to realize a wrinkled graphene film on a soft elastomer substrate [1]. The 20 µm thick acrylic double-sided adhesive membrane film 12 (containing the RH and temperature sensitive materials) will be adhered to the softer polyurethane substrate 104 pre-stretched in one direction. As the bonded laminated layers are released, highly wrinkled surface textures will be formed on the sensor. The mechanism for this texturing is that during stretching, the stiffer layers yield and stretch irreversibly whereas the softer layer stretches reversibly. Thus, upon releasing, the stiffer layers buckle due to compressive stress imposed by the softer layer. The main fabrication procedures for the wrinkled sensor is shown in FIG. 17.

F. Specific Example 4—Added Components to Patterned Substrate

FIG. 18 gives another example of added functionality. Whether wrinkled or not, pattern substrate according to aspects of the invention could further be functionalized with other components. In this example a serpentine metal radio frequency antenna 130 to the surface of the substrate 12. This likewise can be made with the variety of an MEMS technique. One example is inkjet printing. Sometimes such intent as can be thin layers that are performed in can simply be adhered to the substrate. Thus, the sensor itself could carry on board a wireless communication interface 121 for remote or standoff wireless reading 120 of sensor measurements.

As will be appreciated by the skill in the art, depending on desire or need, and available surface area, one or more additional functional components could be added to the substrate.

Figure 19B:
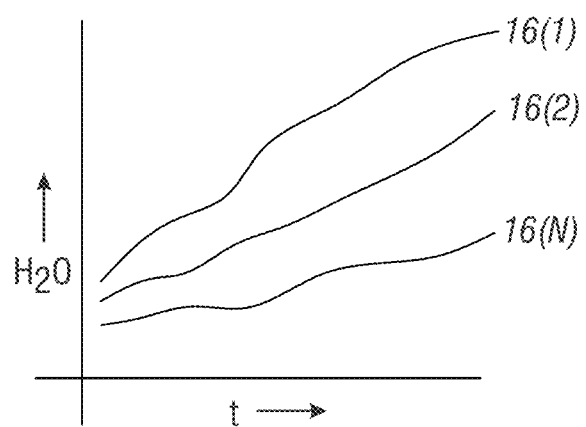

G. Specific Example 5—Plural Patterns Per Substrate for Spatially-Separated Measurements FIGS. 19A-B illustrate an exemplary sensor set up with the following features. In this case is the substrate is imprinted with plural patterns 16(1), 16(2), . . . , 16(n) according to the aspects of the invention. Each is spatially separate related along the substrate. When mounted to the surface under investigation (e.g. a plant leaf, human skin, animal skin, etc.), each of the spatially separated patterns 16 could function as spatially separate sensors. For example, it may be of interest to scientists to monitor the same nitrate or water content measurement but at spatially separated parts of that leave. The subtle benefit according to the invention is having these small, relatively inexpensive, essentially where all in the context off nondestructive noninvasive placement on a growing tissue, enables a wide variety of investigations into characteristics of a growing tissue in vivo. It could reveal highly valuable insights into how plants grow, use nutrients and the like. It also can be combined with other measurements. See FIGS. 15-17, to gain important correlations. An example would be patterning 14 and adding a temperature sensing function with the nickel layer 103.

Spatial differentiation, even in the context of mere millimeters on the same leaf, could also yield valuable insights.

H. Specific Example 6—Mounting of Patterned Substrate on Case

FIG. 20 is meant to diagrammatically indicate any of the patterned substrates 10, whether flexible or inflexible or otherwise according to aspects of the invention, could further be mounted on other structures. One example would simply be a case 140, or some other device, surface, or substrate. As indicated die grammatically in some of the Figures as well as FIG. 23, mounting of the thin layer patterned substrate 10 onto a case 140 could allow it to be protected against forces and environment. Ostensibly it could even be an enclosed case to encapsulated at least substantially (see, e.g., case cover 141). The case, its cover, or dedicated ports could allow air/gas exchange to the sensor 10 (see optionally through-holes 142 in cover 141 or in/out conduits 143/144 in case 140).

As can be appreciated, the form factor, function, materials, and reason for such case, housing, or additional substrate can vary according to need or desire.

I. Specific Example 7—Substrates Other than Adhesive Tape

FIGS. 21A, B illustrate an alternative to the foregoing. Sometimes added layers to the substrate with the patterning can have additional functional benefits. In this example, an additional layer 152 is placed over the patterning 14 on the substrate 12. That additional layer can be flexible or inflexible, permeable to gas and or liquid or not, completely transparent to opaque or anything in between, or have other filtering or material properties as the designer needs or desires.

In one example, a gas and/or fluid permeable layer 152 could be added over the patterning 14 on a polyamide adhesive tape 12 (many of which are at least substantially gas and water impermeable). This could add protection to the patterning 14 but allow communication with air or moisture for purposes of making measurements related to those environmental conditions.

As can also be appreciated that one or more additional layers 154 can be added either on the patterned side or the opposite side of the original patterned substrate 10. Note also other functional components (e.g. temp sensors, etc. at Ref No. 150) could be added at any layer 10, 152, or 154.

J. Specific Example 8—Mounting Patterned Substrate with Stretchable Legs and Adhesive Feet FIG. 22 illustrates an alternative mounting method for a patterned sensor 10. A small substrate 12 with single patterning 14/16 could be created according to any of the foregoing methods. To accommodate a variety of mechanical forces at such sensor 10, it could be mounted by radially extending stretchable legs 162. One example of such material is Ecoflex™ brand material available from BASF Corporation, Wyandotte, MI (USA). At the distal or foot portions 164 of each of the legs 162 could be an adhesive. The legs 162 would be anchored on whatever surface (e.g., plant leaf, human skin, animal skin) that is under investigation. The anchoring feet 164 with adhesive would be robust enough over a normal range of environmental conditions experienced that they would hold the patterned substrate 10 in position for the relevant sensing functionality of sensor 10. Even if that surface bends, elongate or contracts, or otherwise has portions with move relative to one another, stretchable legs 162 would accommodate the same over at least a range of distance.

K. Specific Example 9—Methodology

FIG. 23, discussed earlier, is intended simply to show one example of a method of fabrication of a pattern substrate. In this case it is focused on a flexible substrate including commercially available adhesive tape and using graphene as the national material that is patterned. As will be appreciated by those skilled in the art, the methodology can be applied in an analogous fashion to the other variations described herein.

L. Specific Example 10—Possible Applications

FIGS. 24A-C simply give nonlimiting examples of how aspects of the invention can be applied as wearable sensors, including on plants, humans (on skin or clothing), or animals (skin or hair mounted).

As can be appreciated, substantial activity has occurred recording such wearable sensors, including on other carriers such as clothing. As will be appreciated, a wide range of relevant measurements or monitoring with such wearable sensors as possible.

M. Options and Alternatives

As mentioned, the invention can take many different forms and embodiments. The examples given above are not limiting. Some variations are specifically mentioned. Others are, of course, possible as is understood by those skilled in this technical field.

A few examples of options and alternatives follow.
1. Substrate

As mentioned, one substrate for receiving the transferred nanomaterial pattern is single or double sided adhesive tape. Other substrates are possible.

As indicated, the designer can select from different types of tape materials and adhesives for either the cleaning tape or the target tape. Examples of tapes and strips having flexibility and adhesives can be seen at the following references, each of which is incorporated by reference herein:
L. Wang, J. Yu, Y. Zhang, H. Yang, L. Miao, and Y. Song, "Simple and Large-Scale Strategy to Prepare Flexible Graphene Tape Electrode", ACS Applied Materials & Interfaces, 2017, 9, 9095.
F. Tehrani, L. Reiner, and B. Bavarian, "Rapid Prototyping of a High Sensitivity Graphene Based Glucose Sensor Strip", PLOS One, Dec. 17, 2015.
Y. Chung, H. Kim, S. Lee, E. Lee, S. Kim, S. Ryu, and K. Cho, "Ubiquitous Graphene Electronics on Scotch Tape", Scientific Report, Jul. 29, 2015.
Lee et al., "Graphene-Transferring Member, Graphene Transferrer, Method of Transferring Graphene, and Methods of Fabricating Graphene Device by Using the Same, published Apr. 25, 2013.

These references also speak to options and alternatives regarding microscale nanoparticle-based sensors of different types, layering of nanoparticles such as graphene, and applications to different surfaces or objects.
2. Material for Patterning As mentioned, one material for patterning is graphene. Others are possible.

3. Graphene Layering

As mentioned earlier, one aspect of the invention can include a repetitive technique of drop casting, drying, removing or cleaning the surfaces around the negative image, and repeating. It is to be understood that each repeat would add another layer in the negative features of the mold.

As discussed above, this enables a layer-layer buildup of height of nanomaterials in the negative portions of the mold according to need or desire. As will be further understood, because it is a repetitive technique, each layer can be the same nanomaterials. But importantly, and alternatively, different layers could have different nanomaterials. Each D2SP cycle could form a layer of a specific material. After multiple cycles, multiple layers of different materials can be formed in a lamination or stack. Each layer could be different. Two materials could be alternated layer by layer. Or any variation thereof. This allows flexibility in designing what nanomaterials and what properties exist for the combined stack of layers once they are then transferred out of the negative features of the mold.

4. Annealing

If annealing is utilized after transfer of the nanomaterials to the target tape, there are a variety of ways to do so. Oven heating is one. Other possibilities are described in S. Das, Q. Nian, A. Cargill, J. Hondred, S. Ding, M. Saei, G. Cheng, and J. Claussen, "3D nanostructured inkjet printed graphene via UV-pulsed laser irradiation enables paper-based electronics and electrochemical devices", *Nanoscale*, vol. 8, no. 35, pp. 15870-15879, 2016, which is incorporated by reference herein, and which includes discussion of how at least graphene can be tuned as to its electrical properties by annealing.

What is claimed is:

1. A plurality of small-scale sensors comprising high spatial resolution patterned electrically functional nanomaterials made by a large-scale process comprising:
   a. providing a first roll comprising a plurality of negative mold patterns having three-dimensional negative features and spatial resolution in a surface of a flexible material;
   b. providing a second roll comprising a flexible, conformable transfer tape with an adhesive side;
   c. by a drop-cast-dry-stick-peel (D2SP) process, applying a solution including the electrically functional nanomaterials into the negative features of the negative mold patterns and over at least portions of the surface of the first roll one or more times, forming the solution into a thin film in the negative features of the negative mold patterns and over the at least portions of the surface of the first roll, and removing the formed thin film on the at least portions of the surface of first roll while leaving from the thin film positive patterns containing electrically functional nanomaterials with positive pattern features in the negative features of the negative mold patterns of the first roll; and
   d. by a stick-and-peel transfer (ST) technique, transferring electrically functional nanomaterials from the positive patterns in the negative features of the negative molds of the first roll to the second roll retaining the positive pattern features by bringing the adhesive side of the transfer tape of the second roll to the surface of the first roll and peeling the second roll from the first roll to create a plurality of positive patterns containing electrically functional nanomaterials on the second roll with substantially the spatial resolution of the negative mold patterns; and
   e. thereby producing for the plurality of small-scale sensors the plurality of positive patterns containing electrically functional nanomaterials on the flexible, conformal transfer tape for further use individually or in groups.

2. The sensors of claim 1 wherein the flexible, conformal transfer tape comprises adhesive tape.

3. The sensors of claim 1 wherein the one or more of the plurality of positive patterns are functionalized into:
   a. one or more force sensors,
   b. one or more pressure sensors, or
   c. one or more strain sensors.

4. The sensors of claim 1 wherein one or more of the plurality of positive patterns are functionalized into one or more sensors applied to one of lab gloves, human skin, or a computer mouse for real-time monitoring of motion and mechanical behaviors.

5. The sensors of claim 1 wherein one or more of the plurality of positive patterns are functionalized into one or more sensors applied to a plant leaf for real time monitoring of water loss from a plant.

6. The sensors of claim 1 wherein one or more of the plurality of positive patterns are functionalized into:
   a. one or more agriculture pesticide sensors;
   b. one or more soil nutrient sensors;
   c. one or more gas sensors, or
   d. one or more sweat or moisture sensors.

7. The sensors of claim 1 wherein one or more of the plurality of positive patterns are functionalized into one or more sensors applied to:
   a. fabric;
   b. skin; or
   c. plant leaf or tissue.

8. The sensors of claim 1 wherein one or more of the plurality of positive patterns are functionalized into one or more sensors applied to a structure for structural health monitoring.

9. The sensors of claim 8 wherein the structure comprises:
   a. a wall,
   b. a bridge,
   c. a wind turbine, or
   d. an engine.

10. The sensors of claim 1 wherein one or more of the sensors include an interface circuit for transduction and conversion of sensor measurements to sensor data.

11. The sensors of claim 10 wherein the interface circuit comprises one or more of:
   a. electrical leads;
   b. a transducer; and
   c. a wired or wireless communication module.

12. The sensors of claim 1 scaled in terms of:
   a. roll widths of the first and second rolls;
   b. roll lengths of the first and second rolls;
   c. density of at least one of the negative and positive patterns relative the first and second rolls; and
   d. types, shapes, functions, materials of the positive patterns.

13. The sensors of claim 1 produced by roll-to-roll (R2R) processing.

* * * * *